(12) United States Patent
VanDerWoude et al.

(10) Patent No.: US 11,370,006 B2
(45) Date of Patent: Jun. 28, 2022

(54) WASTE DISPOSAL SYSTEM AND WASTE RECEIVER FOR RECEIVING AND DISPOSING OF PHARMACEUTICAL WASTE MATERIAL

(71) Applicant: Stryker Corporation, Kalamazoo, MI (US)

(72) Inventors: Brian James VanDerWoude, Portage, MI (US); David A. Maness, Mount Pleasant, SC (US); Bryan Matthew Ulmer, Grand Rapids, MI (US); Dennis Meyer, Augusta, MI (US); Lucas Wade, Austin, TX (US); Stephen Myers, Austin, TX (US); Logan Castillo, Georgetown, TX (US); Heather Benoit, Austin, TX (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/166,091

(22) Filed: Feb. 3, 2021

(65) Prior Publication Data
US 2021/0154711 A1    May 27, 2021

Related U.S. Application Data

(60) Division of application No. 16/233,824, filed on Dec. 27, 2018, now Pat. No. 10,940,513, which is a
(Continued)

(51) Int. Cl.
*B09B 3/00*    (2022.01)
*A61B 50/37*   (2016.01)
(Continued)

(52) U.S. Cl.
CPC .......... *B09B 3/0075* (2013.01); *A61B 50/36* (2016.02); *A61B 50/362* (2016.02); *A61B 50/37* (2016.02);
(Continued)

(58) Field of Classification Search
CPC ..... A61B 19/02; A61B 19/0288; A61B 50/36; A61B 50/362; A61B 50/37; A61B 50/39;
(Continued)

(56) References Cited

U.S. PATENT DOCUMENTS

| | | | |
|---|---|---|---|
| 4,520,926 A | 6/1985 | Nelson | |
| 4,903,832 A | 2/1990 | Stewart | |

(Continued)

FOREIGN PATENT DOCUMENTS

| | | |
|---|---|---|
| CA | 2164727 A1 | 12/1994 |
| CN | 1071104 A | 4/1993 |

(Continued)

OTHER PUBLICATIONS

English language abstract and machine-assisted English translation for CN 204751174 extracted from espacenet.com database on Feb. 27, 2019, 7 pages.

(Continued)

*Primary Examiner* — Bryon P Gehman
(74) *Attorney, Agent, or Firm* — Howard & Howard Attorneys PLLC

(57) ABSTRACT

A waste disposal system with a waste receiver for receiving pharmaceutical waste material. A locking assembly is secured to a fixed surface and actuated from a locked configuration to an unlocked configuration. A lock cylinder of the locking assembly may extend forward of a front wall of a receiver body of the waste receiver to engage a locking feature of the cover in the locked configuration. A cover retention feature may prevent axial decoupling of the cover (Continued)

from the receiver body. An engagement feature is moved to be disengaged from the receiver body, and the receiver body is moved away from the fixed surface to disengage the locking assembly from the cover. The cover is decoupled from the cover retention feature, and coupled with the receiver body to seal the pharmaceutical waste material. The locking assembly may be removed from a lock passageway for disposal of the waste receiver.

20 Claims, 25 Drawing Sheets

Related U.S. Application Data continuation-in-part of application No. PCT/US2018/040359, filed on Jun. 29, 2018.

(60) Provisional application No. 62/527,544, filed on Jun. 30, 2017.

(51) Int. Cl.
| | |
|---|---|
| A61B 50/39 | (2016.01) |
| A61M 5/32 | (2006.01) |
| A61B 50/36 | (2016.01) |
| A62D 3/30 | (2007.01) |
| B09B 1/00 | (2006.01) |
| B65F 1/16 | (2006.01) |
| A61B 50/30 | (2016.01) |
| B09B 3/10 | (2022.01) |
| A61B 50/00 | (2016.01) |
| A61B 90/00 | (2016.01) |

(52) U.S. Cl.
CPC ............ *A61B 50/39* (2016.02); *A61M 5/3205* (2013.01); *A62D 3/30* (2013.01); *B09B 1/00* (2013.01); *B09B 3/10* (2022.01); *B65F 1/1615* (2013.01); *A61B 2050/005* (2016.02); *A61B 2050/0054* (2016.02); *A61B 2050/3008* (2016.02); *A61B 2090/0807* (2016.02); *B65F 2210/148* (2013.01); *B65F 2240/145* (2013.01)

(58) Field of Classification Search
CPC ...... A61B 2050/005; A61B 2050/0054; A61B 2050/3008; A61B 2090/0807; A61M 5/32; A61M 5/3205; A62D 3/30; B65D 81/26; B65F 1/10; B65F 1/12; B65F 1/14; B65F 1/16; B65F 1/1615; B65F 2210/148; B65F 2240/145; B09B 1/00; B09B 3/00; B09B 3/008; B09B 3/0075; B09B 3/10
See application file for complete search history.

(56) References Cited

U.S. PATENT DOCUMENTS

| | | | |
|---|---|---|---|
| 5,165,563 | A | 11/1992 | McKendry |
| 5,351,381 | A | 10/1994 | Case |
| 5,413,243 | A | 5/1995 | Bemis et al. |
| 5,419,435 | A | 5/1995 | Perzan et al. |
| 5,429,315 | A | 7/1995 | Wollert et al. |
| 6,588,436 | B2 | 7/2003 | Dunn et al. |
| 6,652,495 | B1 | 11/2003 | Walker |
| 7,918,776 | B2 | 4/2011 | Day |
| 7,918,777 | B2 | 4/2011 | Parrott |
| 8,348,056 | B2 | 1/2013 | Maness |
| 8,490,795 | B2 | 7/2013 | Ziemba |
| 8,534,459 | B2 | 9/2013 | Maness |
| 8,535,711 | B2 | 9/2013 | Anderson et al. |
| 8,573,426 | B2 | 11/2013 | Maness |
| 8,616,397 | B2 | 12/2013 | Maness |
| 8,875,881 | B2 | 11/2014 | Smudde et al. |
| 8,979,724 | B2 | 3/2015 | Fowler et al. |
| 9,044,377 | B2 | 6/2015 | Maness |
| 9,161,874 | B2* | 10/2015 | Pennings ............... A61B 90/00 |
| 9,302,134 | B1 | 4/2016 | Nelson et al. |
| 9,456,954 | B2 | 10/2016 | Maness |
| 9,707,324 | B2 | 7/2017 | Morgan et al. |
| 9,839,479 | B2 | 12/2017 | Sichau et al. |
| 9,962,227 | B2 | 5/2018 | Slaateng |
| 10,492,971 | B2* | 12/2019 | Pennings ................ B65F 1/163 |
| 10,524,873 | B2 | 1/2020 | Sall et al. |
| 11,185,639 | B2* | 11/2021 | Renstad .............. A61M 5/3205 |
| 2007/0032764 | A1 | 2/2007 | Lampropoulos |
| 2012/0024724 | A1 | 2/2012 | Beardsall et al. |
| 2012/0305132 | A1 | 12/2012 | Maness |
| 2014/0183070 | A1 | 7/2014 | Holaday et al. |
| 2016/0325322 | A1 | 11/2016 | Maness |
| 2016/0361456 | A1 | 12/2016 | Admani |
| 2019/0126331 | A1 | 5/2019 | VanderWoude et al. |

FOREIGN PATENT DOCUMENTS

| | | |
|---|---|---|
| CN | 204751174 U | 11/2015 |
| EP | 1380316 B1 | 10/2007 |
| FR | 2760647 A1 | 9/1998 |
| JP | H02129301 U | 10/1990 |
| WO | 8404068 A1 | 10/1984 |
| WO | 2014133398 A1 | 9/2014 |

OTHER PUBLICATIONS

English language abstract and machine-assisted English translation for EP 1 380 316 extracted from espacenet.com database on Feb. 27, 2019, 28 pages.

English language abstract and machine-assisted English translation for FR 2 760 647 extracted from espacenet.com database on Feb. 27, 2019, 14 pages.

International Search Report for Application No. PCT/US2018/040359 dated Nov. 13, 2018, 5 pages.

International Search Report for Application No. PCT/US2019/068578 dated Apr. 7, 2020, 5 pages.

Machine-assisted English translation for CN 1071104 extracted from espacenet.com database on Feb. 27, 2019, 22 pages.

Morris, Ph.D., Russell et al., "Performance Evaluation: RAPIX Filtration System for the Denaturing and Disposal of Unwanted Liquid Medications", Feb. 9, 2017, 4 pages.

Partial International Search Report for Application No. PCT/US2018/040359 dated Sep. 18, 2018, 4 pages.

Stericycle Inc., "Stericycle CSRX System Brochure", 2016, 2 pages.

Stryker, "Cactus Smart Sink Brochure—Frequently Asked Questions", 2017, 5 pages.

Stryker, "Controlled Substance Waste Management Systems Brochure", 2017, 6 pages.

Stryker, "Pharma Lock OR Controlled Substance Waste Management System, REF 0085-002-001 Instructions for Use", Apr. 2017, 13 pages.

Stryker, "Smart Sink Controlled Substance Waste Management System Instructions for Use, REF 0085-000-000", Apr. 2017, 29 pages.

Vail Scientific L.L.C., "Rapix Frequently Asked Questions", Oct. 21, 2016, 3 pages.

English language abstract and machine-assisted English translation for JPH 02-129301 U extracted from Japanese Patent Office database on May 16, 2022, 6 pages.

\* cited by examiner

WASTE DISPOSAL SYSTEM AND WASTE RECEIVER FOR RECEIVING AND DISPOSING OF PHARMACEUTICAL WASTE MATERIAL

CROSS-REFERENCE TO RELATED APPLICATION

This application is a division of U.S. patent application Ser. No. 16/233,824, filed on Dec. 27, 2018, which is a continuation-in-part of Patent Cooperation Treaty Application No. PCT/US2018/040359, filed on Jun. 29, 2018, which claims priority to and all the benefits of U.S. Provisional Patent Application No. 62/527,544, filed on Jun. 30, 2017, each of which is hereby incorporated by reference in its entirety.

BACKGROUND

The disposal of pharmaceutical waste material has long been a concern of those in the medical care industry. Pharmaceutical waste material may include, for example, expired or discontinued medicine, unused products such as partially or completely filled vials or IV bags, defective medicinal applicators, and other potentially dangerous or hazardous waste materials. The pharmaceutical waste material may be liquid phase pharmaceutical waste material contained within a syringe, bag, or bottle, or solid phase pharmaceutical waste material such as pills, capsules, powders, patches, etc. Ensuring that the pharmaceutical waste material is not improperly diverted or discarded has been of importance not only in the pharmaceutical and medical industries, but also in the field of environmental conservation. For example, sewering (i.e., simply discarding the pharmaceutical waste material down a drain) is associated with negative environmental consequences.

Under conventional disposal methods, the means by which pharmaceutical waste material may be disposed is often inconveniently dependent upon the specific type of waste. Labor and capital-intensive methods such as incineration are becoming much less preferred, and often require shipment of the pharmaceutical waste material outside the medical facility. The shipment of the pharmaceutical waste material is associated with risk of diversion during transport, and transport of liquid phase pharmaceutical waste material, which may include hazardous waste, is associated with regulatory and practical challenges.

Attempts to use waste disposal systems have not been altogether satisfactory. Conventional waste disposal systems occupy a substantial amount of valuable floor space in a hospital, for example, and may make providing such systems several points of use around the hospital unfeasible. Further, the conventional waste disposal systems may not provide adequate safeguards to foreclose the opportunity to retrieve and recover the waste material, a particularly pronounced problem with narcotic pain medications contained in pill and patch forms. Therefore, a need exists in the art for a waste disposal system that overcomes one or more of the aforementioned disadvantages.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
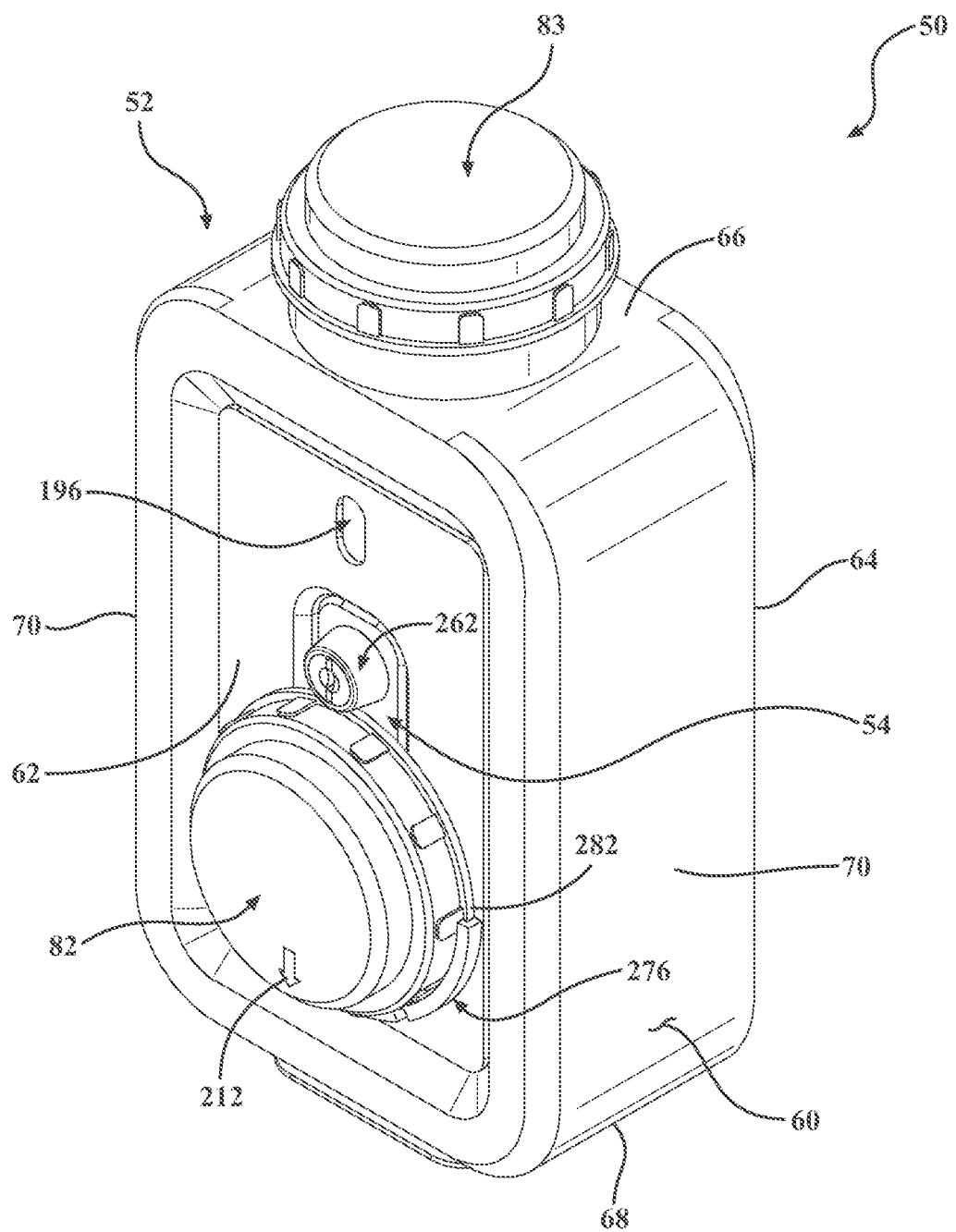
FIG. 1 is a perspective view of a waste disposal system including a waste receiver and a locking assembly.
Figure 2:
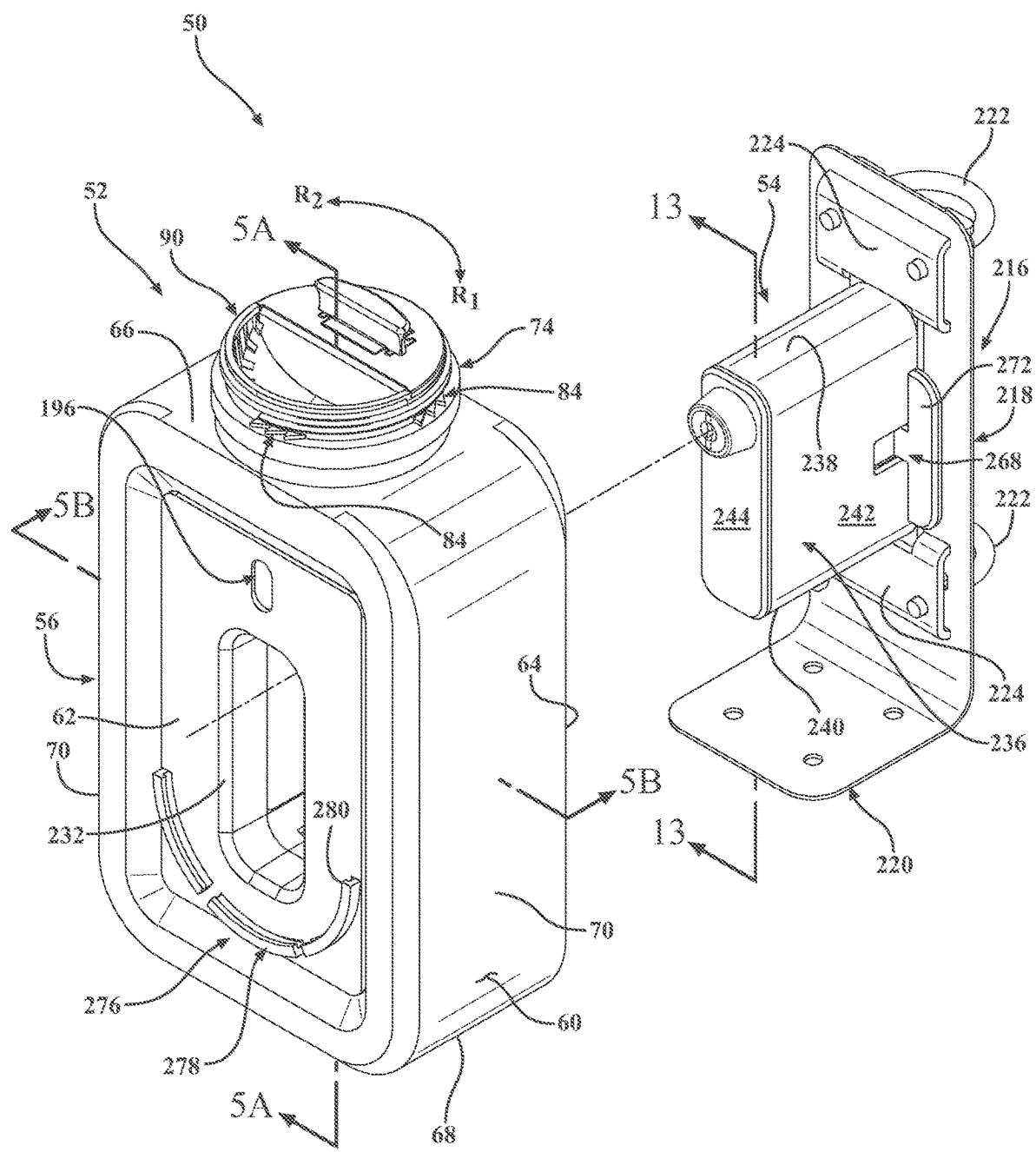
FIG. 2 is an exploded front perspective view of the waste disposal system of FIG. 1.
Figure 3:
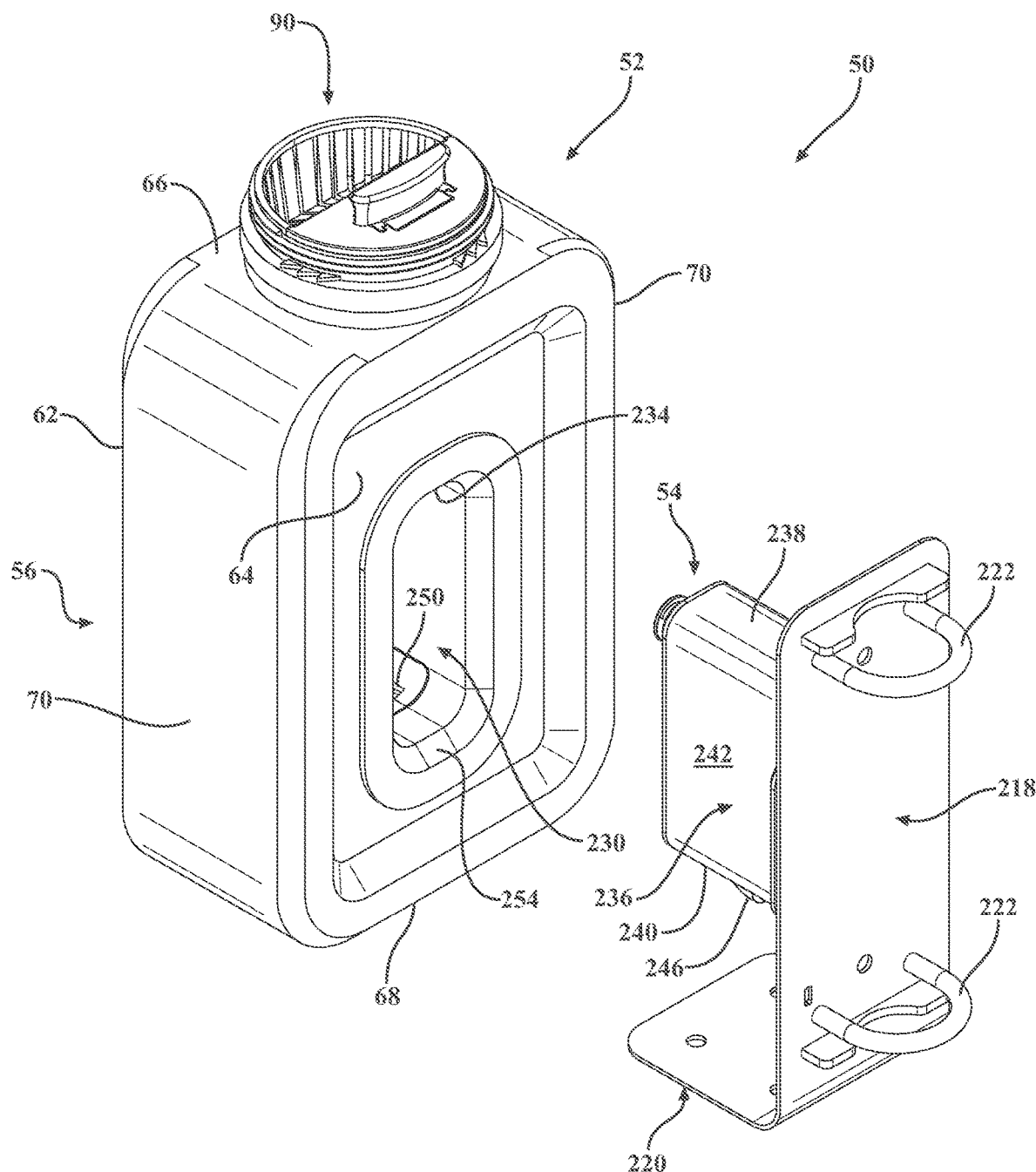
FIG. 3 is an exploded rear perspective view of the waste disposal system of FIG. 1.

FIGS. 1-3 show a waste disposal system 50 including a waste receiver 52 and a locking assembly 54. The waste receiver 52, in a most general sense, is a vessel or container providing for receipt and/or disposal of pharmaceutical waste material, preferably in a space-efficient manner that renders the waste material irretrievable and/or unrecoverable. As mentioned, the pharmaceutical waste material may include solid phase pharmaceutical waste material and/or liquid phase pharmaceutical waste material. Examples of solid phase pharmaceutical waste material of particular interest are patches and pills, and an example of liquid phase pharmaceutical waste material are fluid-based medications. As to be described in detail, the waste receiver 52 is adapted to be releasably secured to a fixed surface with the locking assembly 54. The locking assembly 54 minimizes or prevents unauthorized personnel from removing the waste receiver 52 from its service location. The locking assembly 54 and additional advantageous features of the waste disposal system 50 to be described lessen the likelihood that pharmaceutical waste material received within the waste receiver 52 may be improperly retrieved, recovered, and/or diverted.

The waste receiver 52 includes a receiver body 56 with at least an inner surface 59 defining a container volume 58 (see FIGS. 5A, 5B and 6), and an outer surface 60 opposite the inner surface 59. The inner surface 59 and the outer surface 60 cooperate to define at least one wall forming the receiver body 56 (see FIG. 6). The wall(s) may include a front wall 62 opposite a rear wall 64, a top wall 66 opposite a bottom wall 68, and one or more sidewalls 70 extending between the top and bottom walls 66, 68. The receiver body 56 may be monolithic in construction such that the walls 64-70 are integrally formed. FIGS. 1-3 show fillets extending between several adjacent, integrally-formed walls such that a discrete boundary between the adjacent walls is not clearly delineated, but it is understood that the front wall 62 is associated with a front of the receiver body 56, the rear wall 64 is associated with a rear of the receiver body 56, the top wall 66 is associated with a top of the receiver body 56, the bottom wall 68 is associated with a bottom of the receiver body 56, and the sidewalls 70 are associated with sides of the receiver body 56. The walls 64-70 form the receiver body 56 that is generally shaped as a rectangular prism. It is contemplated that the receiver body 56 may assume any suitable three-dimensional shape, for example, a cylinder, a cube, a sphere, a cone (including its frustum), a pyramid, and/or higher-order polygons. The rectangular prism may be particularly advantageous to maximize the container volume 58 with a lower profile when secured to the fixed surface in a manner to be described. The proportions of the walls 64-70 forming the receiver body 56 are merely exemplary and may be designed in accordance with the space constraints of its service location and/or other needs of the particular application.

Figure 5A:
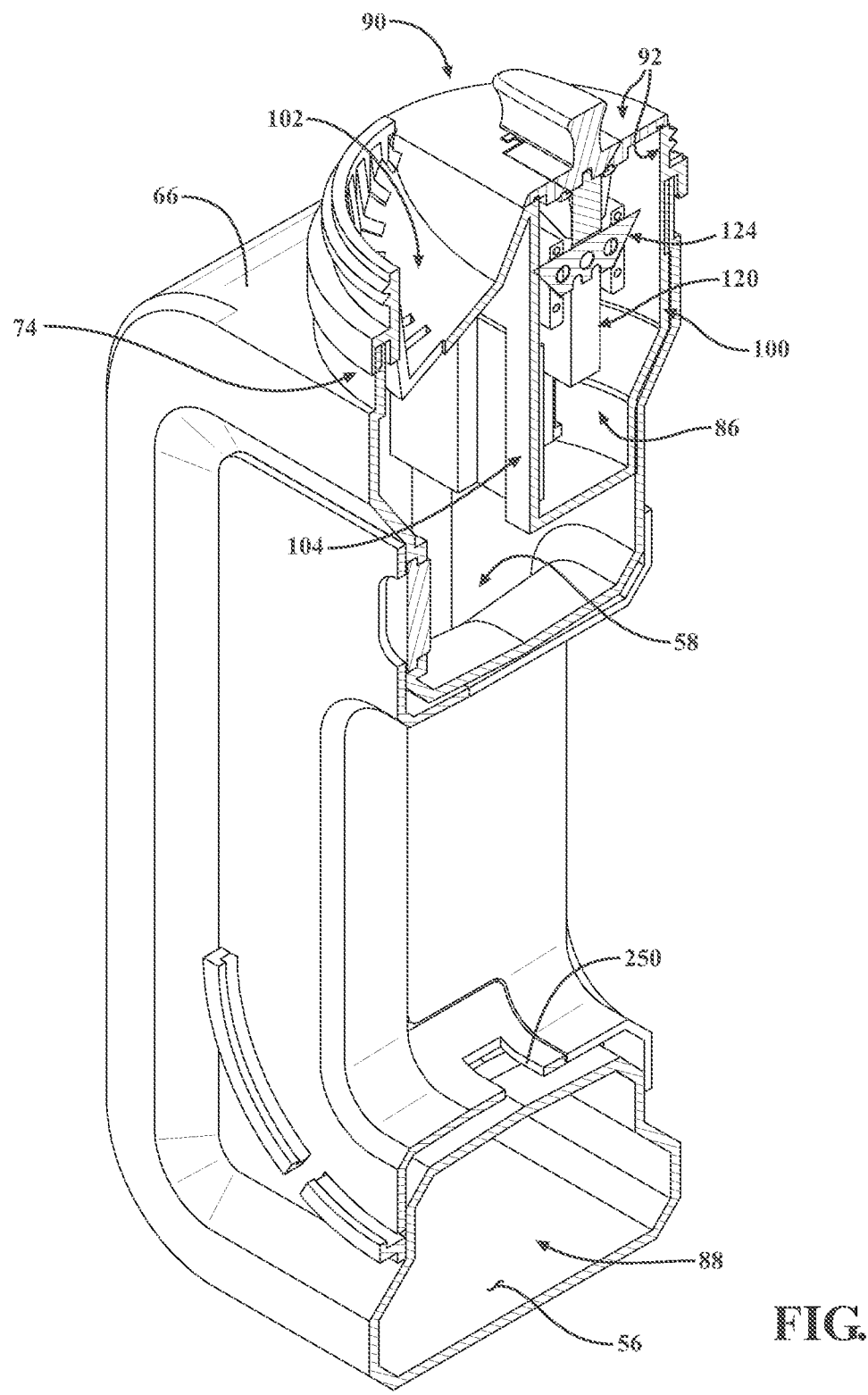
FIG. 5A is a sectional view of the waste receiver of FIG. 1 taken along section lines 5A-5A.
Figure 5B:
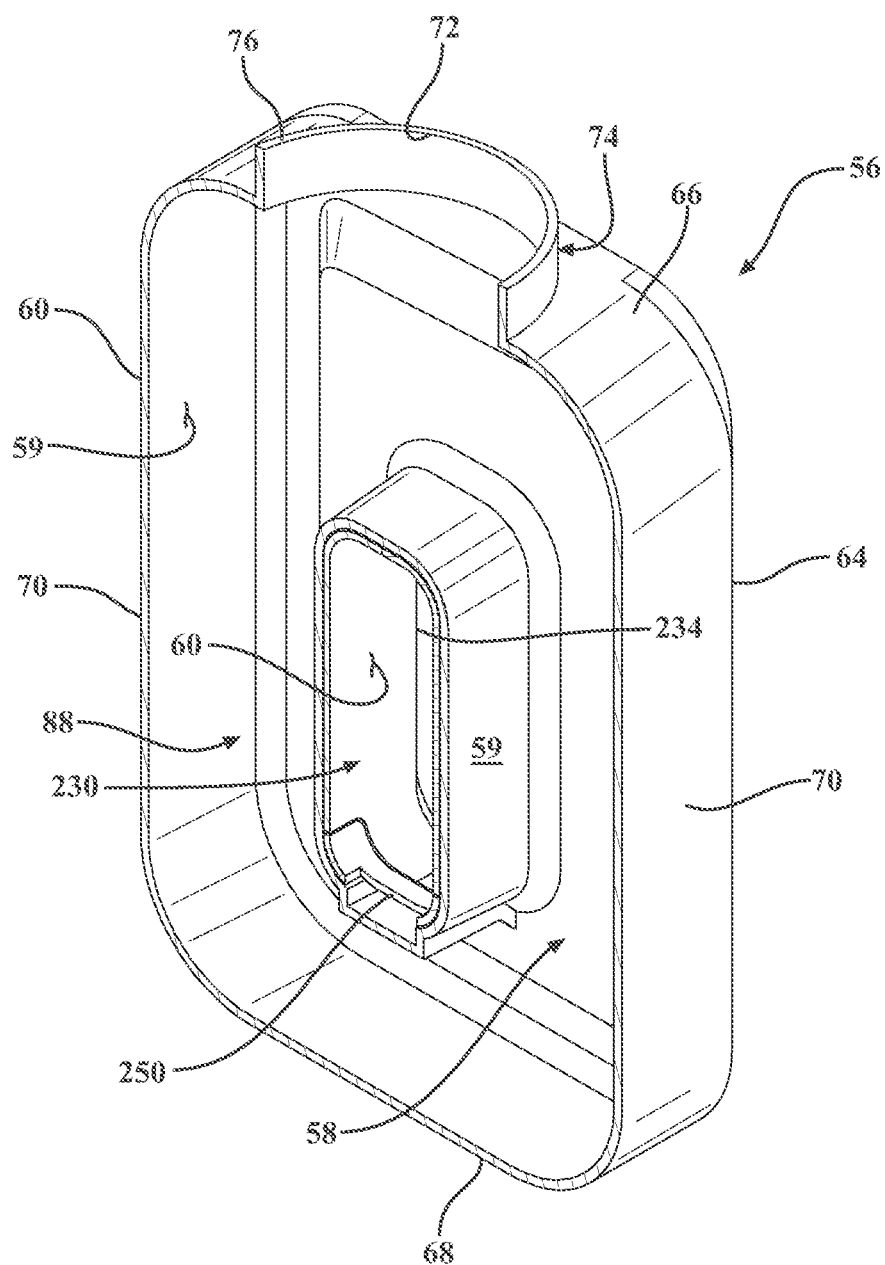
FIG. 5B is a sectional view of a receiver body of the waste receiver of FIG. 1 taken along section lines 5B-5B.
Figure 6:
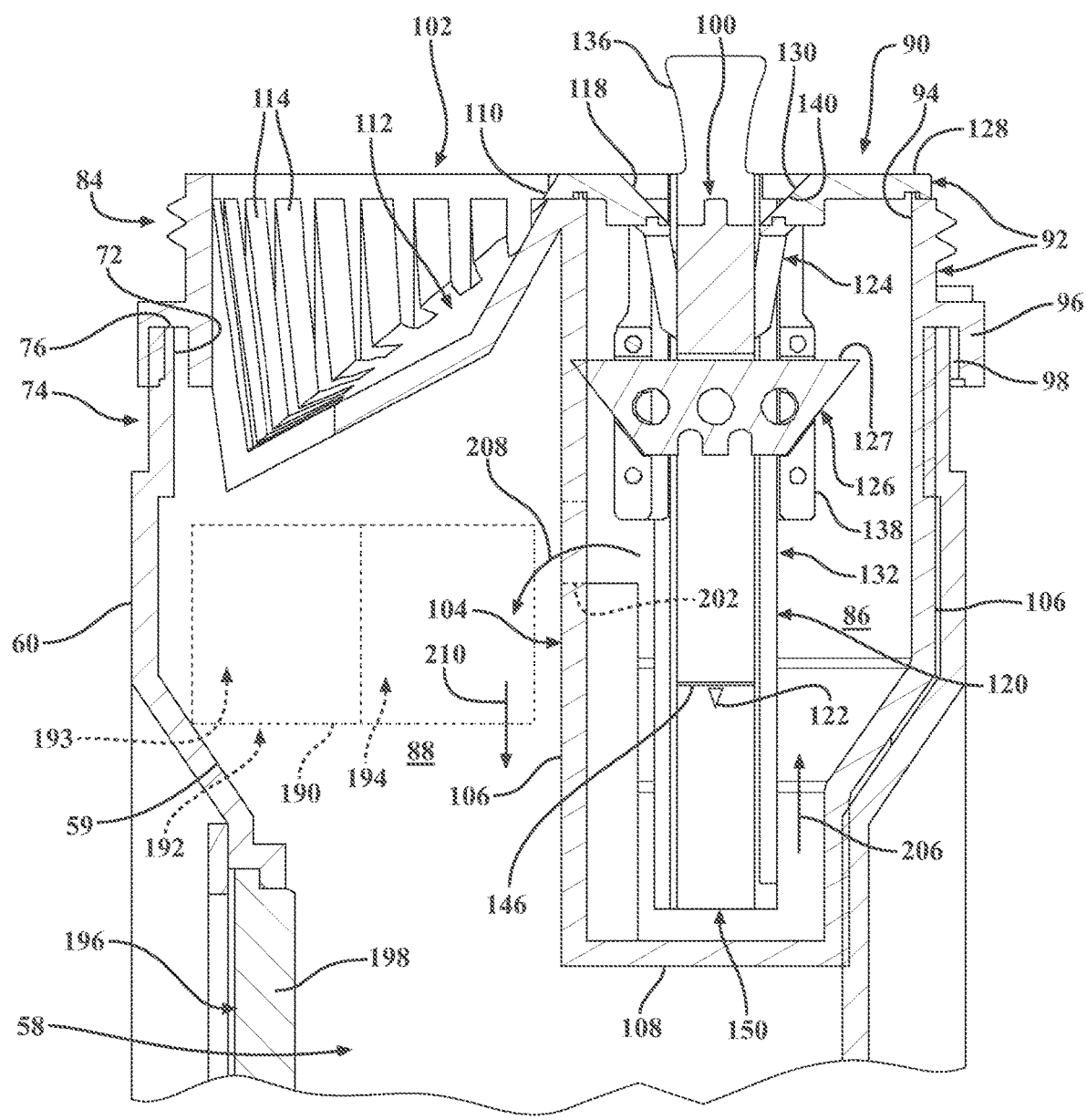
FIG. 6 is an elevation view of a portion of the sectional view of FIG. 5A including the diverter.
Figure 7:
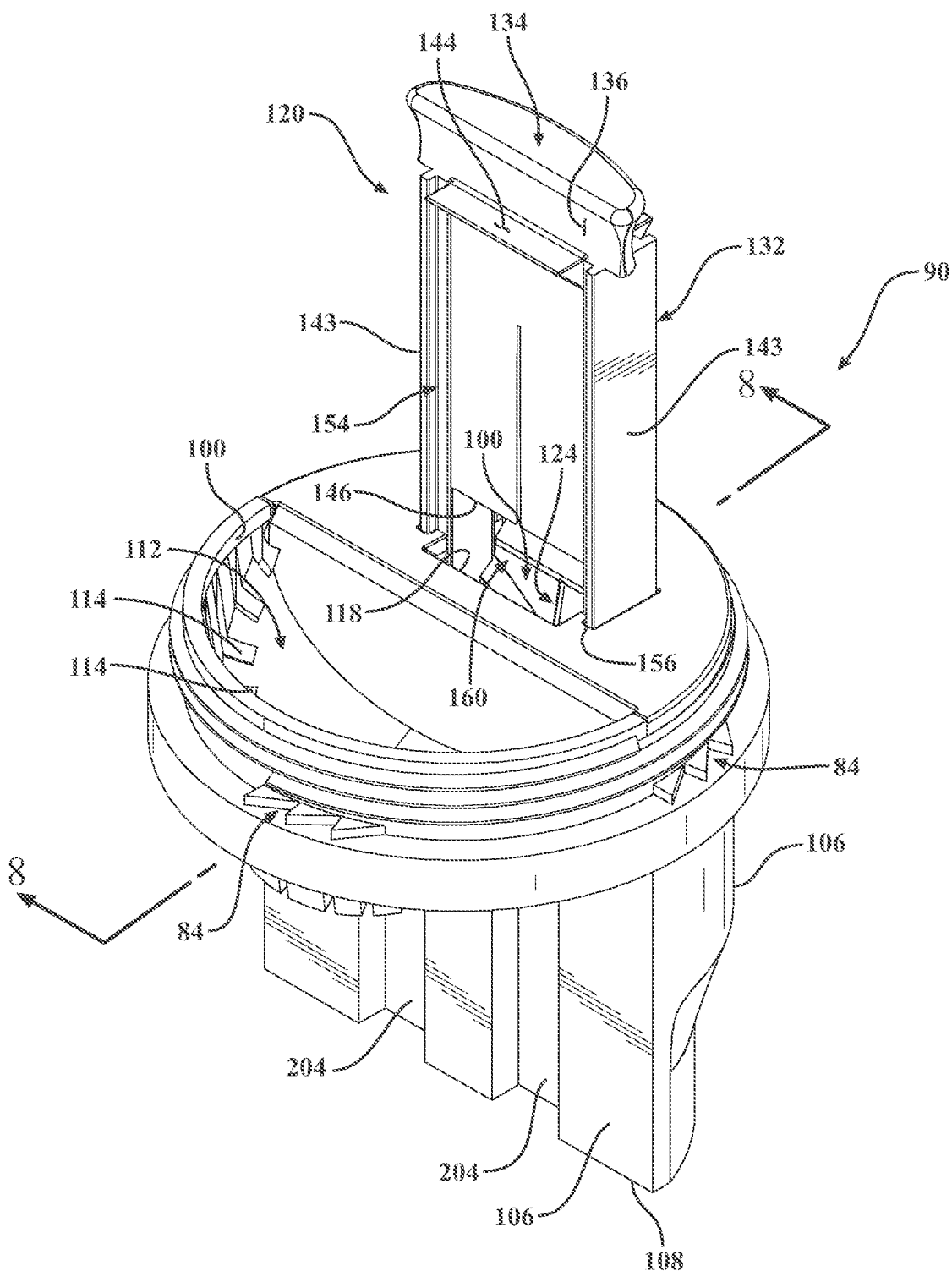
FIG. 7 is a perspective view of the diverter of FIG. 4 with a pushing member in a first position to define a window.

With concurrent reference to FIGS. 5B, 6 and 7, the receiver body 56 may define an opening 72. The receiver body 56 may include a neck 74 extending upwardly from the top wall 66. As best shown in FIGS. 5B and 6, the neck 74 terminates at a lip 76 defining the opening 72 of the receiver body 56. The neck 74 may optionally include further features to be described for facilitating safe disposal of the waste receiver 52. It is understood that the receiver body 56 may not include the neck 74, and the top wall 66 (or any of the other walls 62, 64, 68, 70) may define the opening 72. The opening 72 is in fluid communication with the container volume 58, and the opening 72 receives the pharmaceutical waste material to be disposed within the container volume 58. In other words, the pharmaceutical waste material to be deposited within the container volume 58 passes through the opening 72, even with an intermediate component such as a diverter 80 to be described positioned within the opening 72. With the opening 72 defined by the lip 76 of the neck 74, the pharmaceutical waste material passing through the opening 72 is directed to the container volume 58 under the influence of gravity.

Referring again to FIG. 1, the waste receiver 52 of the waste disposal system 50 may include a cover 82. The cover 82 couples with the receiver body 56 over the opening 72 to seal the pharmaceutical waste material within the container volume 58, and in particular prior to disposal of the waste receiver 52. With concurrent reference to FIGS. 2 and 3, the waste receiver 52 may include one or more coupling features 84 for receiving complementary coupling features (not shown) of the cover 82 in a manner that renders the waste material irretrievable. The coupling features 84 may include teeth suitably positioned on or near the neck 74 and arranged to engage complementary teeth (not shown) disposed on an underside of the cover 82. The coupling features 84 may further include threads configured to receive complementary threads (not shown) disposed on the underside of the cover 82. As best shown in FIG. 2, the teeth are shaped to permit rotation of the cover 82 relative to the receiver body 56 in a single direction. More particularly, the complementary teeth and the complementary threads of each of the cover 82 and the receiver body 56 cooperate to permit the cover 82 to rotate relative to the receiver body 56 in a first direction (R1) and prevent the cover 82 from rotating relative to the receiver body 56 in a section direction (R2) opposite the first direction. As a result, once it is desired to seal the pharmaceutical waste material within the container volume 58 prior to disposal, the cover 82 is irreversibly coupled with the receiver body 56 with the coupling features 84. After the sealing of the waste receiver 52 by a user with authorization to do so, the pharmaceutical waste material is irretrievable to those within the subsequent chain of custody of the waste receiver 52.

The waste receiver 52 may include another cover or cap 83. FIG. 1 shows the cap 83 coupled to the neck 74. The cover 83 may be coupled with the receiver body 56 at the time of assembly of the waste receiver 52. In at least some respects, the cap 83 is the same as the cover 82 previously described with the exception that the cap 83 is configured to be decoupled once the waste receiver 52 is ready to be installed at its service location. For example, the cap 83 may include the complementary threads previously described but lack the complementary teeth to engage the teeth disposed on the neck 74. As will be described in detail, the waste receiver 52 may include a chemical composition (e.g., a fluid absorber and/or a reaction agent) within the container volume 58 upon assembly and prior to shipment and installation of the waste receiver 52 at its service location. The cap 83 prevents inadvertent egress of those contents from the container volume 58 during shipment and handling of the waste receiver 52 prior to installation. It is to be appreciated that a disposable kit may be provided that includes the waste receiver 52, the cover 82, and the cap 83 in a manner shown in FIG. 1. Once the waste receiver 52 is installed at its service location, the cap 83 is decoupled from the receiver body 56 and discarded. The opening 72 remains in communication with the ambient atmosphere for receiving the pharmaceutical waste material during the operational lifecycle of the waste receiver 52. Once the waste receiver 52 is ready to be disposed, the cover 82 seals the pharmaceutical waste material within the container volume 58 of the receiver body 56 in the manner previously described.

The waste receiver 52 may advantageously accommodate disposal of both the solid phase pharmaceutical waste material and the liquid phase pharmaceutical waste material in the single receiver body 56 of substantially unitary construction. In order to properly render the pharmaceutical waste material irretrievable and/or unrecoverable, each of the solid phase pharmaceutical waste material and the liquid phase pharmaceutical waste material should undergo treatment specific to its phase. The liquid phase pharmaceutical waste material may encounter a fluid absorber 193 and/or a chemical composition 190, for example, a superabsorbent polymer (SAP) and a reaction agent 194, respectively (see FIG. 6). The solid phase pharmaceutical waste material may encounter a fluid for dissolving the same. For example, water may be added to the solid receiver guide 100 to prime the solid waste volume 86 prior to use. Known systems undesirably require more than one vessel to accommodate each of the aforementioned treatment modalities. Less sophisticated systems with a single vessel simply commingle the liquid and solid phase pharmaceutical waste material with each being treated sub-optimally, thereby increasing the likelihood of retrieval, recovery, and diversion.

Referring to FIGS. 5A and 6, the container volume 58 may be further defined by a solid waste volume 86 and a liquid waste volume 88 substantially separate from the solid waste volume 86. Each of the solid and liquid waste volumes 86, 88 are in communication with the opening 72 of the receiver body 56. As a result, the user may dispose of one or both of the solid and liquid phase pharmaceutical waste material through the single opening 72 and into the receiver body 56 with each phase of the pharmaceutical waste material to be diverted to its respective waste volume 86, 88 for suitable treatment. While a single opening 72 is shown, it is contemplated that more than one opening may be provided. For example, the neck 74 of the receiver body 56 may be divided with one or more barriers into two, three or four or more openings with each of the openings in communication with one or both of the solid and liquid waste volumes 86, 88.

The diverting or directing one or both of the solid and liquid phase pharmaceutical waste material through the opening 72 to its respective waste volume 86, 88 may be facilitated with the diverter 90 of the waste receiver 52 previously mentioned. With continued reference to FIGS. 5A and 6, the diverter 90 is coupled to the receiver body 56. In particular, the illustrated diverter 90 includes a body portion 92 having a rim 94 positioned adjacent the opening 72 of the receiver body 56. Near the rim 94, the diverter 90 has a lip 96 spaced circumferentially from the body portion 92 to define a gap 98 therebetween. The gap 98 is sized to receive the lip 76 of the receiver body 56 to effectively couple the diverter 90 with the receiver body 56. Alternatively, the lip 96 of the diverter 90 may rest atop the lip 76 of the receiver body 56 without the gap 98, or alternatively still, the diverter 90 may not include the lip 96. A joining means, for example, spin welding, adhesive, fasteners, and the like, may permanently fix the diverter 90 with the receiver body 56. In one variant, certain portions of the diverter 90 may be integrally formed with the receiver body 56 through a suitable manufacturing process, for example, injection molding, blow molding, and the like. It is noted that the receiver body 56 and/or the diverter 90 are formed from materials configured to prevent rupture, puncture, chemical degradation, and the like, with further manufacturing considerations such as per unit weight and per unit cost. Suitable materials to form the receiver body 56 and/or the diverter 90 may include durable polymers, composites, fiberglass, glass, ceramic, metal, composites, or a combination thereof. Further, the coupling features 84 of the waste receiver 52 previously mentioned may be disposed on the diverter 90. In particular, FIG. 6 shows the threads associated with the body portion 92 between the rim 94 and the lip 96. As a result, the cover 82 (or cap 83) may be coupled with the diverter 90 to seal the pharmaceutical waste material within the container volume 58.

Figure 8:
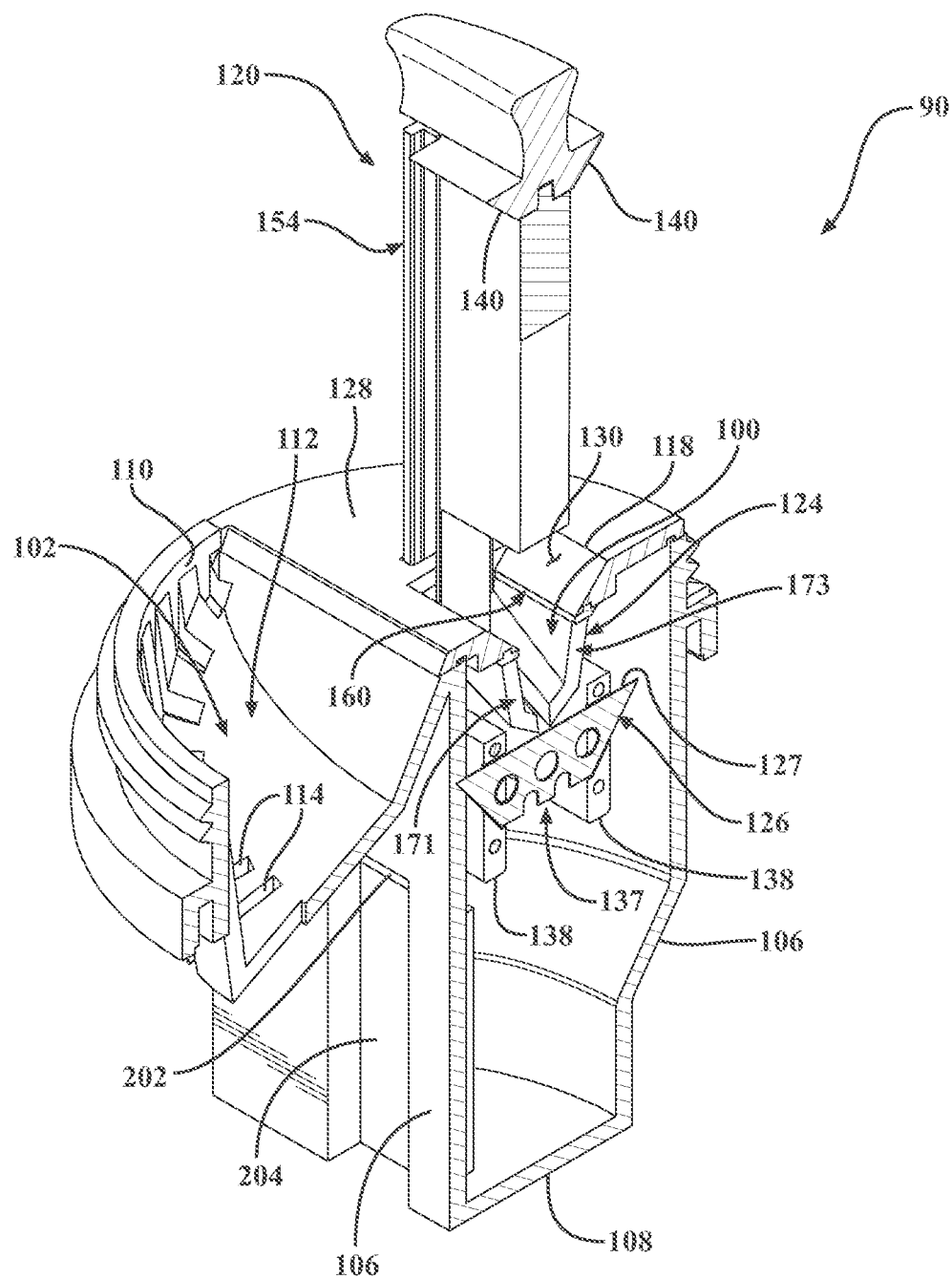
FIG. 8 is a sectional view of the diverter of FIG. 7 taken along lines 8-8.

With the diverter 90 fixed with the receiver body 56 as illustrated in FIGS. 5A and 6, the body portion 92 of the diverter 90 is at least partially disposed within the opening 72 of the receiver body 56. With further reference to FIG. 8, the diverter 90 may comprise a solid receiver guide 100 coupled to the body portion 92 and at least partially disposed within the receiver body 56. The solid receiver guide 100 is adapted to direct the solid phase pharmaceutical waste material to the solid waste volume 86. As mentioned, the solid waste volume 86 comprises a portion of the container volume 58 of the receiver body 56. The diverter 90 may further comprise a liquid receiver guide 102 also coupled to the body portion 92 and at least partially disposed within the receiver body 56. The liquid receiver guide 102 is adapted to direct the liquid phase pharmaceutical waste material to the liquid waste volume 88. The liquid waste volume 88 comprises another portion of the container volume 58 of the receiver body 56 with the liquid waste volume 88 being substantially separate from the solid waste volume 86. Each of the solid and liquid receiver guides 100, 102 of the diverter 90 are in communication with the opening 72 such that solid phase pharmaceutical waste material and liquid phase pharmaceutical waste material may be deposited in the solid and liquid receiver guides 100, 102, respectively. Likewise, when the cover 82 or the cap 83 is coupled with the diverter 90 in the manners previously described, the cover 82 or the cap 83 covers both of the solid and liquid receiver guides 100, 102 preventing the solid and liquid waste from escaping.

The solid waste volume 86 and the liquid waste volume 88 may be separated through any number of means. FIG. 6 shows a partition 104 disposed within the container volume 58 with one side of the partition 104 at least partially defining the solid waste volume 86, and the other side of the partition 104 at least partially defining the liquid waste volume 88. The partition 104 may further include several walls, including at least one sidewall 106 and a lower wall 108 that cooperate to define of an open-ended cavity that may be considered the solid waste volume 86. One of the sidewalls 106 may be contoured to the inner surface 59 of the receive body 54, as shown in FIG. 8, resulting in an arcuate shape. The other one of the sidewalls 106 may be a chord extending between ends of the arcuately-shaped sidewall 106 resulting in the solid waste volume 86 that is D-shaped when viewed in plan. It is contemplated that the partition 104 may assume any number of shapes other than that illustrated with consideration for maximizing the container volume 58 between the solid and liquid waste volumes 86, 88 therein. It is further contemplated that, in the previously mentioned variant where the diverter 90 is integrally formed with the receiver body 56, the partition 104 may be one of the structures co-molded with the receiver body 56 through the suitable manufacturing process.

With continued reference to FIGS. 5A and 6, the solid waste volume 86 may be relatively smaller than the liquid waste volume 88. It is appreciated that in certain service locations, upwards of 90% of the pharmaceutical waste material is liquid in phase. For this reason, the liquid waste volume 88 may comprise 60%, 70%, 80% or 90% or greater of the container volume 58 of the receiver body 56. For example, the liquid waste volume 88 may have a capacity of approximately 0.5, 1.0, or 1.5 or greater liters (L), and the solid waste volume 86 may have a capacity of approximately 0.2, 0.4, 0.6 or greater liters. It is understood that the relative portions between the solid and liquid waste volumes 86, 88 are merely exemplary, and the relative volume of the solid and liquid waste volumes 86, 88 may vary based on the application. Furthermore, it is recognized that the size and/or capacity of the waste receiver 52 may be commensurate with the purpose and/or service location of the waste disposal system 50.

The liquid receiver guide 102 may be any suitable structure for directing the liquid phase pharmaceutical waste material to the liquid waste volume 88. Referring to FIGS. 5A and 8, the liquid receiver guide 102 includes an inlet 110 defining an uppermost aspect of the liquid receiver guide 102. A funnel-type device 112 may be provided to define the inlet 110, or the device may be coupled to an intermediate structure defining the inlet 110. The funnel-type device 112 includes at least one orifice 114 for the liquid phase pharmaceutical waste material to pass through to the liquid waste volume 88. The orifices 114 may include a plurality of slots arcuately spaced about the funnel-type device 112. The orifices 114 of the liquid receiver guide 102 are sized to not only to inhibit or prevent retrieval of the liquid phase pharmaceutical waste material from within the liquid waste volume 88 by impeding tools from entering the liquid waste volume 88, but also impede ingress of the solid phase pharmaceutical waste material to the liquid waste volume 88. However, other orifice designs are also contemplated.

The solid receiver guide 100 directs the solid phase pharmaceutical waste material to the solid waste volume 86, as mentioned, and more particularly in a manner that facilitates the solid phase pharmaceutical waste material being irretrievable and/or unrecoverable. The solid receiver guide 100 may include one or more of an inlet 118, a pushing member 120, a gripping member 122, a funnel member 124, and a cutting element 126 with each to be described in further detail.

Figure 4:
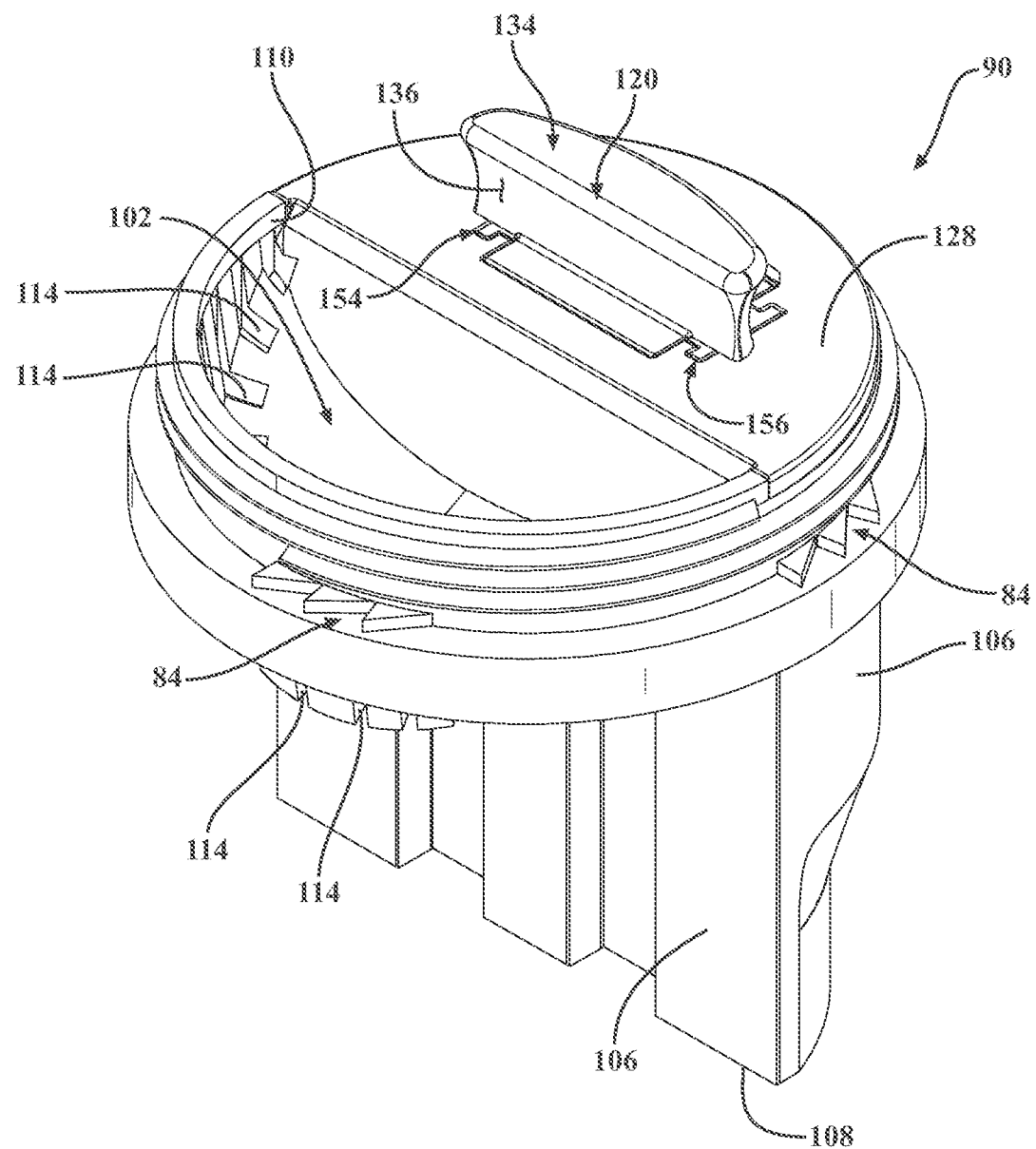
FIG. 4 is a perspective view of a diverter.

Referring to FIGS. 4 and 6, the body portion 92 of the diverter 90 may include an upper wall 128 coupled to the rim 94. The upper wall 128 is D-shaped and complementary to the counterposing D-shaped void at least partially defining the inlet 110 of the liquid receiver guide 102. The complementary shapes of the upper wall 128 of the solid receiver guide 100 and the inlet 110 of the liquid receiver guide 102 permit each of the solid and liquid pharmaceutical waste material to be deposited through the opening 72 that is circular and conveniently shaped for receiving the cover 82 of simple geometry. A medial aspect of the upper wall 128 is arranged to be generally aligned with one of the sidewalls 106 comprising the partition 104. As a result, the sidewalls 106, the bottom wall 108, and the upper wall 128 may enclose the solid waste volume 86 with the exception of the inlet 118 and an orifice 202 to be described. In other words, the liquid waste volume may be separated from the solid waste volume except for the orifice 202.

The inlet 118 of the solid receiver guide 100 may be rectangular in shape and sized to receive the solid phase pharmaceutical material including, among other objects, patches and pills. As best shown in FIGS. 6 and 8, the upper wall 128 may optionally include at least one inclined surface 130 that may partially define the inlet 118. The inclined surfaces 130 function to guide the solid phase pharmaceutical material towards the funnel member 124 to be further described. Further, the tapering from the inlet 118 to the funnel member 124 with the inclined surfaces 130 prevents retrieval of the solid phase pharmaceutical waste material from within the solid waste volume 86 by impeding tools from entering the solid receiver guide 100.

Figure 9:
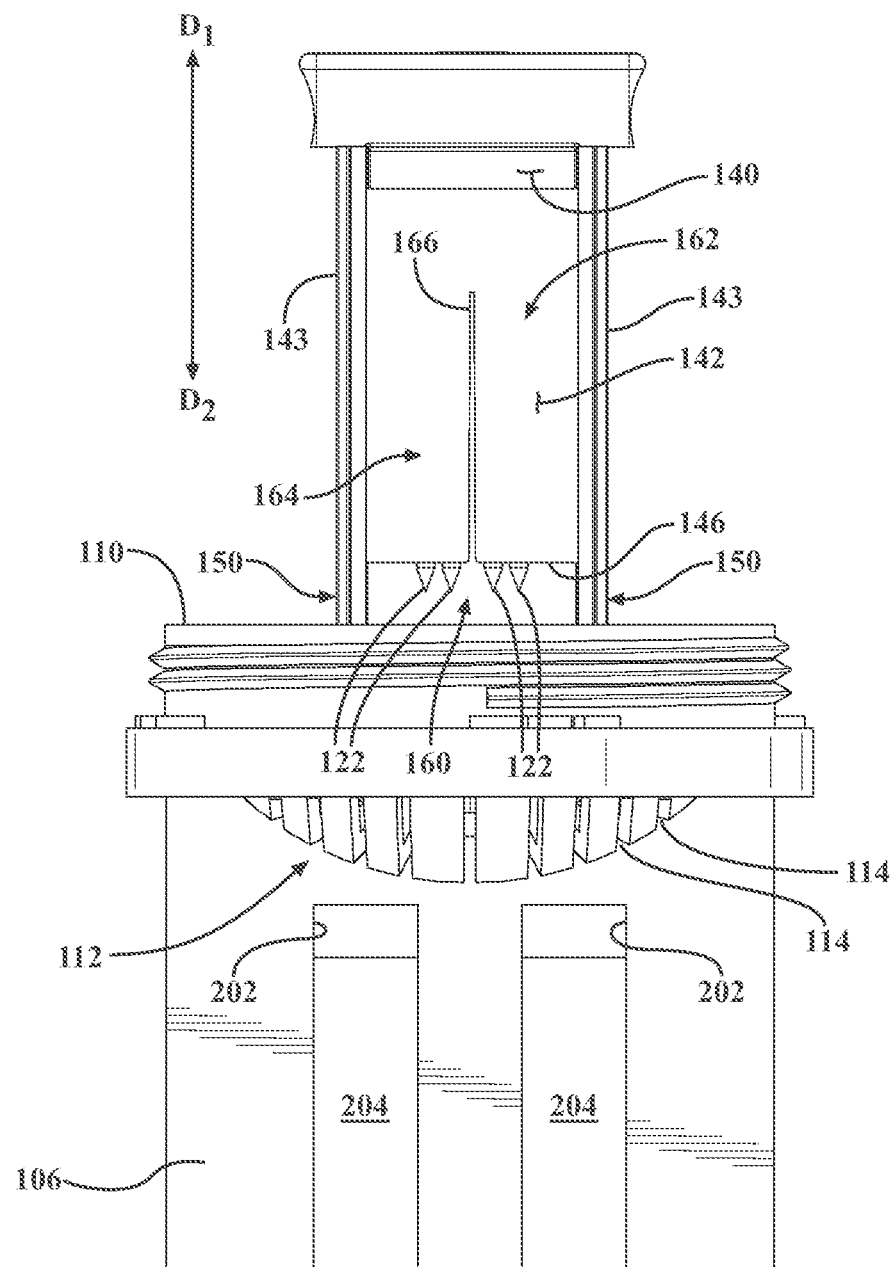
FIG. 9 is an elevation view of the diverter of FIG. 7.
Figure 10:
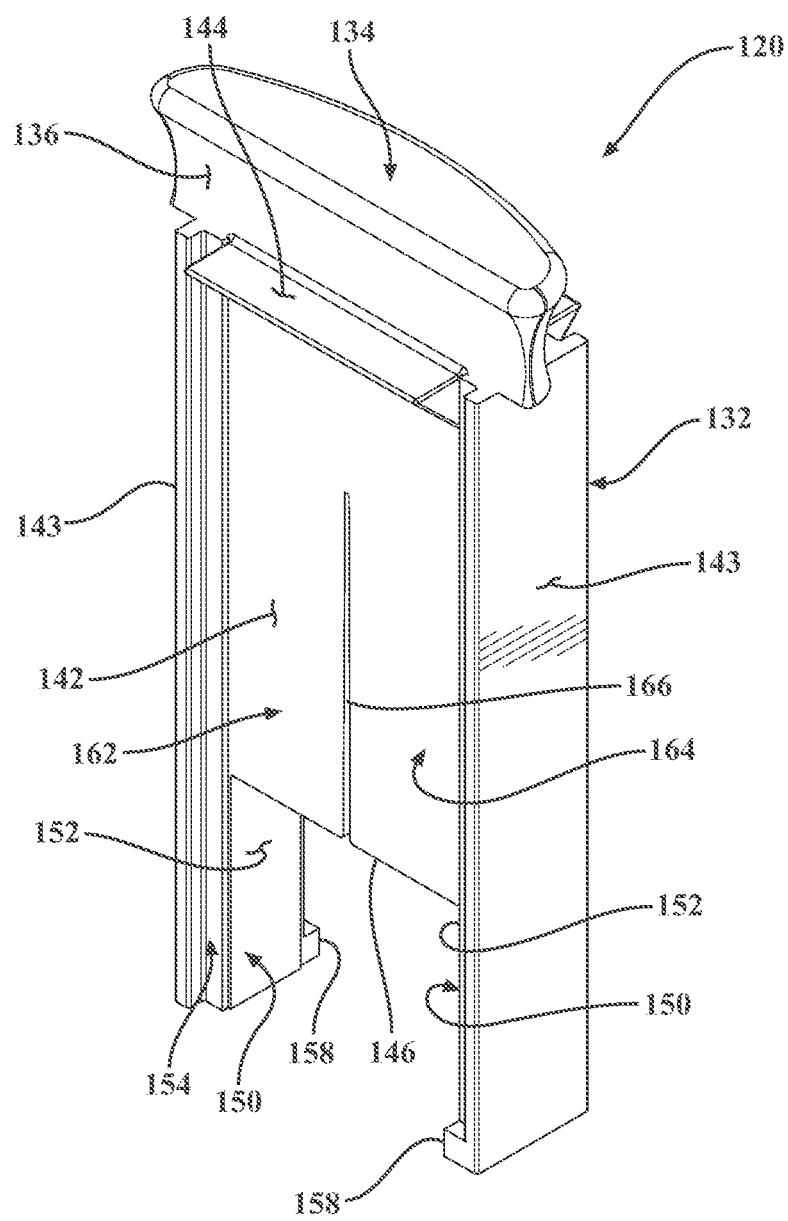
FIG. 10 is a perspective view of the pushing member.

With concurrent reference to FIGS. 9 and 10, the pushing member 120 is movably disposed relative to the solid receiver guide 100. The pushing member 120 is adapted to receive an input from a user to move the solid phase pharmaceutical waste material through the solid receiver guide 100. The pushing member 120 includes a main body 132 defining a grip or handle 134. The handle 134 includes control surface 136 adapted to receive the input from the user to move the pushing member 120 relative to the solid receiver guide 100. The handle 134 may extend above the upper wall 128 of the body portion 92 of the diverter 90 when the pushing member 120 is in a second position to be described (see FIGS. 5A and 6). The control surface 136 may be arranged to be manipulated by the user, for example pinched, to provide the input to the pushing member 120. The main body 132 may include at least one inclined surface 140 complementary to the inclined surface 130 of the upper wall 128. The complementary inclined surfaces 130, 140 are arranged to abut one another when the pushing member 120 is in the second position. In other words, the inclined surfaces 130 of the upper wall 128 directly contacts the inclined surfaces 140 of the main body 132 to prevent the pushing member 120 from being further advanced downwardly into the solid receiver guide 100. With the complementary inclined surfaces 130, 140 in direct contact and the pushing member 120 in the second position, a portion of the handle 134 is flush with the upper wall 128 for aesthetics and selectively preventing access to the solid receiver guide 100.

The main body 132 may be generally sized approximate the inlet 118 and a channel 137 defined by the upper wall 128 and the opposing barriers 138 of the solid receiver guide 100, as best shown in FIGS. 6 and 8. The main body 132 is substantially rectangular when viewed in plan. In particular, the main body 132 may include a first pair of opposing side surfaces 142, a second pair of opposing side surfaces 143, an upper surface 144 generally defining an interface between the main body 132 and the handle 134, and a lower surface 146 opposite the upper surface 144. Of course, the main body 132 may have other suitable shapes. As will be described in greater detail, the lower surface 146, or components thereon, is the structure that directly contacts the solid phase pharmaceutical waste material to move the solid phase pharmaceutical waste material through the solid receiver guide 100.

As best shown in FIGS. 7-10, the pushing member 120 may include a leg 150 extending from the main body 132 with two legs shown. The legs 150 may generally extend from the lower surface 146 of the main body 132 in a direction opposite the handle 134. Each of the legs 150 may be at least partially defined by a portion of one of the side surfaces 142 of the main body 132, and an inner leg surface 152 opposite the portion of the side surface 142. The pushing member 120 may further include track features 154 extending along the main body 132 and at least partially defining the side surfaces 143. Each of the track features 154 engage a complimentary rail feature 156 within the channel 137 of the upper wall 128 of the body portion 92. FIGS. 4 and 7 best show the rail features 156 positioned opposite the inlet 118 and opening into the inlet 118. The track features 154 extend from the main body 132 and sized in a manner to be slidably and snugly received within the rail features 156 to facilitate smooth movement of the pushing member 120. The pushing member 120 may further include a foot 158 extending from the leg 142 with two feet shown. The feet 158 prevent complete removal of the pushing member 120 from the solid receiver guide 100. When the pushing member 120 is in the second position and at a maximum, the feet 158 interfere with a complimentary structure of the solid receiver guide 100 to prevent further retraction. The aforementioned structures of the pushing member 120 may be of unitary construction and formed from a durable plastic or other suitable materials.

As mentioned, the pushing member 120 is movable to the second position illustrated in FIGS. 5A and 6, and is further movable to a first position illustrated in FIGS. 7-9. In the first position, the main body 132 is spaced from the solid receiver guide 100 to provide a window 160 at least partially defined between the main body 132, the legs 142, and the solid receiver guide 100. With particular reference to FIGS. 7-9, moving the pushing member 120 to the first position exposes the inlet 118 of the solid receiver guide 100 and provides the window 160 for receiving the solid phase pharmaceutical waste material. To move the pushing member 120 to the first position, the input is provided to the control surface 136 of the handle 134 with the input being a linear force in a first direction (D1), which may be generally upwardly relative to the diverter 90. The main body 132 of the pushing member 120 slidably moves within the channel 137 and through the inlet 118 of the solid receiver guide 100. The motion may continue until at least the lower surface 146 of the main body 132 exits the solid receiver guide 100 and is positioned above the upper wall 128 of the body portion 92 of the diverter 90. The void between the lower surface 146 and the inlet 118 may be considered to bound the window 160 on the upper and lower sides, respectively. The legs 142 of the pushing member 120 may bound the window 160 laterally. At least a portion of the legs 142 may remain within the solid waste volume 86 when the pushing member 120 is in the first position. With the window 160 exposing the inlet 118 of the solid receiver guide 110, the user deposits the solid pharmaceutical waste material within or near the inlet 118. In other configurations, the legs are optional and the pushing member may be removable from the container.

The pushing member 120 is moved from the first position to the second position to facilitate moving of the solid phase pharmaceutical waste material through the solid receiver guide 100. To move the pushing member 120 from the first position to the second position, another input is provided to the control surface 136 of the handle 134 with the input being a linear force in a second direction (D2) opposite the first direction. The second direction may be generally downwardly or towards the diverter 90. The complementary track features 154 slidably and snugly move relative to the rail features 156 to facilitate smooth movement of the pushing member 120. Other track features are contemplated, such as rolling members or bearings.

The main body 132 of the pushing member 120 slidably moves towards the inlet 118 in which the solid pharmaceutical waste material has previously been deposited. The solid pharmaceutical waste material interferes with the lower surface 146 of the main body 132 passing through the inlet 118 of the solid receiver guide 100. The lower surface 146 urges the solid pharmaceutical waste material through the inlet 118 and into the channel 137. The inclined surfaces 130 of the upper wall 128 may cooperate to ensure the solid phase pharmaceutical waste material does not inadvertently escape the bounds of the inlet 118 upon coming into contact with the lower surface 146 of the pushing member 120 being moved in the second direction. The motion may continue until at least the inclined surfaces 140 of the pushing member 120 are in direct contact with the inclined surfaces 130 of the diverter 90, at which point the window 160 no longer is present and the pushing member 120 has returned to the first position. As the pushing member 120 moves from the second position to the first position, the lower surface 146 of the pushing member 120 moves through the channel 137 to be situated beneath the barriers 138 within the solid waste volume 86. As a result, the solid phase pharmaceutical waste material is likewise directed into the solid waste volume 86 containing a fluid to be later described with the fluid at least partially dissolving active medicine associated with the solid phase pharmaceutical waste material such that a residual liquid may become disposed on the end of the pushing member 120.

As previously mentioned, solid phase pharmaceutical waste material of particular interest are patches and pills, and the waste receiver 52 advantageously includes features to facilitate treating the patches and pills in a manner that renders them irretrievable and/or unrecoverable. In particular, it is known that used patches contain unused medicine and unused pills obviously contain unused medicine, including narcotics. Those seeking to engage in drug diversion may attempt to retrieve the patches and pills, and recover the narcotics from the same. Known systems that include a fluid for dissolving the unused medicine on the patch and/or the unused pills may be deficient in several respects, at least one of which is the time required for the fluid to suitably penetrate the patch and the pill to dissolve the unused medicine.

Referring now to FIGS. 5A, 6 and 8, the waste receiver 52 may include the cutting element 126, for example a blade, coupled to the solid receiver guide 100. The cutting element 126 is disposed within the solid waste volume 86 and positioned to cut the solid phase pharmaceutical waste material. In particular, the cutting element 126 is adapted to at least score a patch or a pill upon insertion of the patch or the pill through the solid receiver guide 100. As used herein, "scoring" includes engaging the patch or the pill with an edge 127 of the cutting element 126. The scoring of the patch or the pill exposes a greater surface area of the patch or the pill for more thorough processing of the solid phase pharmaceutical waste material in manners to be described. In certain cases, the scoring of the patch or pill damages a barrier that would otherwise prevent rapid deactivation of the pharmaceutical waste. With respect to the pill, the barrier may be a coating or capsule. With respect to the patch, the barrier may be a layer of the patch. The cutting element 126 may take any suitable form, such as the blade, rotating cutting device, cutting wheels, etc. The use of the blade, such as a razor blade, results in a low-cost and effective option suitable for a disposable assembly. The cutting element 126 may be statically mounted or movable linearly relative to the waste receiver 52 and/or be free of any motorized components, again, in the aim of simplicity and cost-reduction. The cutting element 126 may consist of a single cutting edge.

The inlet 118 of the solid receiver guide 100 is preferably sized to permit insertion of patches and pills without excess clearance so as to limit the extent to which the items may be retrieved. The cutting element 126 is spaced below the inlet 118 of the solid receiver guide 100 by a suitable distance such that a person is not injured should he or she attempt to urge the patch downwardly along the solid receiver guide 100 without the use of the pushing member 120. The cutting element 126 may be coupled to the solid receiver guide 100 through riveting, interference fit, adhesives, and other joining means. As best shown in FIGS. 6 and 8, the cutting element 126 is coupled to the barriers 138 disposed within the solid waste volume 86 and defining the channel 137. In particular, the barriers 138 each comprise opposing portions coupled together with pins with the cutting element 126 sandwiched between the opposing portions. In one configuration, the cutting element 126 is oriented such that the edge 127 of the cutting element 126 is oriented towards the inlet 118 of the solid receiver guide 100 such that the solid phase pharmaceutical waste material being moved through the solid receiver guide 100 initially encounters the edge 127 before passing the cutting element 126.

Figure 11:
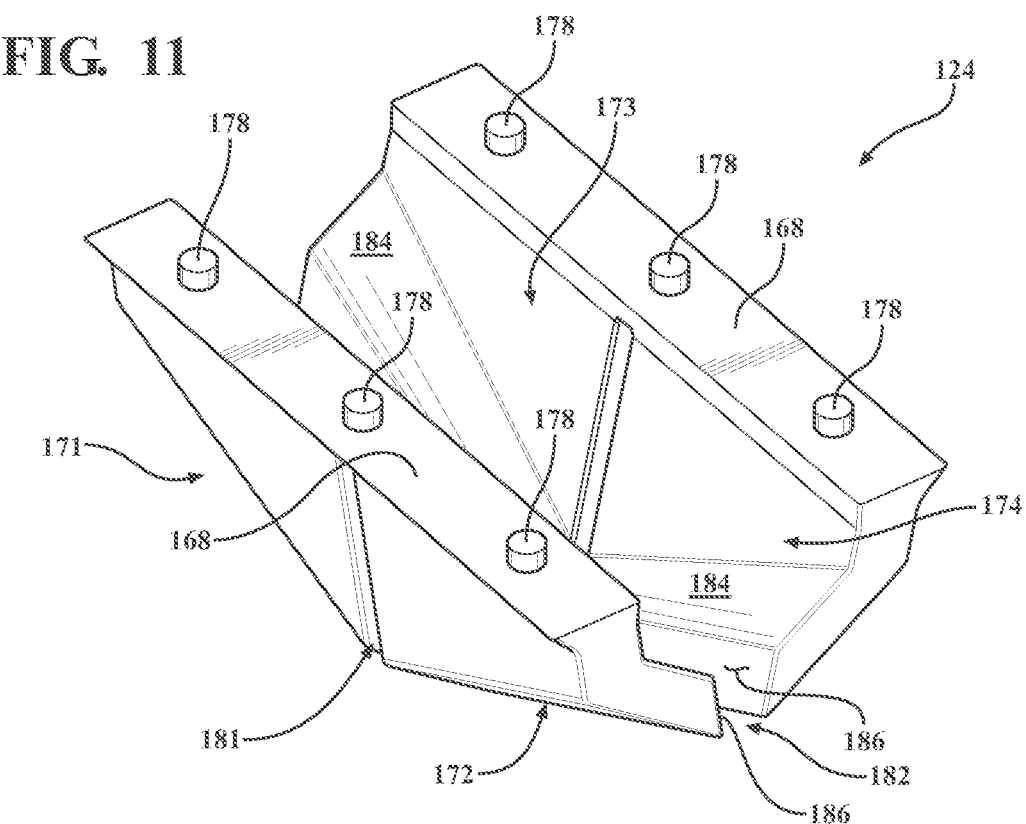
FIG. 11 is a perspective view of a funnel member.

As explained, the pushing member 120 moves the solid phase pharmaceutical waste material through the solid receiver guide 100, and the cutting element 126 at least scores the solid phase pharmaceutical waste material being moved through the solid receiver guide 100. The waste receiver 52 includes further features to increase the likelihood that the solid phase pharmaceutical waste material being moved through the solid receiver guide 100 properly encounters the edge 127 of the cutting element 126. With reference to FIGS. 9 and 11, the main body 132 of the pushing member 120 includes a first portion 162 and a second portion 164 spaced apart from the first portion 162 to define a slot 166 therebetween. The slot 166 may extend upwardly from the lower surface 146 of the main body 132 such that, when the pushing member 120 is in the first position, the slot 166 is in communication with the window 160. The slot 166 is sized to receive the cutting element 126 as the pushing member 120 moves from the first position to the second position. In other words, with the cutting element 126 received within the slot 166, the cutting element 126 is positioned between the first and second portions 162, 164 of the main body 132 and above the lower surface 146. Among other advantages, receiving the cutting element 126 within the slot 166 permits the pushing member 120 to be inserted into a greater distance within the solid receiver guide 100 (i.e., without obstruction from the cutting element 126).

The inlet 118 of the solid receiver guide 100 may be elongate (e.g., rectangular in accordance with dimensions of a cross section of most patches) with the cutting element 126 oriented substantially perpendicular to the inlet 118. For example, when viewed in plan, the body of the cutting element 126 may be oriented horizontally with the inlet 118 of the solid receiver guide 100 oriented vertically. The cutting element 126 may be positioned approximately midway between opposing ends of the inlet 118, and the slot 166 is spaced equidistant from the opposing sides 143 and in alignment with the edge 127 of the cutting element 126. As the pushing member 120 is moved from the first position to the second position to move the patch through the solid receiver guide 100, the edge 127 of the cutting element 126 encounters the patch and the patch is "pinched" between the edge 127 of the cutting element 126 and the lowermost aspect of the slot 166, thereby increasing the likelihood the patch is scored in a suitable manner. Further, with the slot 166 receiving the cutting element 126, the patch is urged further within the solid receiver guide 100, thereby increasing the likelihood that the patch appropriately descends further into the solid waste volume 86. It is further contemplated that the cutting element 126 may be provided in singular as shown, or two, three or four or more blades may be provided in a parallel, angled, or perpendicular fashion.

The inherent flexibility of patches is associated with the possibility that the patch positioned within the window 160 with the pushing member 120 in the first position may become contorted or at least partially "eject" from the window 160 as the pushing member 120 is moved from the first position to the second position. For example, if a square-shaped patch is rested upon the upper wall 128 of the diverter 90 to be bifurcated by the lower surface 146 of the main body 132, as the pushing member 120 is moved towards the second position, the patch may favor one side of the main body 132 and not be properly moved through the solid receiver guide 100. To avoid the aforementioned undesirable result, the pushing member 120 may include the gripping member 122 adapted to engage the patch. As best shown in FIGS. 6 and 9, the gripping member 122 is coupled to the main body 132, and more particularly to the lower surface 146 of the main body 132. The gripping member 122 may be a spike tapering to a point configured to penetratingly engage the patch typically comprised of a woven fabric or permeable layer. More than one gripping member 122 may be provided such as the four spikes shown in FIG. 9. Two of the spikes are coupled to the first portion 162 of the main body 132, and another two of the spikes are coupled to the second portion 164 of the main body 132. As a result, as the pushing member 120 is moved from the first position to the second position, the gripping member(s) 122 engage the patch prior to the patch engaging the lower surface 146. Lateral movement of the patch relative to the pushing member 120 is eliminated or limited such that the patch remains as initially positioned relative to the main body 132 as the pushing member 120 continues through the inlet 118 of the solid receiver guide 100 and receives the cutting element 126 within the slot 166. In other words, the gripping member 122, the cutting element 126, and the slot 166 cooperate to ensure the patch is at least partially scored as it is moved through the solid receiver guide 100 into the solid waste volume 86.

Whereas the patches typically have a size and shape to be scored relatively easily by the cutting element 126 when properly moved through the solid receiver guide 100, it is readily appreciated that the scoring of pills is associated with additional challenges based on their size and shape. The challenges may be particularly pronounced with the cutting element 126 being a blade with a singular edge. The waste receiver 52 overcomes at least the aforementioned challenge with the funnel member 124 previously mentioned. With reference to FIGS. 6 and 8, the funnel member 124 may be disposed in the solid waste volume 86 between the inlet 118 and the cutting element 126. In particular, the funnel member 124 may be coupled to an interior surface of the upper wall 128 of the diverter 90.

Figure 12:
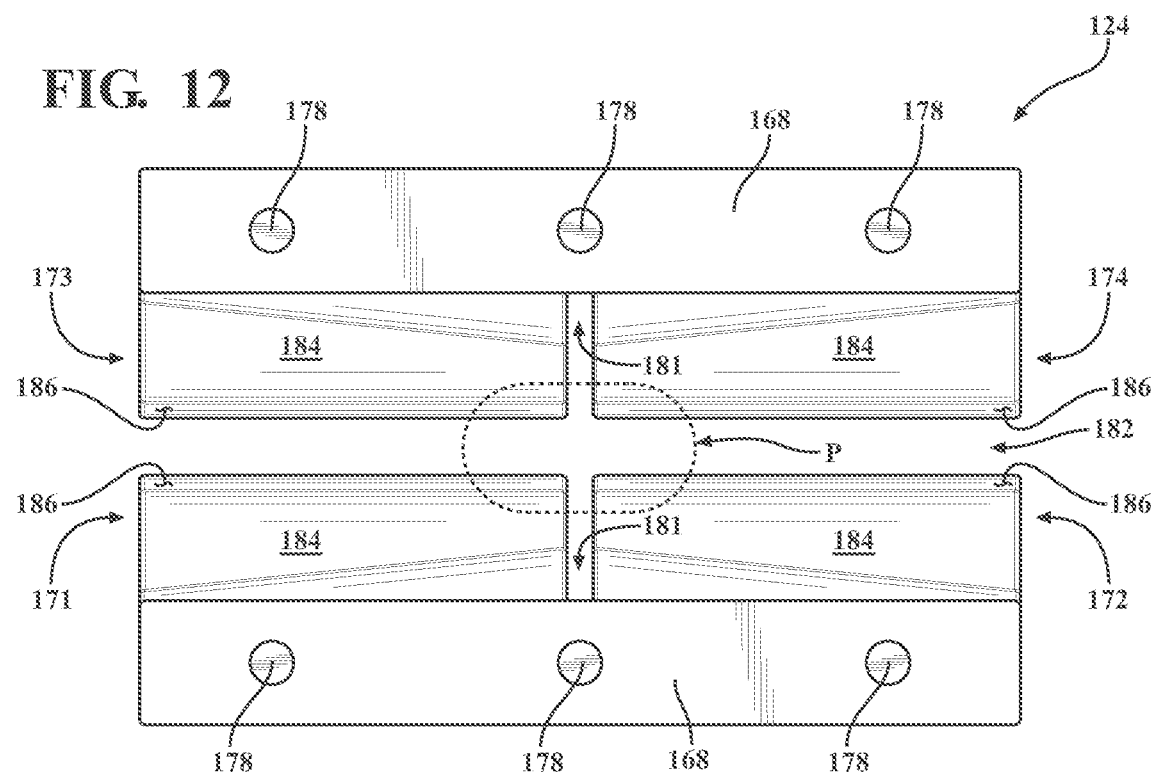
FIG. 12 is a plan view of the funnel member of FIG. 11.

FIGS. 11 and 12 show a perspective and a plan view, respectively, of the funnel member 124. The funnel member 124 may include at least one frame element 168 and a plurality of sections 171, 172, 173, 174 coupled to the frame element 168 (also referred to herein as a first section 171, a second section 172, a third section 173, and a fourth section 174). The frame element 168 includes two elongate plates with posts 178 disposed on one surface of the frame element 168 and the sections 171-174 disposed on the opposite surface of the frame element 168. The posts 178 are received within complementary voids of the interior surface of the upper wall 128 to couple the funnel member 124 with the upper wall 128. FIGS. 11 and 12 further show two of the sections 171-174 coupled to each of the frame elements 168. Other configurations of the frame elements 168 are also contemplated. Alternatively, the plurality of sections may be directly coupled to the solid waste guide.

Figure 14:
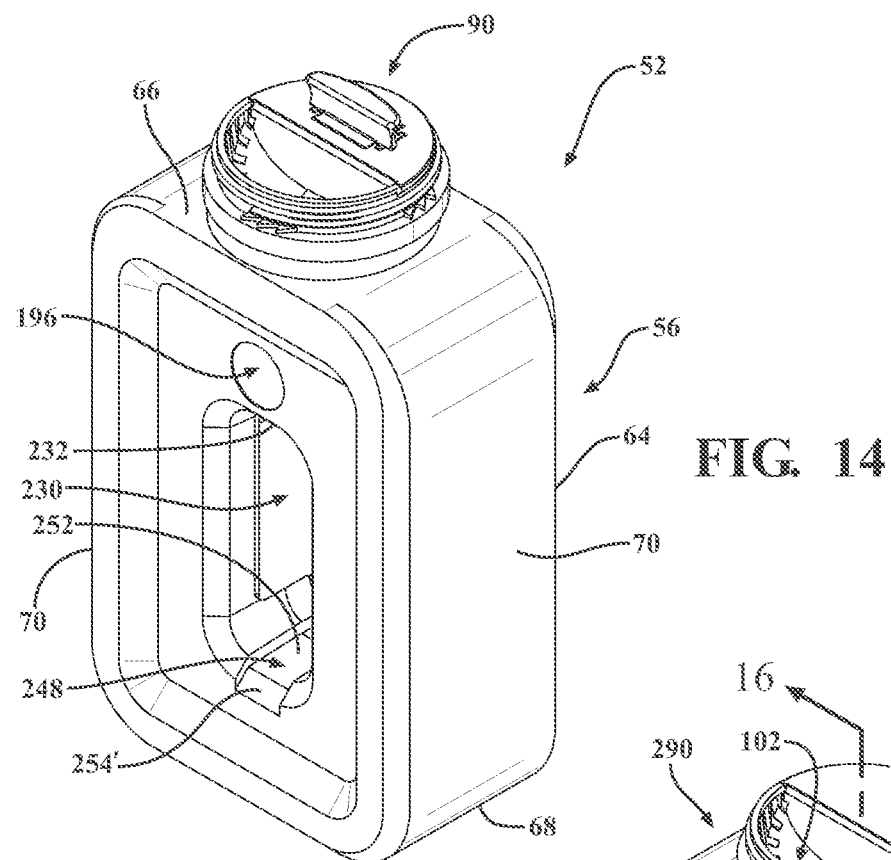
FIG. 14 is a perspective view of the waste receiver of FIG. 1 with a front wall removed to show features of a lock passageway.

The sections 171-174 are positioned to define a first gap 181 and a second gap 182. In particular, the first and second sections 171, 172 are spaced apart from one another to define the first gap 181, or at least a portion thereof; the third and fourth sections 173, 174 are spaced apart from one another to further define the first gap 181, or at least a portion thereof; the first and third sections 171, 173 are spaced apart from one another to define the second gap 182, or at least a portion thereof; and, the second and fourth sections 172, 174 are spaced apart from one another to further define the second gap 182, or at least a portion thereof. FIG. 14 shows the funnel member 124 being symmetric about each of the first and second gaps 181, 182 and the first and second gaps 181, 182 being perpendicular to one another. The first and second gaps 181, 182 may be sized to be at least slightly smaller than at least some pills such that the pill(s) deposited through the inlet 118 of the solid receiver guide 100 are supported on at least two of the sections 171-174. The pill(s) remain situated on the funnel member 124 until urged through the first and second gaps 181, 182 with the pushing member 120 in a manner to be described.

As best shown in FIG. 8, the first gap 181 is positioned above the cutting element 126, and more particularly, the edge 127 of the cutting element 126. In other words, if the cutting element 126 is the blade, the first gap 181 and the cutting element 126 may be considered aligned with each other with the cutting element 126 positioned beneath the funnel member 124 relative the upper wall 128. In other words, the edge 127 of the cutting element 126 may be centered within the first gap 181. Further, the first gap 181 is vertically aligned with the slot 166 of the pushing member 120. Each of the sections 171-174 may include an inclined surface 184 oriented towards one another to define a cavity or funnel-type shape of the funnel member 124. The inclined surfaces 184 are oriented towards the first gap 181, and preferably oriented towards the second gap 182, as best shown in the perspective view of FIG. 13. As a result, when a pill is deposited through the inlet 118 of the solid receiver guide 100 with the pushing member 120 in the first position, the pill descends into contact with the funnel member 124 under the influence of gravity. The inclined surfaces 184 guide the pill (P) to be supported above the first gap 181, and preferably above the second gap 182, as best shown in FIG. 12. In other words, when the pill is supported above the first and second gaps 181, 182, each of the sections 171-174 may support a portion of the pill. As the pushing member 120 is moved from the first position to the second position, the lower surface 146 of the main body 132 urges the pill through the funnel member 124 and into engagement with the edge 127 of the cutting element 126. With the cutting element 126 below and sufficiently near the first gap 181, the likelihood that the pill does not engage the edge 127 of the cutting element 126 is minimized. The edge 127 of the cutting element 126 at least partially scores the pill, which then further descends within the solid waste volume 86 under the influence of gravity (or further moved with the pushing member 120). With the pill suitably scored and perhaps sliced, the fluid within the solid waste volume 86 more likely comes into contact with the active medicine of the pill (i.e., beneath the coating, within the capsule, etc.).

As mentioned, the first and second gaps 181, 182 may be sized to be at least slightly smaller than at least some pills, yet the pushing member 120 moves the pill through the funnel member 124 and into engagement with the cutting element 126. To facilitate this unique functionality, each of the sections 171-174 may be formed from flexible and resilient material suitable for deflecting when subjected to more than minimal forces. As a result, as the pushing member 120 moves the pill through the first and second gaps 181, 182, the sections 171-174 deflect to provide suitable clearance for the pill to pass through the first and second gaps 181, 182. The second gap 182 is also sized to be at least slightly smaller than the main body 132 of the pushing member 120. As a result, as the pushing member 120 moves through the second gap 182 of the funnel member 124, the sections 171-174 deflect away from the main body 132 to provide suitable clearance for the main body 132 to pass through the first and second gaps 181, 182. In one example, the first and third sections 171, 173 deflect away from one another, and the second and fourth sections 172, 174 deflect away from one another. In such an example, a size of the first gap 181 (e.g., spacing between the first and second sections 171, 172 and the third and fourth sections 173, 174) may remain unchanged. The precise motion of the deflection may be based, at least in part, on the manner in which the sections 171-174 are coupled to the frame elements 168. It is understood that the funnel member 124 including four sections is merely exemplary, and in variants the funnel member 124 may include two, three, five, six or seven or more sections. For example, in one variant the funnel member 124 may include six sections arranged circumferentially and each triangular in shape with each of the sections configured to deflect to provide a circular-shaped aperture.

In further variants, the funnel member 124 may include two, three or four or more sections with the sections not being formed from flexible and resilient material. Rather, the sections are rigid and are movably coupled to a suitable structure of the receiver body 56 and/or the funnel member 124, for example the frame elements 168, in a manner to responsively move when subjected to forces moving the solid phase pharmaceutical waste material and/or the pushing member 120 through the first and second gaps 181, 182. In one example, the first and second sections 171, 172 formed from rigid material may be pivotally coupled to one of the frame elements 168, and the third and fourth sections 173, 174 formed from rigid material may be pivotally coupled to the other one of the frame elements 168. Each of the sections 171-174 pivot in a suitable manner to permit the solid phase pharmaceutical waste material and/or the pushing member 120 to move through the second gap 182. A biasing element (e.g., a torsion spring) may bias the sections 171-174 with suitable force to support certain solid phase pharmaceutical waste material, for example, a pill.

It is readily appreciated that when the pushing member 120 is in the second position, the sections 171-174 are in a deflected condition. As the lower surface 146 of the main body 132 moves through the second gap 182 and as the pushing member 120 is moved towards the first position, the sections 171-174 resiliently return to a natural condition. Yet, as best shown in FIG. 6, in the second position, a portion of the main body 132 may be disposed relatively "deep" within the solid waste volume 86, and perhaps in contact with the medicine-infused fluid contained within the solid waste volume 86 (i.e., the fluid subsequent to dissolving the active medication during the operational lifecycle of the waste receiver 52). As a result, moving the pushing member 120 from the second position to the first position may expose to the outside environment the portion of the main body 132 that may have been in contact with the medicine-infused fluid. The aforementioned concern is ameliorated by the funnel member 124 including wiper surfaces 186 associated with each of the sections 171-174. With continued reference to FIGS. 11 and 12, the wiper surfaces 186 are the surfaces in direct contact with the opposing sides 142 of the pushing member 120 as the main body 132 causes the sections 171-174 to deflect. With the sections 171-174 resiliently being urged against the opposing sides 142 of the pushing member 120, the wiper surfaces 186 provide a "wiper function" to remove any medicine-infused fluid present on the opposing sides 142 of the pushing member 120, further rendering the solid phase pharmaceutical waste material disposed within the solid waste volume 86 irretrievable.

As explained throughout the present disclosure thus far, the liquid phase pharmaceutical waste material is directed through the liquid receiver guide 102 into the liquid waste volume 88 for further treatment, and the solid phase pharmaceutical waste material is directed through the solid receiver guide 100 into the solid waste volume 86 for further treatment. The various treatment modalities for each of the liquid and solid phase pharmaceutical waste material will now be described.

The waste disposal system 50 may include a chemical composition 190 disposed within the waste receiver 52 for limiting the recoverability of the pharmaceutical waste material. The chemical composition 190 may include at least one of a fluid absorber 193 suitable for absorbing and retaining large amounts of fluid, and a reaction agent 194. The fluid absorber 193 may be the superabsorbent polymer (SAP) previously mentioned that absorbs the liquid phase pharmaceutical waste material deposited to the waste receiver 52 such that the liquid phase pharmaceutical waste material is not readily recoverable and/or retrievable from the liquid waste volume 88.

By way of non-limiting example, the SAP may be a polyacrylic acid salt-based polymer, a vinyl alcohol-acrylic acid salt-based polymer, a PVA based polymer, an isobutylene-maleic anhydride polymer, a polysaccharide based polymer such as carboxymethyl starch, carboxymethyl cellulose, and hydroxypropyl cellulose, nonionic based polymers such as polyvinyl alcohol and polyvinyl ethers, a cationic based polymer such as polyvinyl pyridine, polyvinyl morpholinione, and N,N-dimethylaminoethyl or N,N-diethylaminopropyl acrylates and methacrylates, a carboxy group based polymer such as hydrolyzed starch-acrylonitrile graft copolymers, partially neutralized hydrolyzed starch-acrylonitrile graft copolymers, hydrolyzed acrylonitrile or acrylamide copolymers and polyacrylic acids, and combinations thereof.

The reaction agent 194 may be any agent suitable for limiting the recoverability of pharmaceutical waste material. The reaction agent 194 may include a bittering agent, an emetic, a denaturant, an ionization agent, an oxidizing agent, a catalyzing agent, an anti-fungal agent, a viscosity modifier, activated charcoal, and combinations thereof. The reaction agent 194 may chemically and/or physically alter, break down, deactivate, denature, or otherwise change the pharmaceutical waste material deposited within the waste receiver 52 such that the pharmaceutical waste material is not readily recoverable and/or retrievable from the liquid waste volume 88. In the context of this disclosure, the term denature means to prevent use or reclamation of waste drugs, or to deter use through agents, and/or to provide interference, expense, time, and complex procedures thereby making recovery for human consumption or use prohibitive, impractical, highly inefficient, and/or to render the waste drug biologically inactive. The term unrecoverable means that the pharmaceutical waste material has been chemically or physically altered and/or deactivated such that the pharmaceutical waste material is no longer usable to provide its previous function, to perform its previous purpose, and/or to make the pharmaceutical waste material not useful for human consumption.

The bittering agent may be any type of bittering agent suitable to render the pharmaceutical waste material unpalatable in taste, for example, denatonium benzoate. The emetic may be any type of emetic suitable to induce vomiting upon ingestion, for example, may be Ipecac, mustard powder, and combinations thereof. The denaturant may be, for example, quinine sulfate dehydrate, rucine (or brucine sulfate), nicotine, cinchonidine (or cinchonidine sulfate), 2-hydroxymethyl ether, 2-(hydroxymethyl) amino ethanol, ammonium hydroxide, sodium hydroxide, denatonium benzoate, quassin, naringin, sodium chloride, sodium carbonate, ferrous sulfate, edifas B, sodium carboxymethyl cellulose, carboxymethyl ether, chlorine dioxide, chlorine, bromine, sodium bicarbonate, formamide (deionized), guanidine thiocyanate, guanidine isothiocyanate, sodium dodecyl sulfate (SDS), formamide, guanidine hydrochloride, guanidine isothiocyanate solution, urea, thiourea, guanidinium chloride, dihydrofolate reductase, calcium sulfate dihydrate, Cole-Parmer quinine, Cole-Parmer 2-ketoglutaric acid, Cole-Parmer tetramethyltin, 2-ketoglutaric acid, cerium sulfate, quercetin dihydrate, oxalic acid dihydrate, lithium sulfate, (+)-(R)-trans-4-(1-Aminoethyl)-N-(4-pyridyl) cyclohexanecarboxamide dihydrochloride, (+/−)-1-(5-Isoquinolinesulfonyl)-2-methylpiperazine dihydrochloride, (+/−)-3-Aminopyrrolidine dihydrochloride, (+/−)-trans-4-(2-Pyridinyl)-pyrrolidine-3-carboxylic acid dihydrochloride, (+/−)-trans-4-(4-Pyridinyl)-pyrrolidine-3-carboxylic acid dihydrochloride, (−)-N-(1(R)-Phenylethyl)-1-azabicyclo[2.2.2]octan-3(S)-amine dihydrochloride, (1,4-Dimethylpiperazin-2-yl)acetic aciddihydrochloride, (1-(5-Isoquinolinesulfonyl)-homopiperazine dihydrochloride, (1-Aza-bicyclo[2.2.2]oct-3-yl)-(4-fluoro-benzyl)-amine dihydrochloride, (1-Aza-bicyclo[2.2.2]oct-3-yl)-(4-methoxy-benzyl)-amine dihydrochloride, (1-Methyl-1H-benzimidazol-2-yl)methylamine dihydrochloride, (1-Methyl-piperidin-4-yl)-pyridin-3-ylmethylamine-dihydrochloride, (1-[1,3]Oxazolo[4,5-b]pyridin-2-ylpyrrolidin-3-yl)methylamine dihydrochloride: (1H-Imidazol-2-yl) methanamine dihydrochloride, (1R,2R)-trans-1,2-Cyclopentanediamine dihydrochloride, (1S,2S)-1,2-bis(2,4, 6-trimethylphenyl)ethylenediamine dihydrochloride hydrate, (1S,2S)-1,2-bis(2-Chlorophenyl)ethylenedi amine dihydrochloride, (1S,2S)-1,2-bis(4-Fluorophenyl)ethylenediamine dihydrochloride: (1S,2S)-1,2-Bis(4-methoxyphenyl)ethylenediamine dihydrochloride, (1S,2S)-1,2-bis(4-Nitrophenyl)ethylenediamine dihydrochloride, (1S,2S)-1,2-di-1-naphthylethylenediamine dihydrochloride, (1S,2S)-trans-1,2-Cyclopentanediamine dihydrochloride, (1S,4S)-5-Methyl-2,5-diazabicyclo[2.2.1]heptane dihydrochloride, (2,4-Dimethyl-1,3-thiazol-5-yl)methylaminedihydrochloride, (2-Amino-benzothiazol-8-yl)-acetic acid dihydrochloride, (2-Chloro-6-fluorobenzyl)hydrazine dihydrochloride, (2-Dimethylaminoethyl)-reserpilinate dihydrochloride, (2-Ethyl-1,4-diazepan-1-yl)methanoldihydrochloride, (2-Imidazol-1-ylethyl)methylamine dihydrochloride, (2-Imino-thiazol-3-yl)acetic acid dihydrochloride, and combinations thereof. The oxidizing agent may be, for example, a chlorine-based oxidizing agent, a non-chlorine-based oxidizing agent, and combinations thereof. Further non-limiting examples of the chlorine-based oxidizing agent may be sodium hypochlorite, magnesium hypochlorite, calcium hypochlorite, sodium dichloroisocyanurate dihydrate, or any other stable solid chlorine compounds and salts thereof. The chlorine-based oxidizing agent may be sodium dichloroisocyanurate dehydrate. The chlorine-based oxidizing may be in solid form and may be shelf-stable. Further examples of the non-chlorine-based oxidizing agent may be bromine-based oxidizing agents, stabilized peroxide compounds such as persulfate, permonosulfate, permanganate, and other stabilized peroxide compounds and salts thereof, and metal oxides.

The chemical composition 190 may consist, comprise, or consists essentially of, the SAP and the chlorine-based oxidizing agent. When the composition comprises the SAP and the chlorine-based oxidizing agent, the SAP may be present in an amount of at least 85, at least 90, or at least 95, percentage by weight (wt. %) based on the total weight of the composition. Even more particularly, the SAP may be present in an amount of 96, 97, or 98, wt. % based on total weight of the composition, and the chlorine-based oxidizing agent may be present in an amount of less than 15, less than 10, less than 5, less than 2.5, or less than 1 wt. % based on the total weight of the composition. The reaction agent 194 may include quinine sulfate dehydrate in an amount of from 40 to 100 wt. % based on the total weight of the reaction agent 194, Ipecac in an amount of from 0 to 60 wt. % based on the total weight of the reaction agent 194, and denatonium benzoate in an amount of from 0 to 15 wt. % based on the total weight of the reaction agent 194.

Referring again to FIG. 6, the chemical composition 190 may be disposed in a packet 192. The packet 192 may include a film capable of being dissolved by water. In this manner, the addition of liquid phase pharmaceutical waste material and/or water to the liquid waste volume 88 solubilizes the film thereby releasing the chemical composition 190. The film may include a water-soluble polymer, for examples, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, starch, high amylose starch, hydroxypropylated high amylose starch, dextrin, pectin, chitin, chitosan, levan, elsinan, collagen, gelatin, zein, gluten, soy protein isolate, whey protein isolate, casein and combinations thereof. The film may include polyvinyl alcohol. The packet 192 may be fluid permeable, and include a screen material, a mesh material, or the like. It is contemplated that the packet 192 may further assume configurations capable of releasing the chemical composition 190 upon an occurrence of a triggering event, such as an elapsed period of time, contact with a specific type of material, and the like.

The packet 192 may be positioned in any suitable location of the liquid waste volume 88. In one example, the packet 192 is positioned approximately in the area shown in phantom in FIG. 6, such as on a shelf within the liquid volume or solid volume. With the packet 192 in an upper portion of the liquid waste volume 88 beneath the liquid receiver guide 102, an initial amount of the liquid phase pharmaceutical waste material encounters and dissolves the packet 192, after which the film at least partially solubilizes and the chemical composition 190 is released to descend within the liquid waste volume 88 under the influence of gravity. Numerous alternatives for arranging the chemical composition 190 within the liquid waste volume 88 are contemplated, including those introduced later in the present disclosure and those described in co-owned U.S. Pat. Nos. 8,348,056; 8,534,459; 8,573,426; 8,616,397; 9,044,377; 9,456,954, and co-owned United States Patent Publication No. 2016/0325322, the contents of each being hereby incorporated by reference in its entirety. The volume of the chemical composition 190 disposed within the packet 192 may be any volume suitable for rendering the pharmaceutical waste material within the waste receiver 52 less recoverable and/or retrievable from the liquid waste volume 88. The volume of the chemical composition 190 disposed within the packet 192 may be based on the volume of the waste receiver 52.

As mentioned, a liquid, such as water, may be added to the solid receiver guide 100 to prime the solid waste volume 86 prior to use. In addition or an alternative to water being within the solid waste volume 86 to dissolve the active medication in the solid phase pharmaceutical waste material, another reaction agent (not shown) may be provided to react with water or other fluids in order to chemically and/or physically break down the solid phase pharmaceutical waste material within the solid waste volume 86, and/or make the solid waste undesirable and/or indigestible. The reaction agent may be positioned and/or contained within one or more dissolvable or fluid permeable packets (not shown) within the solid waste volume 86. For example, multiple packets may be used with each packet containing a same or different reaction agent. The fluid may catalyze the reaction between the solid phase pharmaceutical waste material and the reaction agent to destroy or otherwise chemically and/or physically change the solid waste to an unusable and/or unrecoverable form. Alternatively, the liquid may solidify the reaction agent to encapsulate or otherwise surround the solid phase pharmaceutical waste material in the solid waste volume 86.

At least a substantial portion of the receiver body 56 may be formed from opaque materials so as to conceal the presence of any of the pharmaceutical waste material deposited therein. Yet it is desirable to provide an indication to the user of the level or volume of the pharmaceutical waste material within the container volume 58, and more particularly the liquid phase pharmaceutical waste material within the liquid waste volume 88. The indication, for example a visual indication, alerts the user that the capacity of the replaceable waste receiver 52 is being neared, and the time to replace the waste disposal system 50 with a new waste receiver 52 may be approaching. Referring to FIGS. 1, 2, 6 and 14, the waste disposal system 50 may include an indicator or a viewing port 196 associated with the receiver body 56. The indicator 196 may be suitably positioned on the receiver body 56 to come into contact with the liquid phase pharmaceutical waste material when a level of the liquid phase pharmaceutical waste material is above a predetermined level, for example, nearing the capacity of the container volume 58. The indicator 196 is disposed on or within the front wall 62 and generally positioned near the top of the waste receiver 52. More specifically, the indicator 196 is positioned approximately spaced from the bottom wall 68 by three-quarters of a height of the receiver body 56 defined between the top and bottom walls 66, 68. Once the level of the liquid phase pharmaceutical waste material is at the position of the indicator 196, the indicator 196 provides visual indication to the user. In one example, the indicator 196 is the viewing port including a window 198 formed from transparent material with the window 198 aligned with an aperture 200 defined by the front wall 62 of the receiver body 56. The user may view the fluid line with the container volume 58 when the fluid line is in contact with an inner surface of the window 198 behind the aperture 200. A plurality of indicators may also be provided along the height, denoting the various proportions of filling for the container.

In another example, the indicator 196 is a liquid contact indicator (also known as a moisture-detecting indicator or liquid submersion indicator) formed from material configured to undergo a chemical reaction and change colors upon coming into direct contact with the liquid phase pharmaceutical waste material within the liquid waste volume 88. The liquid contact indicator may be a first color (e.g., white) upon assembly and installation at the service location, and change to a second color (e.g., red) once the level of the liquid phase pharmaceutical waste material is above the predetermined level based on the position of the indicator 196. The figures show a single indicator 196 in the aforementioned position, but it is contemplated the waste receiver 52 may include two, three, or four or more indicators suitably positioned to provide visual indication(s) of the level of the pharmaceutical waste material within the container volume 58.

In one variant, a coloring agent, for example a dye, may be dispersed into the liquid waste volume 88 to color the liquid phase pharmaceutical waste material and/or the fluid absorber 193. The colored liquid phase pharmaceutical waste material and/or the fluid absorber 193 is more readily visible through the viewing port comprising the indicator 196. In one example, the coloring agent is provided within the packet 192 together with the fluid absorber 193. The liquid phase pharmaceutical waste material may solubilizes the film of the packet 192 thereby releasing the coloring agent and the chemical composition 190 into the liquid waste volume 88. As additional amounts of the liquid phase pharmaceutical waste material is added to the liquid waste volume 88, the material and the fluid absorber 193 assume the color of the coloring agent. Once the fluid line is in contact with an inner surface of the window 198 behind the aperture 200, the colored material is readily visible to the user viewing the indicator 196.

Once it is desired to replace the waste receiver 52, for example based on the visual indication provided to the user with the indicator 196 showing the waste receiver 52 to be sufficiently full, the waste disposal system 50 may include further advantageous features to facilitate safe disposal of the waste receiver 52. In particular, it is undesirable to transport the waste receiver 52 containing any contents in the liquid phase, which may include residual water added to the solid waste volume 86 to dissolve the solid phase pharmaceutical waste material prior to use. Known systems may require adding a substance to substantially solidify the liquid contents. Yet those systems requiring separately storing a solidifying agent during the operational lifecycle of the waste receiver 52, then further require handling and/or adding the substance are associated with risk of exposure to potentially harmful chemicals. The waste disposal system 50 of the present disclosure may advantageously provide for near-complete or complete solidification of the pharmaceutical waste material in a self-contained manner.

The waste receiver 52 may include at least one orifice 202 providing fluid communication between the solid waste volume 86 and the liquid waste volume 88. Referring to FIGS. 7-9, the partition 104 of the diverter 90 defines the orifice 202, and more particularly, two orifices 202 extend through the sidewall 106 at least partially defining the partition 104. The orifices 202 are generally positioned near the top of the receiver body 56 such that fluid from the solid waste volume 86 (e.g., the medicine-infused fluid) does not prematurely pass through the orifices 202 to the liquid waste volume 88 until the self-contained solidification method is performed. It is contemplated that in alternative variants, the orifice(s) 202 may be positioned within any suitable portion of the diverter 90. The diverter 90 may further include at least one channel 204 in communication with the orifices 202. FIGS. 7 and 9 show two channels 204 recessed within the sidewall 106 and extending between the orifices 202 and the lower wall 108 of the partition 104. The channels 204 ensure that fluid communication is maintained between the solid and liquid waste volumes 86, 88 via the orifices 202 should the liquid waste volume 88 become substantially consumed with the fluid absorber 193. In other words, as the fluid absorber 193 absorbs the liquid phase pharmaceutical waste material in the liquid waste volume 88, the fluid absorber 193 expands significantly and may directly contact the sidewall 106 of the partition 104 near the orifices 202. The fluid from the solid waste volume 86 may be effectively transferred to the liquid waste volume 88 through the orifices 202 and the clearance afforded by the channels 204.

The self-contained solidification method will now be described. The liquid waste volume 88 may include the liquid phase pharmaceutical waste material that is substantially solid after being absorbed by the fluid absorber 193 (e.g., the SAP). The solid waste volume 86 may include the solid phase pharmaceutical material that is substantially liquid after being dissolved by the reaction agent 194 (e.g., the medicine-infused fluid). The fluid absorber 193 may not be fully saturated such that the fluid absorber 193 has capacity to absorb additional liquid. The user positions the retainer cover 82 on the receiver body 56 to cover the opening 72 to seal the solid phase pharmaceutical waste material and the liquid phase pharmaceutical waste material within the receiver body 56 in manners previously described. With particular reference to FIG. 6, the waste receiver 52 is manually repositioned or manipulated, such as inverted, such that the liquid contents within the solid waste volume 86 descend under the influence of gravity (in the direction of arrow 208 when the waste receiver 52 is substantially inverted). The waste receiver 52 may be manipulated in a manner that agitates the liquid contents. The liquid contents may be prevented from exiting the solid receiver guide 100 by the pushing member 120 sealing the inlet 118 of the solid receiver guide 100. Further, the cover 82 seals the solid and liquid receiver guides 100, 102 to prevent egress of the contents of the receiver volume 58 thereby rendering the method self-contained. The liquid contents pass from the solid waste volume 86, through the orifices 202 (in the direction of arrow 208), and into the liquid waste volume 88 towards the fluid absorber 193 (in the direction of arrow 210). The fluid absorber 193 with remaining capacity to absorb additional liquid absorbs the liquid contents originally comprising the solid phase pharmaceutical waste material. Consequently, the amount of liquid contents within the waste receiver 52 is minimized, and preferably eliminated, prior to transport, processing, and/or disposal. At no point during the above self-contained solidification process was the user exposed to external substances required to solidify the liquid contents within the solid receiver volume 86, as the cover 82 was coupled to the receiver body 56 prior to the user manipulating the waste receiver 52. Alternatively, the solid waste volume may be free of an absorber.

Additionally or alternatively, it is contemplated that at least a portion of the liquid contents may be directed from the solid waste volume 86 to the liquid waste volume 88 through the inlet 118 of the solid receiver guide 100 and the inlet 110 of the liquid receiver guide 102 (with the pushing member 120 not sealing the inlet 118). The underside of the cover 82 may be spaced apart from the upper wall 128 of the diverter 90. As a result, as the waste receiver 52 is manually repositioned or manipulated, such as inverted, such that the liquid contents within the solid waste volume 86 descend under the influence of gravity (arrow 208). The liquid contents pass through the inlet 118, and into contact with the underside of the cover 82. The liquid contents move along the underside of the cover 82 and through the inlet 110 of the liquid receiver guide 102. With further manipulation (e.g., returning the waste receiver 52 to upright), the liquid contents descend under the influence of gravity within the liquid waste volume 88 (arrow 210).

One or more indicia 212 may be provided on a suitable location of the waste receiver 52 or the cover 82 to provide information to the user as to which direction to generally tip or agitate the waste receiver 52 to direct the liquid contents through the orifices 202 or the inlet 118. FIG. 1 shows the indicia 212 including an arrow disposed on cover 82 with pointing towards a direction that, once the cover 82 is secured to the receiver body 56, corresponds to a direction of the orifices 202 relative to the solid waste volume 86, and thus the direction to generally tip or agitate the waste receiver 52 during the self-contained solidification method. Additionally or alternatively, the indicia 212 (or additional indicia) may be provided on the body portion 92 of the diverter 90 so as to be visible to the user prior to sealing the solid phase pharmaceutical waste material and the liquid phase pharmaceutical waste material with the cover 82. Other shapes and positions of the indicia 212 are considered within the scope of the present disclosure.

Figure 13:
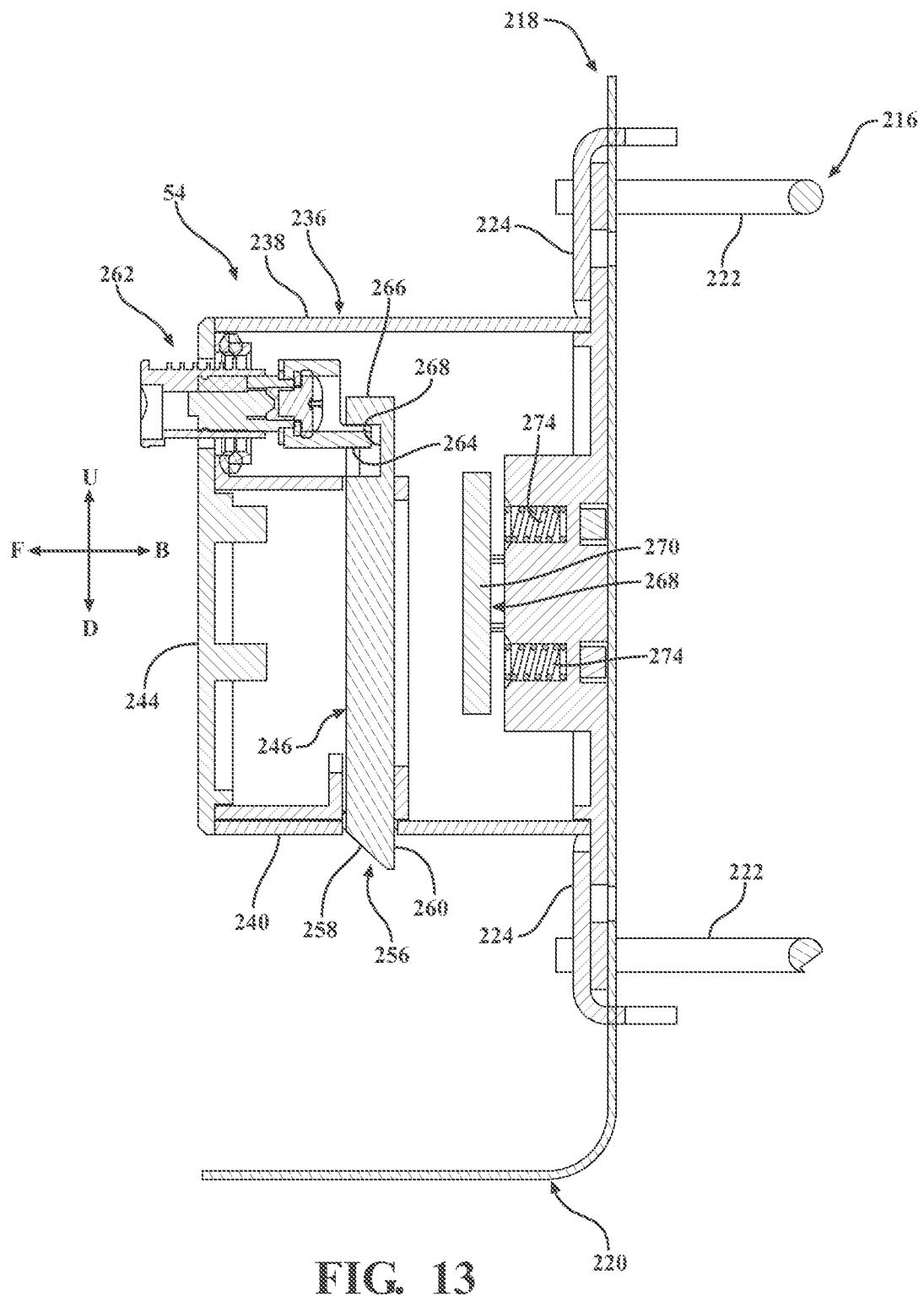
FIG. 13 is a sectional view of the locking assembly of FIG. 2 taken along section lines 13-13.

Returning to FIGS. 1-3 and with further reference to FIG. 13, the locking assembly 54 previously mentioned releasably secures the waste receiver 52 to a fixed surface (not shown), for example, a wall, a door, a tabletop, a cart, a upstanding post, and the like. The waste disposal system 50 includes a bracket 216 adapted to be secured to the fixed surface. The bracket 216 includes a vertical mount 218 and a horizontal mount 220. Certain variants may include only one of the aforementioned mounts 218, 220. The vertical and horizontal mounts 218, 220 may be formed as an L-shaped member as shown. The bracket 216 may further include one or more anchors 222 and one or more anchor plates 224 to be secured to the anchors 222. The anchors 222 may include U-shaped rings configured to surround a fixed structure of the fixed surface such that, subsequent to securing the anchor plates 224 to the anchors 222 opposite the vertical mount 220, the bracket 212 may not be decoupled from the fixed surface without extraordinary difficulty. The horizontal mount 220 may include holes configured to receive fasteners (e.g., screws, bolts, rivets, etc.) to secure the bracket 212 to a horizontal fixed surface.

FIGS. 2, 3 and 14 show the receiver body 56 of the waste receiver 52 defining a lock passageway 230. The lock passageway 230 may be considered separate from the opening 72 of the receiver body 56. In other words, whereas the opening 72 is in communication with the container volume 58, the lock passageway 230 may not be in communication with the container volume 58. Rather, it is the outer surface 60 that defines the lock passageway 230. More particularly the front wall 62 of the receiver body 56 may define an aperture 232, and the rear wall 64 of the receiver body 56 may define another aperture 234 with apertures 232, 234 opening into or at least define a portion of the lock passageway 230 such that the receiver body 56 may surround the lock passageway 230. The lock opening 230 may be generally centered through the receiver body 56 in a front-to-back direction; however, it is contemplated that the lock passageway 230 may be provided in any suitable pose (i.e., position and orientation). In one variant, for example, the lock passageway extends between the two side walls 70 with the waste receiver 52 to be "side-loaded" when coupled with the locking assembly 54.

The locking assembly 54 includes a lock housing 236 sized to be removably positioned at least partially within the lock passageway 230. With reference to FIGS. 2 and 3, the lock housing 236 includes a top wall 238 opposing a bottom wall 240, opposing sidewalls 242 extending between the top and bottom walls 238, 240. A front wall 244 extends between the top, bottom, and opposing sidewalls 238, 240, 242 to define the lock housing 236 that is a rectangular prism. The vertical mount 218 may form a rear wall of the lock housing 236, or alternatively the lock housing 236 may include a discrete rear wall coupled to the vertical mount 218. The front wall 244 may be oblong corresponding to the apertures 232, 234 that are oblong. The complementary oblong shapes of the lock housing 236 and the lock passageway 230 facilitate orienting and securing the waste receiver 52 to the locking assembly 54, and thus to the fixed surface, in a single orientation. Further, with the waste receiver 52 coupled to the locking assembly 54, the top, bottom, and opposing sidewalls 238, 240, 242 of the lock housing 236 is surrounded in the lock passageway 230 with the front wall 244 positioned near the aperture 232 and accessible to the user for actuating the locking assembly 54 in a manner to be described.

The locking assembly 54 may include an engagement feature 246 movably coupled to the lock housing 236. The receiver body 56 of the waste receiver 52 may include a complementary engagement feature 248 configured to receive the engagement feature 246 of the locking assembly 54 to releasably secure the waste receiver 52 to the locking assembly 54 and thus to the fixed surface in the single orientation. With concurrent reference to FIGS. 3, 13 and 14, the complementary engagement feature 248 of the waste receiver 52 may define at least a portion of the lock passageway 230. The complementary engagement feature 248 of the waste receiver 52 may include one or more of a keyway 250, a channel 252, and an inclined surface 254 with function of each to be described. The engagement feature 246 of the locking assembly 54 may include a protrusion 256 extending from the lock housing 236. As best shown in FIG. 4, the engagement feature 246 is a columnar structure extending from within the lock housing 236 and through an opening within the lower wall 240 to define the protrusion 256. The protrusion 256 may further include an inclined surface 258 and an interference surface 260.

The coupling of the complementary engagement features 246, 248 will now be described. The receiver body 56 is positioned such that the lock passageway 230 and the lock housing 236 are in alignment. The receiver body 56 is moved towards the lock housing 236, and the lock passageway 230 receives the front wall 244 of the lock housing 236. Referring to FIGS. 13 and 14, the protrusion 256 of the engagement feature 246 biased in a first or downward direction (D) with a biasing member (not shown), the rear of the receiver body 56. More particularly, the inclined surface 258 of the protrusion 256 directly contacts the inclined surface 254 of the engagement feature 248. The interference of the inclined surfaces 254, 258 cooperate to overcome the biasing force of the biasing member and move the engagement member 246 in an upward or second direction (U) opposite the first direction with a continued force applied to the waste receiver 52 in a rearward direction (R) towards the fixed surface. In such an arrangement, the complementary engagement features 246, 248 cooperate to orient the waste receiver 52 relative to the locking assembly 54 to the single orientation. The protrusion 256 of the engagement feature 246 moves along the channel 252 of the engagement feature 248 until encountering the keyway 250 within the channel 252 (see FIG. 3). The biasing member resiliently returns the engagement feature 246 (i.e., moves in the first direction) to its natural position such that the protrusion 256 at least partially extends through the keyway 250. The interference surface 260 is in engagement with a rearward lip partially defining the keyway 250, and the waste disposal system 50 may be considered in a locked configuration in which the engagement feature 246 is moved to prevent the waste receiver 52 from being decoupled from the locking assembly 54. It is contemplated that another inclined surface 254' (see FIG. 14) may be provided opposite the inclined surface 254 with the waste receiver 52 capable of being coupled to the locking assembly 54 in one of two configurations; i.e., the front wall 62 oriented towards the fixed surface or the rear wall 64 oriented towards the fixed surface.

With continued reference to FIG. 13, the locking assembly 54 includes a lock cylinder 262 and a lock spindle 264 operably coupled to the engagement feature 246. The lock spindle 262 may be selectively actuated through an input to the lock cylinder 262 to actuate the locking assembly 54 between the locked configuration and an unlocked configuration to be described. The lock spindle 264 may include a post positioned eccentric to an axis of rotation of the lock cylinder 262, as shown in FIG. 13, or alternatively a cam-like structure. The engagement feature 246 includes a lock protrusion 266 defining a recess 268 sized to receive the lock spindle 264. The lock cylinder 262 receives the input from the user, for example, insertion and turning of a key, to rotate the lock spindle 264. The lock spindle 264 rotates and interferes with the lock protrusion 266, and with continued rotation of the lock spindle 264, the engagement feature 246 is moved in the second or upward direction against the biasing force of the biasing member. The protrusion 256 is moved out of engagement with the keyway 250 of the complementary engagement feature 248. The locking assembly 54 may be considered to be in the unlocked configuration in which the engagement feature 246 has been moved to permit the waste receiver 52 to be decoupled from the locking assembly 54. Thus, with the biasing member biasing the engagement feature 246 to the locked position, the lock spindle 264 may be selectively actuated to disengage the engagement feature 246 in the locked configuration, and engage the engagement feature 246 in the unlocked configuration.

To facilitate efficient decoupling of the waste receiver 52 from the locking assembly 54, the locking assembly 54 may include a decoupling member 268 coupled to and movable relative to the lock housing 236. The decoupling member 268 is configured to move the waste receiver 52 away from the fixed surface upon the locking assembly 54 entering the unlocked configuration. More particularly, the decoupling member 268 is biased away from the bracket 216 secured to the fixed surface with the decoupling member 268 automatically moving the waste receiver 52 from a first distance from the bracket 216 to a second distance from the bracket 216 greater than the first distance. The movement of the waste receiver 52 away from the bracket 216 facilitates ease with grasping and handling the waste receiver 52, and may also function as a safety feature as to visually ascertain quickly whether the waste receiver 52 is secured to the locking assembly 54 (users can tell when the waste receiver is spaced away from the bracket or not). With continued reference to FIGS. 2 and 13, the decoupling member 268 includes a central portion 270 and at least one wing 272 extending from the central portion 270. The central portion 270 may be disposed within the lock housing 236, and the wings 272 may extend from the opposing sidewalls 242 of the lock housing 236. The opposing sidewalls 242 may define slots sized to permit the wings 272 to slide relative to the lock housing 236. The locking assembly 54 may further include at least one biasing member 274 disposed within the lock housing 236 and positioned to engage the central portion 270 of the decoupling member 268. The biasing members 274 bias the decoupling member 268 away from the vertical mount 218 in the forward direction (F), and thus away from the fixed surface. With the waste receiver 52 coupled to the locking assembly 54 in the locked configuration, the waste receiver 52 is maintained at the first distance from the vertical mount 218. In the locked configuration, the biasing members 274 are resiliently deformed and are prevented from resiliently returning based on the engagement of the complementary engagement features 246, 248. In particular, the engagement of the protrusion 256 and a front lip at least partially defining the keyway 250 prevent the biasing members 274 from moving the decoupling member 268, and thus the waste receiver 52, in the forward direction.

As the locking assembly 54 is moved from the locked configuration to the unlocked configuration in the manner previously described, the disengagement of the protrusion 256 and the keyway 250 no longer prevent the biasing members 274 from moving the decoupling member 268. The biasing members 274 resiliently move the decoupling member 268 with the wings 272 in direct contact with the rear wall 64 of the receiver body 56 of the waste receiver 52. The wings 272 move the waste receiver 52 to the second distance from the vertical mount 218 greater than the first distance. A magnitude of the movement is based on the dimensions of the slot defined within the opposing sidewalls 242 of the lock housing 236, and may be typically on the order of an inch or so. The movement of the waste receiver 52 in the forward direction provides clearance between the waste receiver 52 and the locking assembly 54 for ease with grasping and decoupling the waste receiver 52 from the locking assembly 54. The positioning of the waste receiver 52 away from the bracket 216 may also function as a safety feature by providing visual confirmation that the waste receiver 52 is in the unlocked configuration, as mentioned. In other words, a passerby may quickly recognize without undue inspection that the waste receiver 52 is not locked to the locking assembly 54 and take corrective action, if necessary, to prevent undesirable diversion of the waste receiver 52.

Still another advantageous feature of the waste disposal system 50 may include a cover retention feature 276. As previously mentioned, the waste receiver system 50 may be assembled or packaged with a kit including the waste receiver 52, the cover 82, and the cap 83, the latter of which is removed and discarded upon installation of the waste receiver 52 at its service location. Yet the cover 82 remains decoupled from over the opening 72 of the receiver body 56 until the end of the operational lifecycle of the waste receiver 52. It is desirable to have the cover 82 at the ready should it be necessary to replace and dispose of the waste receiver 52. A known solution of coupling the cover with a tether with the cover dangling from the receiver body 56 is unsightly and may interfere with the depositing of the pharmaceutical waste material within the waste receiver.

With reference to FIGS. 1 and 2, the cover retention feature 276 is sized to removably receive the cover 82. The cover retention feature 276 may include a lip 278 extending from the front wall 62 of the receiver body 56. The lip may be arcuate with a radius approximate to that of the cover 82. The arcuate lip 278 may subtend an arc of 180°, as shown, or less but generally sufficient to prevent removal of the cover 82 with the waste receiver 52 coupled to the locking assembly 54. The lip 278 may also include a flange 280 defining a gap between the lip 278 and the front wall 70 with the gap sized to receive an outer rim 282 of the cover 82 (see FIG. 1). As is readily appreciated from the exploded view of FIG. 2, with the waste receiver 52 decoupled from the locking assembly 54, the cover 82 may be decoupled from the cover retention feature 276; i.e., slidably moved upwardly to disengage the lip 278 and the outer rim 282. Yet as is further appreciated from the perspective view of FIG.

1 with the waste receiver 52 coupled with the locking assembly 54, the cover 82 is prevented from being decoupled by the lock cylinder 242 of the locking assembly 54. In other words, the cover retention feature 276 and the locking assembly 34 cooperate to prevent removal of the cover 82 with the locking assembly 34 securing the waste receiver 52 to the fixed surface. The lock cylinder 242 extends from the front wall 244 of the lock housing 236 and is spaced from the lip 278 of the cover retention feature 276 by a distance sufficient to retain the cover 82 between the lip 278 and the lock cylinder 242 when the lock housing 246 is positioned within the lock passageway 230 and the waste receiver 52 is secured to the fixed surface. The distance may be slightly larger than a diameter of the cover 82.

The cover retention feature 276 may be at least functionally related to the decoupling member 268 and the complementary engagement features 246, 248 previously described. As mentioned, the decoupling feature 268 moves the waste receiver 52 away from the fixed surface once the locking assembly 54 is moved to the unlocked configuration and the complementary engagement features 246, 248 disengage. The magnitude of the movement may be at least greater than an amount that the lock cylinder 242 extends from the front wall 244 of the lock housing 236. As a result, once moving the locking assembly 54 from the locked configuration to the unlocked configuration and the decoupling feature 268 moves the waste receiver 52, the cover 82 becomes removably coupled with the cover retention feature 276.

Figure 15:
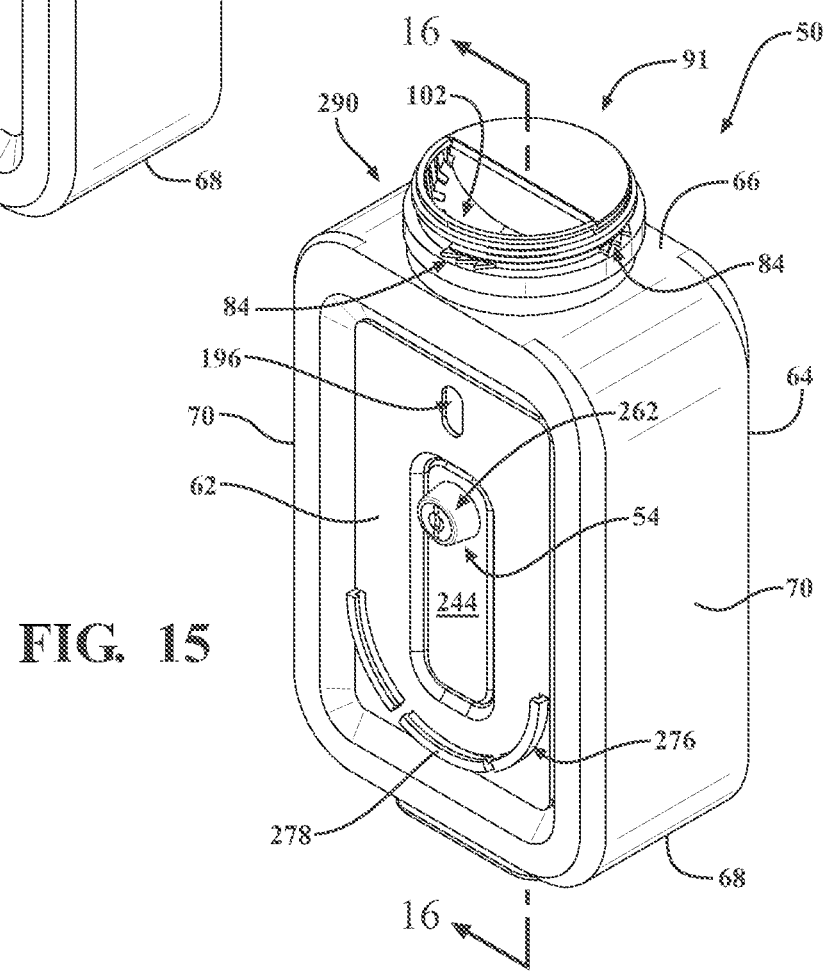
FIG. 15 is a perspective view of a pharmaceutical waste disposal system including a waste receiver and the locking assembly of FIG. 1.
Figure 16:
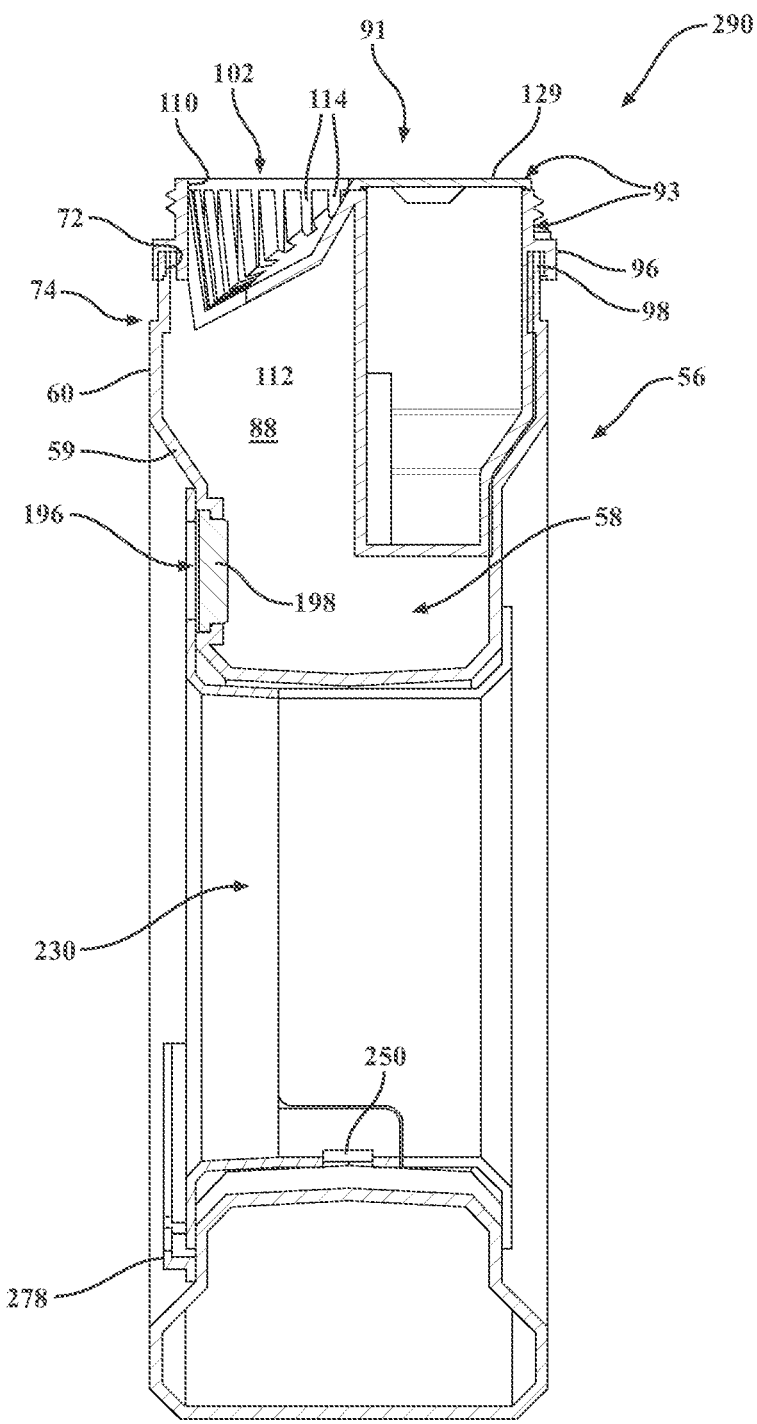
FIG. 16 is a sectional view of the waste receiver of FIG. 15 taken along section lines 16-16.
Figure 17:
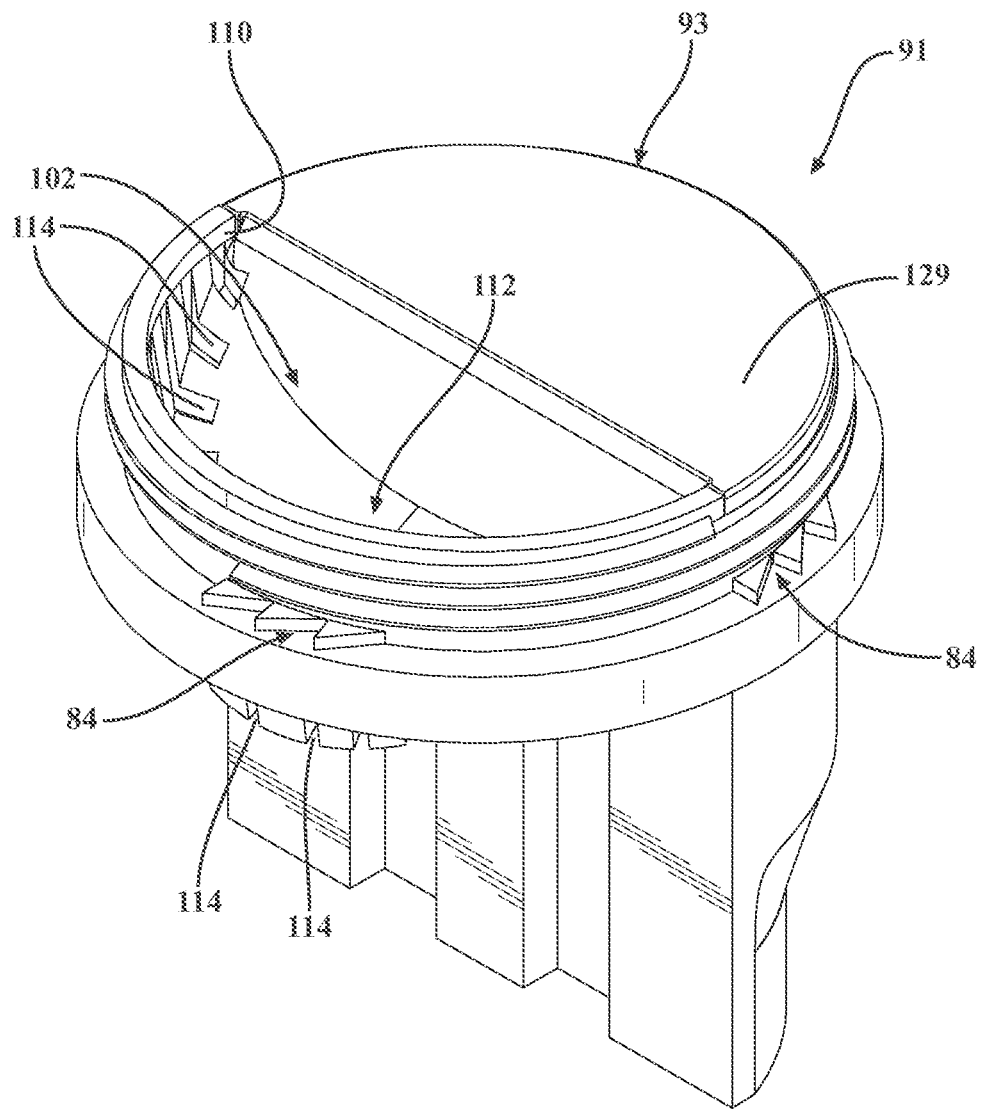
FIG. 17 is a perspective view of a diverter for the waste receiver of FIG. 15.
Figure 18:
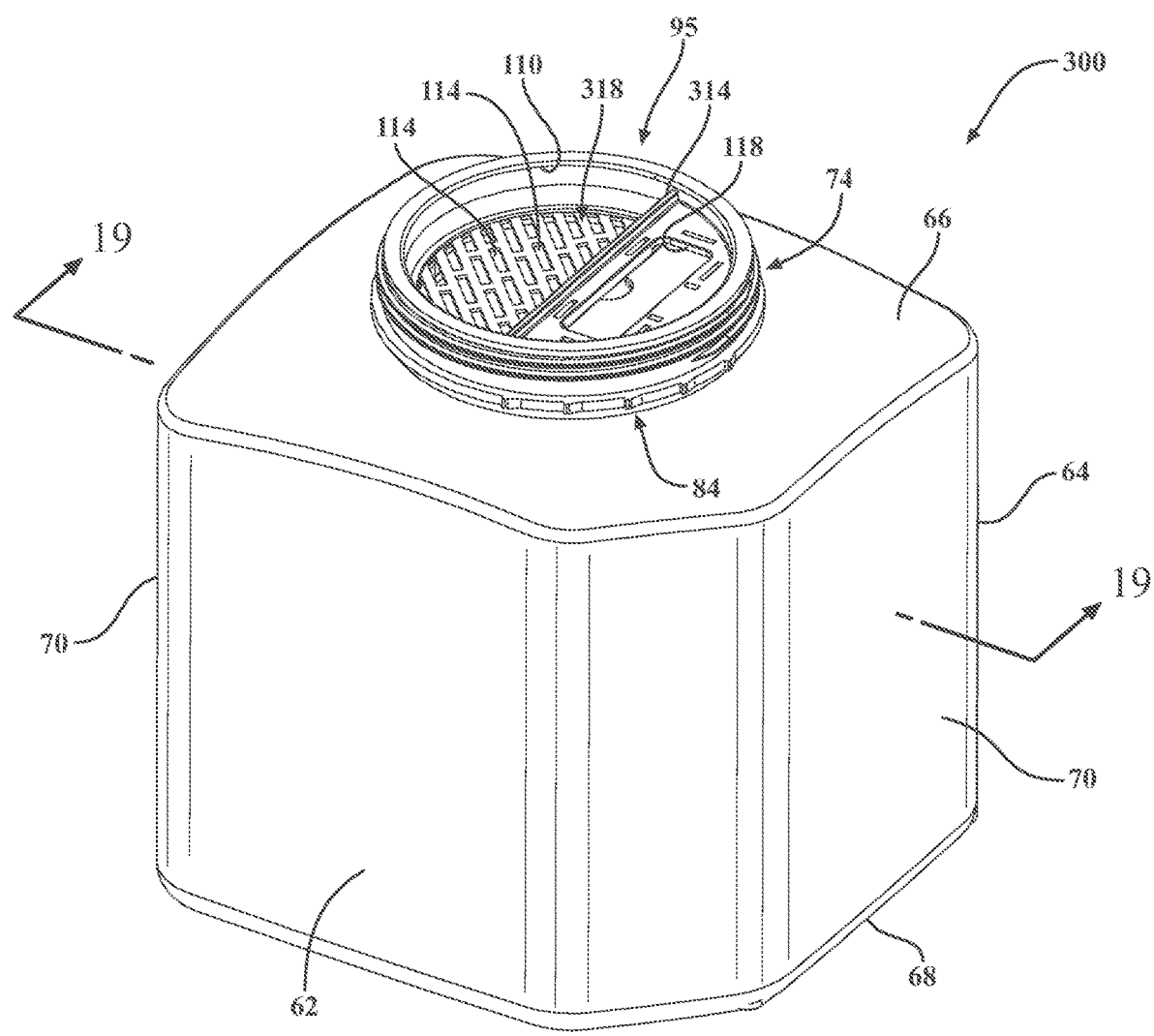
FIG. 18 is a perspective view of a waste receiver.

Referring now to FIGS. 15-17, a waste receiver 290 in accordance with another exemplary embodiment is shown. The waste receiver 290 is, at least in many respects, similar to the embodiment of the waste receiver 52 previously described with like numerals identifying like components. Certain structures common between the embodiments may be introduced only briefly in the interest of brevity.

In some respects, the waste receiver 290 may be considered a "liquid only" variant of the waste disposal system 50. The receiver body 56 of the waste receiver 290 includes the receiver body 56 the inner surface 59 defining the container volume 58 and the outer surface 60 opposite the inner surface 59 with the inner and outer surfaces 59, 60 defining the walls 64-70 of the receiver body 56. The receiver body 56 defines the opening 72, and in particular the neck 74 terminates at the lip 76 defining the opening 72 of the receiver body 56. The opening 72 is in fluid communication with the container volume 58, and the opening 72 receives the pharmaceutical waste material to be disposed within the container volume 58. The waste receiver 290 of the waste disposal system 50 may include the cover or the cap (not shown). The waste receiver 290 may include the coupling features 84 for receiving complementary coupling features of the cover in a manner that renders the waste material irretrievable.

The container volume 58 may be further defined by the liquid waste volume 88 in communication with the opening 72 of the receiver body 56. No solid waste volume may be provided. The diverter 91 diverts or directs the liquid phase pharmaceutical waste material to the liquid waste volume 88. The diverter 91 is coupled to the receiver body 56 and may include the body portion 93 positioned adjacent the opening 72 of the receiver body 56, and the lip 96 spaced circumferentially from the body portion 93 to define the gap 98 sized to receive the lip 76 of the receiver body 56 to effectively couple the diverter 90 with the receiver body 56. The diverter 91 includes the liquid receiver guide 102 coupled to the body portion 93 and at least partially disposed within the receiver body 56. The liquid receiver guide 102 is adapted to direct the liquid phase pharmaceutical waste material to the liquid waste volume 88. The liquid receiver guide 102 of the diverter 91 is in communication with the opening 72. When the cover or the cap is coupled with the diverter 91, the cover or the cap covers the liquid receiver guide 102.

As best shown in FIG. 16, the diverter 91 includes the partition. It should be readily appreciated this component is optional, as the diverter 91 neither includes a solid receiver guide nor a solid waste volume. Rather, the partition as shown may be vestigial and provided merely for manufacturing efficiency of the waste receiver 52, 290. In other words, the body portions 92, 93 may be manufacturing through the same technique, after which less significant alterations result in either the diverters 90, 91. Should the diverter 90 be desired, the upper wall 128 with the inlet 118 may be provided and certain other components may be subsequently assembled (e.g., the pushing member 120, the cutting element 126, etc.). Should the diverter 91 be desired, an upper wall 129 may be provided that lacks an inlet. The "solid waste volume" of may be merely an entirely closed chamber as shown in FIG. 16 without meaningful function. The liquid receiver guide 102 may include the inlet 110 defining the uppermost aspect of the liquid receiver guide 102. The funnel-type device 112 may be provided to define the inlet 110 and include the orifices 114 for the liquid phase pharmaceutical waste material to pass through to the liquid waste volume 88. The orifices 114 may include the plurality of slots arcuately spaced about the funnel-type device 112. The waste disposal system 50 may include chemical composition 190 disposed within the waste receiver 290 for limiting the recoverability of the pharmaceutical waste material. The chemical composition 190 may include the fluid absorber 193 (e.g., the SAP) suitable for absorbing and retaining large amounts of fluid, and the reaction agent 194. The waste receiver 290 may include the indicator or the viewing port 196 for providing an indication to the user of the level or volume of the pharmaceutical waste material within the container volume 58, and more particularly the liquid phase pharmaceutical waste material within the liquid waste volume 88.

The waste receiver 290 may be adapted to be releasably secured to the locking assembly 54, as previously described. In other words, the locking assembly 54 is configured to be coupled in the same manner with both the waste receivers 52, 290. The interchangeability of the waste receivers 52, 290 of the waste disposal system 50 advantageously provides for installing the waste receiver best suited for its service location. For example, treatment of patients in a typical patient care room of a medical facility may include providing patches and/or pills with more frequency than an operating room. Or, for another example, it may be determined that in certain months of the year patches are more frequently prescribed and provided to the patient. Without requiring reconfiguration of the locking assembly 54, the waste receiver 52 including the solid waste volume 86 may be releasably secured to the fixed surface. At a later time it may be determined the waste receiver 290 without the solid waste volume may be more appropriate, which can be installed at the service location with little difficulty. The aforementioned description regarding the locking assembly 54 is incorporated by reference in its entirety; i.e., the engagement features 246, 248, the decoupling member 268, etc. The waste receiver 290 may include the cover retention feature 276 sized to removably receive the cover and cooperate with the locking assembly 54 to prevent removal of the cover when the locking assembly 34 is securing the waste receiver 290 to the fixed surface.

Referring now to FIGS. 18-21, a waste receiver 300 in accordance with another exemplary embodiment is shown. The waste receiver 300 is, at least in some respects, similar to the embodiment of the waste receivers 52, 290 previously described with like numerals identifying like components. Certain structures common between the embodiments may be introduced only briefly in the interest of brevity.

The waste receiver 300 includes the receiver body 56 the inner surface 59 defining the container volume 58 and the outer surface 60 opposite the inner surface 59 with the inner and outer surfaces 59, 60 defining the walls 64-70 of the receiver body 56. The receiver body 56 defines the opening 72, and in particular the neck 74 terminates at the lip 76 defining the opening 72 of the receiver body 56. The opening 72 is in fluid communication with the container volume 58, and the opening 72 receives the pharmaceutical waste material to be disposed within the container volume 58. The waste receiver 300 may include the cover or the cap (not shown). The waste receiver 52 may include the coupling features 84 for receiving complementary coupling features of the cover in a manner that renders the waste material irretrievable.

Figure 19:
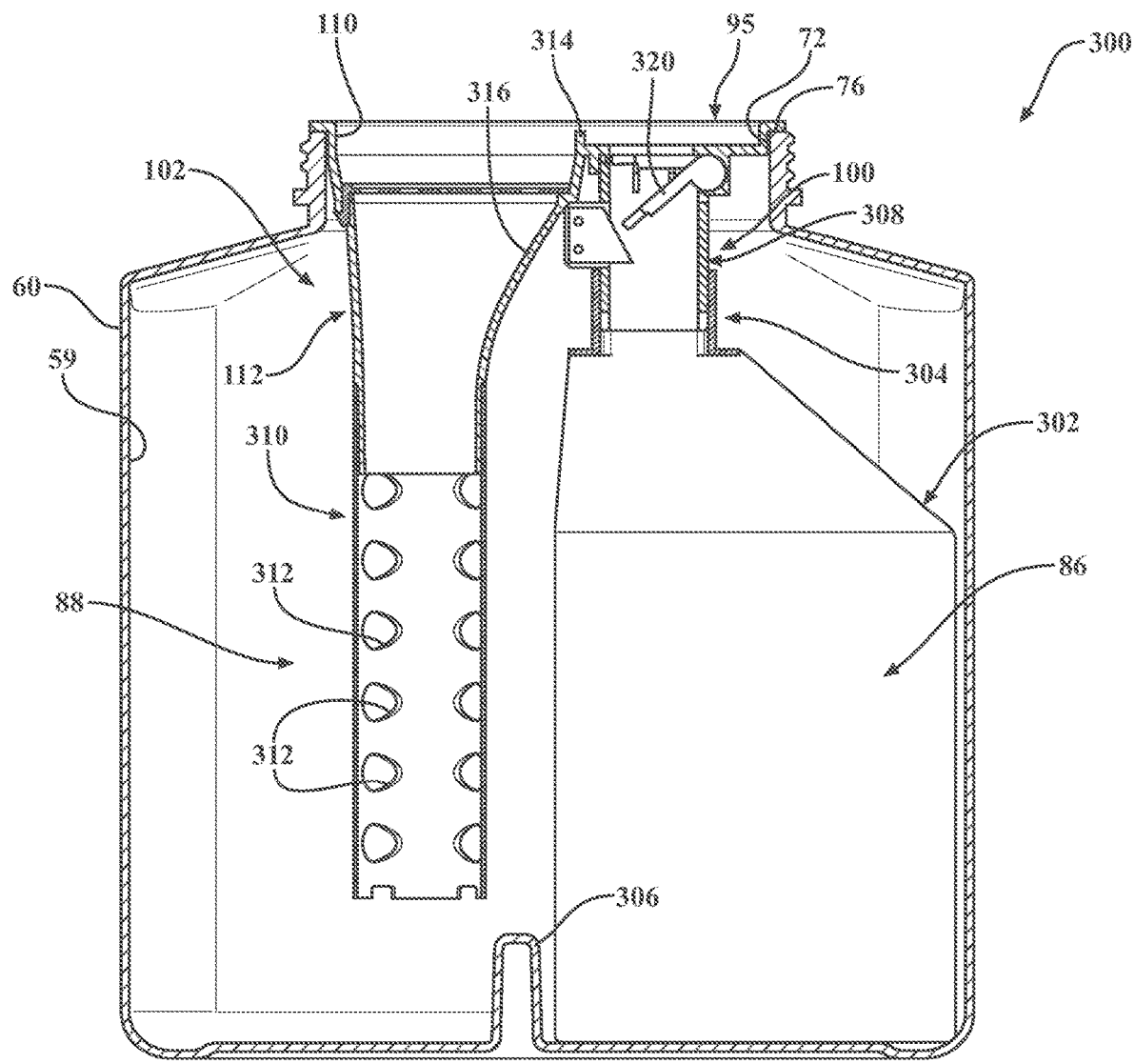
FIG. 19 is a sectional view of the waste receiver of FIG. 18 taken along section lines 19-19.

The diverter 95 is coupled to the receiver body 56 to facilitate the receiver body 56 receiving both the solid and liquid phase pharmaceutical waste material in a manner that renders the material irretrievable and/or unrecoverable. The diverter 90 comprises the body portion 92 having the rim 64 positioned adjacent the receiver body 56. The rim 64 of the diverter 95 is positioned in abutting relationship atop the rim 68 of the neck portion 56 as shown in FIG. 19. The rim 64 of the diverter 95 may be fixedly coupled to the receiver body 56, such as through welding, adhesion, or other semi-permanent or permanent joining means.

The solid receiver guide 100 is coupled to the body portion 92 of the diverter 95 and disposed within the receiver body 56. The solid receiver guide 100 is adapted to direct the solid phase pharmaceutical waste material to the solid waste volume 86. As shown in FIG. 19, the solid waste volume 86 comprises a portion of the container volume 58 of the receiver body 56. The liquid receiver guide 102 is also coupled to the body portion 92 and disposed within the receiver body 56. The liquid receiver guide 102 is adapted to direct the liquid phase pharmaceutical waste material to the liquid waste volume 88. The liquid waste volume 88 comprises another portion of the container volume 58 of the receiver body 56 with the liquid waste volume 88 being substantially separate from the solid waste volume 86.

The diverter 95 of the waste receiver 300 includes a bladder 302 disposed within the receiver body 56. The bladder 302 may be coupled to the solid receiver guide 100 with a bladder adapter 304 to be described. The bladder 302 is adapted to define the solid waste volume 86. With the bladder 302 defining the solid waste volume 86, the container volume 58 external to the bladder 302 may define the liquid waste volume 88. The bladder 302 may be formed of resilient material adapted to substantially maintain a natural shape after being positioned within the receiver body 56 during assembly. The bladder 302 may have a cross-sectional diameter greater than the opening 72 of the waste receiver 300 such that the bladder 302 is collapsed and inserted through the opening 72 during assembly. The resilient material of the bladder 302 may substantially return to its natural shape within the receiver body 56. Any suitable resilient material, such as polymers, foils, and the like, may be utilized for this function. The bladder 302 may be expandable based on the pharmaceutical waste material or other contents contained within the bladder 302. For example, the bladder 302 may be elastic and define a variable volume disposed with the container volume 58 of the receiver body 56 defining a fixed volume. Consequently, the liquid waste volume 88 within the container volume 58 is also a variable volume based on the variable volume of the bladder 302. The liquid waste volume 88 may be defined as a difference between the fixed volume of the receiver body 56 and the variable volume of the bladder 302. In one example, a stent (not shown) may be provided within the bladder 302 to maintain a degree of patency of the bladder 302 should the liquid phase pharmaceutical material within liquid waste volume 88 external the bladder 302 compress the bladder 302.

A partition (not shown), for example a vertical barrier, may be provided within the receiver body 56 with the bladder 302 positioned adjacent one side of the partition, and the liquid waste volume 88 defined by the container volume 58 on the other side of the partition. The partition may prevent encroachment on the bladder 302 by the expanding fluid absorber 193 to be described that is disposed in the liquid waste volume 88. The partition may be suitably dimensioned within the receiver body 56 to substantially constrain the expanding fluid absorber 193 to the liquid waste volume 88. With continued reference to FIG. 20, the waste receiver 300 may include a bladder holding member 306 positioned within the solid waste volume 86 adjacent an inner surface of the lower wall 68. For example, the bladder holding member 306 may be a tray adapted to suitably support and position a lower portion of the bladder 302 within the receive body 40.

Figure 20:
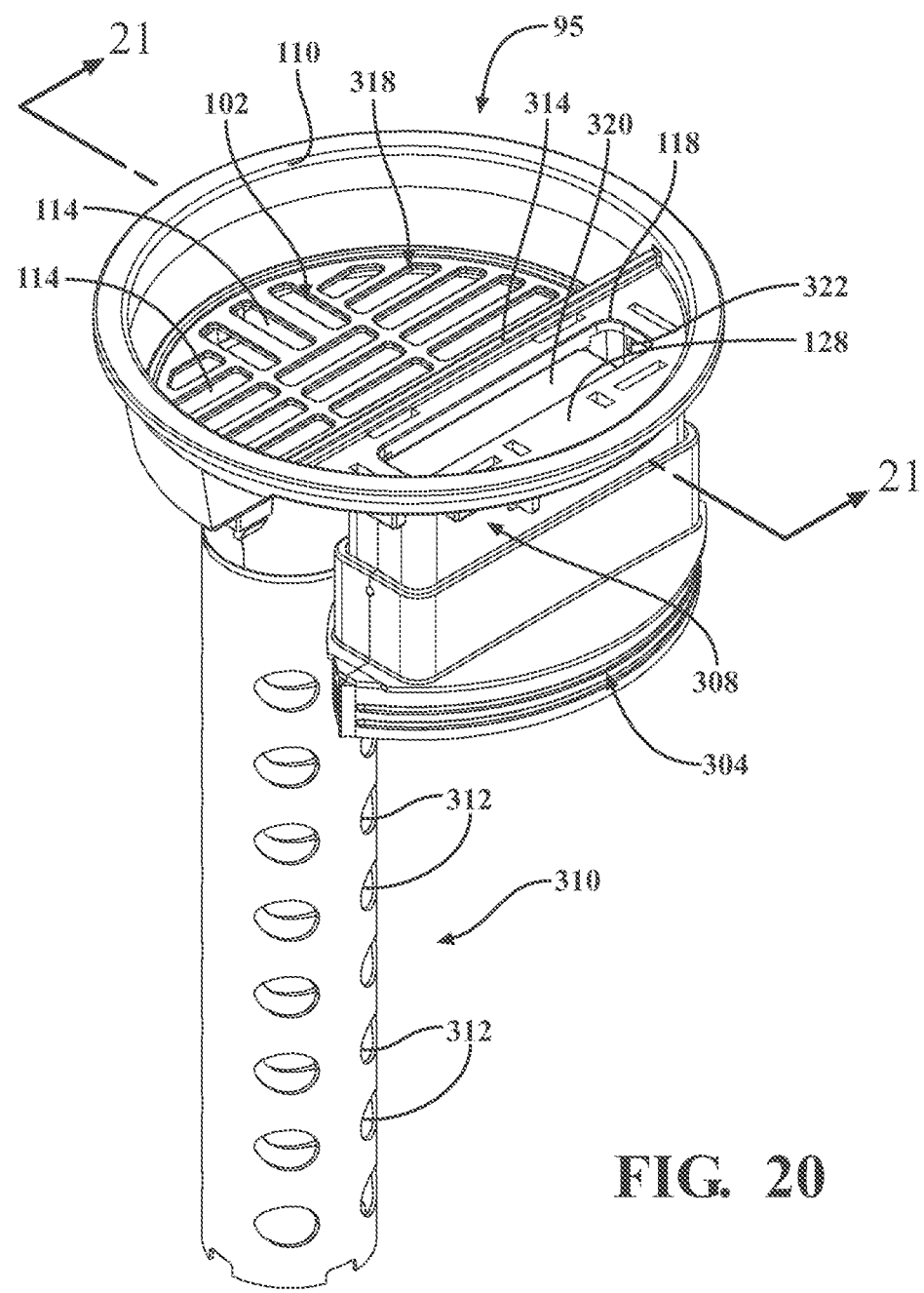
FIG. 20 is a top perspective view of a diverter for the waste receiver of FIG. 18.
Figure 21:
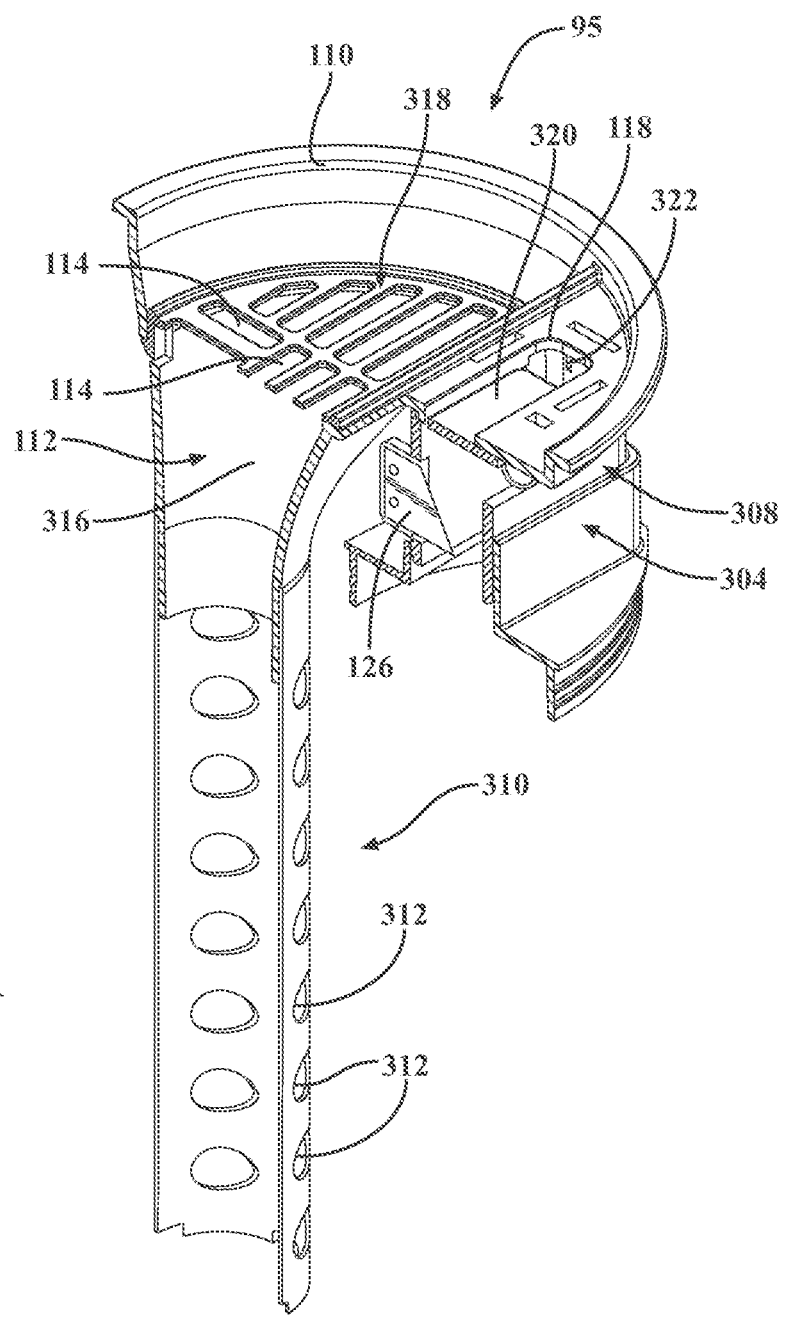
FIG. 21 is a bottom perspective view of the diverter of FIG. 20.

The solid receiver guide 100 and the liquid receiver guide 102 are in communication with the opening 72 of the waste receiver 300 such that the diverter 95 is adapted to accommodate both the solid and liquid phase pharmaceutical waste material that is received within a singular container. Referring to FIGS. 20 and 21, the diverter 95 of FIG. 20 is shown in perspective with the diverter 95 adapted to be coupled to the receiver body 56. The diverter 95 may be pre-assembled as shown for efficient coupling with the receiver body 56 to form the waste receiver 300. A guide coupler 308 to be described may be coupled to the body portion 92, and the bladder adapter 304 may be coupled to the body portion 92. The bladder adapter 304 (and the guide coupler 308, if applicable) may define a portion of the solid receiver guide 100 adapted to direct the solid phase pharmaceutical waste material to the bladder 302. The bladder 302 is coupled to the bladder adapter 304. For the liquid receiver guide 102, a fluid distributor 310 may be coupled to the body portion 92 and in communication with the opening 72. The funnel-type device 112 may be positioned between the body portion 92 and the fluid distributor 310. The body portion 92, the funnel-type device 112, and/or the fluid distributor 310 may define portions of the liquid receiver guide 102. The fluid distributor 310 may include a cylinder comprising the apertures 312 adapted to distribute the liquid waste pharmaceutical material received from the liquid receiver guide 102 to the liquid waste volume 88.

As mentioned, the diverter 95 includes the solid receiver guide 100 and the liquid receiver guide 102. The solid and liquid receiver guides 100, 102 may be spaced apart from one another within the body portion 92 so as to minimize inadvertent placement of solid phase pharmaceutical waste material within the liquid receiver guide 102, and/or liquid phase pharmaceutical waste material within the solid receiver guide 100. The solid and liquid receiver guides 100, 102 may be separated by a ridge 314 with the solid receiver guide 100 positioned on one side of the ridge 314, and the liquid receiver guide 102 positioned on the other side of the ridge 314. The ridge 314 may extend between generally opposing sides of the rim 94 of the diverter 95 as a chord of the circle formed by the rim 94.

The liquid receiver guide 102 may be any suitable structure(s) for directing the liquid phase pharmaceutical waste material to the liquid waste volume 88. The liquid receiver guide 102 includes the inlet 110 defining at least a portion of the liquid receiver guide 102. The funnel-type device 112 may be coupled to or formed integrally with the body portion 92. The funnel-type device 112 may define the inlet 118, and preferably defines at least a portion of the liquid receiver guide 102. The fluid distributor 310 may be coupled to the body portion 92 and in communication with the inlet 110 of the liquid receiver guide 102 (and the opening 72 of the waste receiver). The fluid distributor 310 may be coupled to the funnel-type device 112, or the funnel-type device 112 is formed integrally with and includes a component of the fluid distributor 310.

An inclined surface 316 may be positioned adjacent the ridge 314 with the inclined surface 316 defining a portion of the liquid receiver guide 102. The inclined surface 316 guides the liquid phase pharmaceutical waste material towards the fluid distributor 310, and narrows the size of the liquid receiver guide 102 to prevent ingress of devices that may be used to retrieve the pharmaceutical waste material and/or egress of the liquid phase pharmaceutical waste material from the liquid receiver guide 102. A screen 318 may be provided within the liquid receiver guide 102 to impede ingress of solid phase pharmaceutical waste material into the liquid waste volume 88. The screen 318 is D-shaped and recessed within the liquid receiver guide 102. The apertures 114 may be formed within the screen 318 in the manner shown in FIGS. 20 and 21.

The inlet 118 of the solid receiver guide 100 may be disposed within the upper wall 128. The inlet 118 of the solid receiver guide 100 is preferably sized to permit insertion of patches without excess clearance so as to limit the extent to which the patches may be retrieved. FIGS. 18-21 show the inlet 118 as being rectangular in shape. The diverter 95 may include a cutting element 126, such as the blade, coupled to the body portion 92. The cutting element 126 is disposed proximate the inlet 118 of the solid receiver guide 100 and positioned at least partially within the solid receiver guide 100. The cutting element 126 is adapted to score a patch upon insertion of the patch into the solid receiver guide 100. The cutting element 126 may be coupled to the body portion 106 through riveting, interference fit, adhesives, and other joining means.

A patch plunger (not shown) may be provided to be used to insert patches into the solid receiver guide 100 and ensure proper scoring by the cutting element 126. The patch plunger may include a unitary structure formed from a durable plastic or other suitable material. The patch plunger includes legs separated by a slot sized to receive the cutting element 126. Among other advantages, receiving the cutting element 126 within the slot permits the patch plunger to be inserted into a greater distance within the solid receiver guide 100, thereby increasing the likelihood that the patch descends into the solid waste volume 86, such as the bladder 302.

Referring again to FIGS. 20 and 21, the diverter 95 may include a barrier 320 movably coupled to the body portion 92 with the barrier 320 movable from an open configuration to permit insertion of the solid phase pharmaceutical waste material within the solid receiver guide 100, and a closed configuration to prevent the insertion of the solid phase pharmaceutical waste material within the solid receiver guide 100. The barrier 320 may include a rigid flap pivotally coupled to the body portion 92 and positioned above, within, and/or below the inlet 118 defining a portion of the solid receiver guide 100. An elastic member (not shown), such as a torsion spring, is coupled to the body portion 92 and the barrier 320 such that the barrier 320 is biased to the closed configuration shown in FIGS. 20 and 21. The elastic member is designed with a spring constant such that the forces typically associated with a user inserting the solid phase pharmaceutical waste material (e.g., patches) is sufficient to overcome the biasing force from the elastic member 118. The barrier 320 may be smaller than the solid receiver guide 100 to define a pill opening 322. The pill opening 322 is adjacent the barrier 320 when the barrier is in the closed configuration shown in FIGS. 20 and 21. The pill opening 322 is sized to permit the passage of very small solid phase pharmaceutical waste material, particularly pills and capsules, without permitting passage of larger solid phase pharmaceutical waste material. With the solid receiver guide 100 defining the pill opening 322 adjacent the barrier 320 in the closed configuration, pills and capsules may be quickly inserted into the pill opening 322 without having to forcibly move the barrier 320 to the open configuration. At the same time, the barrier 320 remains in the closed configuration preventing ingress of larger solid phase pharmaceutical waste material unless the user elects to do so.

The diverter 95 may include the orifices 202 (not shown) providing fluid communication between the solid waste volume 86 and the liquid waste volume 88 otherwise separated from one another through means previously described (e.g., the partition 104, the bladder 302, etc.). For example, the orifices extend through the bladder adapter 304. In the manner previously explained in detail, the waste receiver 300 may be manually repositioned, such as inverted, such that the liquid contents within the solid waste volume 86 descend under the influence of gravity to pass through the orifices into the liquid waste volume 88 to perform the self-contained solidification method.

Referring now to FIGS. 22-25, a waste receiver 330 in accordance with another exemplary embodiment is shown. The waste receiver 330 is, at least in many respects, similar to the embodiments of the waste receiver 52, 290, 300 previously described with like numerals identifying like components. Certain structures common between the embodiments may be introduced only briefly in the interest of brevity.

The waste receiver 330 is adapted to be releasably secured to a fixed surface with the locking assembly 54 previously described to minimize or prevent unauthorized personnel from removing the waste receiver 330 from its service location. The waste receiver 330 includes the receiver body 56 with at least the inner surface 59 defining the container volume 58 (see FIGS. 5A, 5B and 6), and the outer surface 60 opposite the inner surface 59. The inner surface 59 and the outer surface 60 cooperate to define at least one wall forming the receiver body 56. The wall(s) may include the front wall 62 opposite the rear wall 64, the top wall 66 opposite a bottom wall 68, and one or more sidewalls 70 extending between the top and bottom walls 66, 68. The receiver body 56 defines the opening 72 in fluid communication with the container volume 58, and the opening 72 receives the pharmaceutical waste material to be disposed within the container volume 58.

The waste receiver 330 may advantageously accommodate disposal of both the solid phase pharmaceutical waste material and the liquid phase pharmaceutical waste material in the single receiver body 56 of substantially unitary construction. The container volume 58 may be further defined by a solid waste volume 86 and a liquid waste volume 88 substantially separate from the solid waste volume 86 (see FIGS. 5A and 6). Each of the solid and liquid waste volumes 86, 88 are in communication with the opening 72 of the receiver body 56. As a result, the user may dispose of one or both of the solid and liquid phase pharmaceutical waste material through the opening 72 and into the receiver body 56 with each phase of the pharmaceutical waste material to be diverted to its respective waste volume 86, 88 for suitable treatment. The diverting or directing one or both of the solid and liquid phase pharmaceutical waste material through the opening 72 to its respective waste volume 86, 88 may be facilitated with the diverter 90 of the waste receiver 330. The diverter 90 may comprise the solid receiver guide 100 adapted to direct the solid phase pharmaceutical waste material to the solid waste volume 86, and the liquid receiver guide 102 to direct the liquid phase pharmaceutical waste material to the liquid waste volume 88. The solid receiver guide 100 may include one or more of the inlet 118, the pushing member 120, the gripping member 122, the funnel member 124, and the cutting element 126 previously described with each of their respective structural and functional features hereby incorporated by reference. The waste disposal system 50 may include the indicator 196 suitably positioned on the receiver body 56 to come into contact with the liquid phase pharmaceutical waste material when a level of the liquid phase pharmaceutical waste material is above a predetermined level, for example, nearing the capacity of the container volume 58.

With continued reference to FIGS. 22-25, the receiver body 56 of the waste receiver 330 defines the lock passageway 230. The outer surface 60 defines the lock passageway 230 such that the lock passageway 230 may be considered separate from the opening 72 of the receiver body 56. More particularly the front wall 62 of the receiver body 56 may define an aperture 232, and the rear wall 64 of the receiver body 56 may define another aperture 234 with apertures 232, 234 opening into or at least define a portion of the lock passageway 230 such that the receiver body 56 may surround the lock passageway 230. The lock opening 230 may be generally centered through the receiver body 56 in a front-to-back direction.

Figure 23:
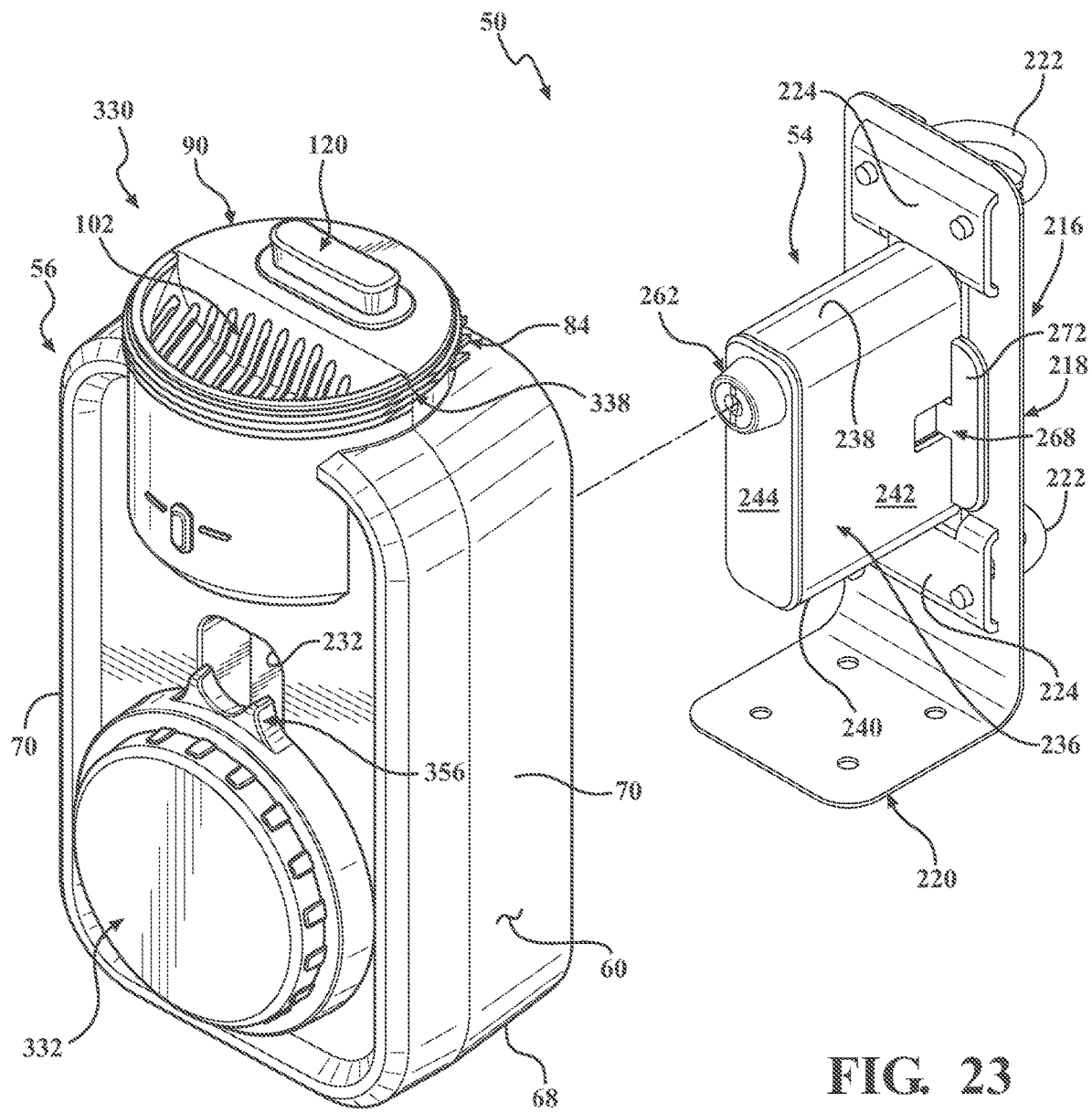
FIG. 23 is an exploded front perspective view of the waste disposal system of FIG. 22.
Figure 24:
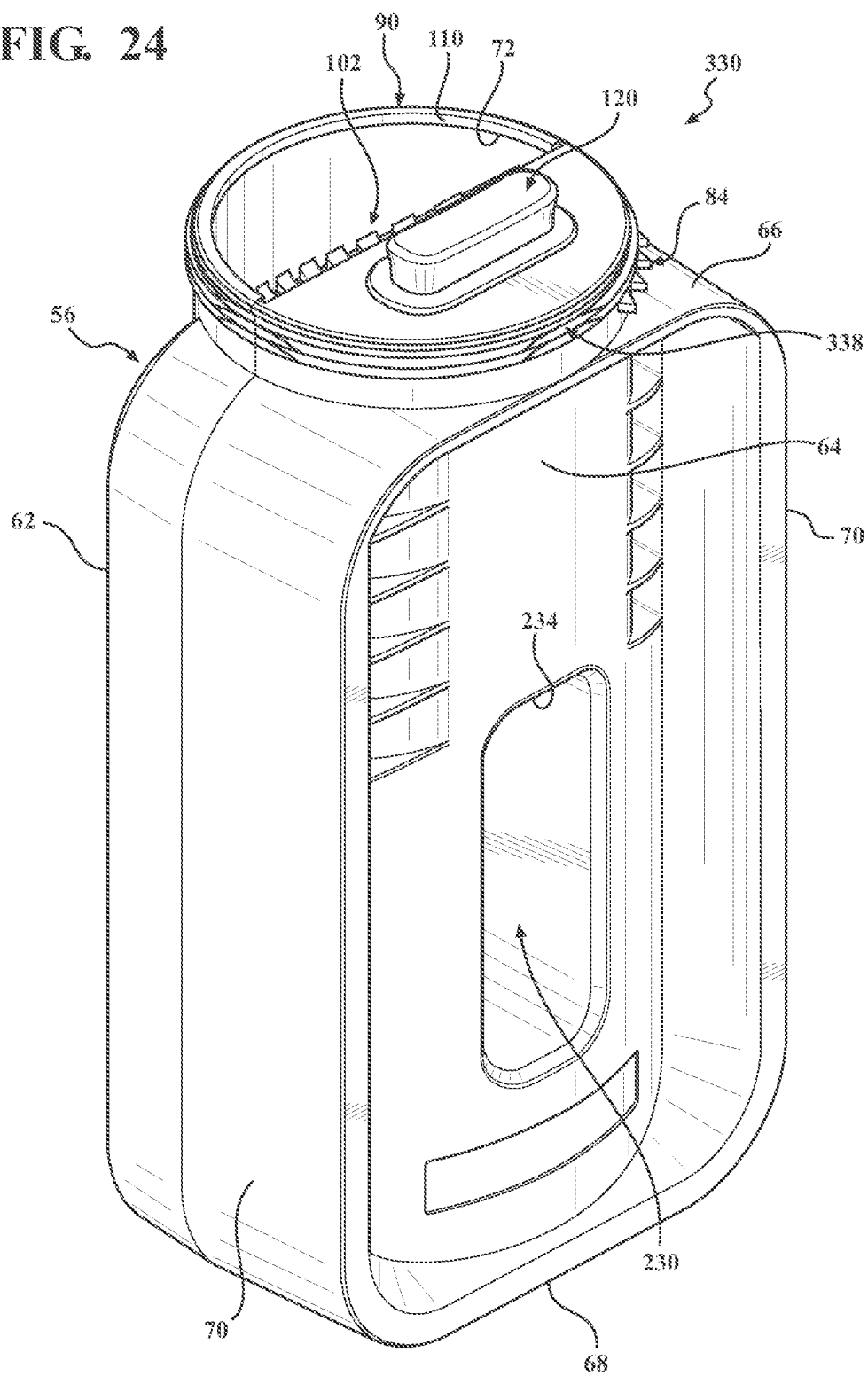
FIG. 24 is a rear perspective view of the waste disposal system of FIG. 22.

The locking assembly 54 includes the lock housing 236 sized to be removably positioned at least partially within the lock passageway 230. With reference to FIG. 23, the lock housing 236 includes a top wall 238 opposing a bottom wall 240, opposing sidewalls 242 extending between the top and bottom walls 238, 240. A front wall 244 extends between the top, bottom, and opposing sidewalls 238, 240, 242, and the front wall 244 may be oblong corresponding to the apertures 232, 234 that are oblong. The complementary oblong shapes of the lock housing 236 and the lock passageway 230 facilitate orienting and securing the waste receiver 330 to the locking assembly 54, and thus to the fixed surface, in a single orientation. Further, with the waste receiver 330 coupled to the locking assembly 54, the top, bottom, and opposing sidewalls 238, 240, 242 of the lock housing 236 is surrounded in the lock passageway 230 with the front wall 244 positioned near the aperture 232 and accessible to the user for actuating the locking assembly 54 in a manner to be described.

The locking assembly 54 may include an engagement feature 246 movably coupled to the lock housing 236 (see FIG. 13). The receiver body 56 is positioned such that the lock passageway 230 and the lock housing 236 are in alignment, and the engagement feature 246 is at least partially extending through the keyway 250. The waste disposal system 50 may be considered in a locked configuration in which the engagement feature 246 is moved to prevent the waste receiver 330 from being decoupled from the locking assembly 54.

With continued reference to FIG. 23, the locking assembly 54 includes the lock cylinder 262. An input to the lock cylinder 262 may actuate the locking assembly 54 between the locked configuration and an unlocked configuration to be described. To facilitate efficient decoupling of the waste receiver 330 from the locking assembly 54, the locking assembly 54 may include the decoupling member 268 coupled to and movable relative to the lock housing 236. The decoupling member 268 is configured to move the waste receiver 330 away from the fixed surface upon the locking assembly 54 entering the unlocked configuration. More particularly, the decoupling member 268 is biased away from the bracket 216 secured to the fixed surface with the decoupling member 268 automatically moving the waste receiver 330 from a first distance from the bracket 216 to a second distance from the bracket 216 greater than the first distance. In the locked configuration, the biasing members 274 are resiliently deformed and are prevented from resiliently returning based on the engagement of the engagement features 246 with the receiver body 56. As the locking assembly 54 is moved from the locked configuration to the unlocked configuration, the disengagement of the protrusion 256 and the keyway 250 no longer prevent the biasing members 274 from moving the decoupling member 268. The biasing members 274 resiliently move the decoupling member 268 and thus the waste receiver 330 to the second distance greater than the first distance.

Figure 26:
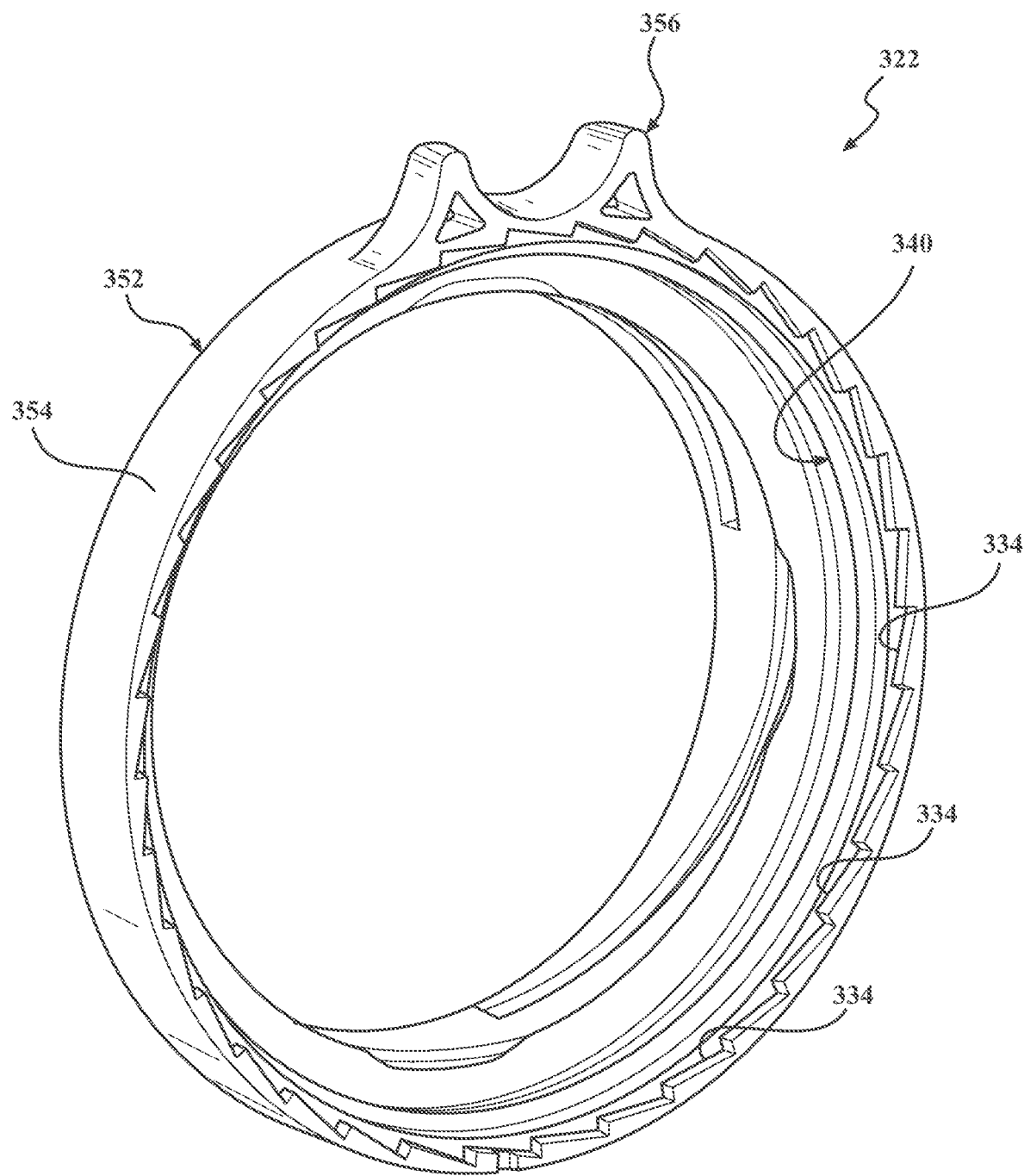
FIG. 26 is a rear perspective view of a cover.

The waste receiver 330 of the waste disposal system 50 includes a cover 332, which in at least some respects is similar to the cover 82 previously described. The cover 332 couples with the receiver body 56 over the opening 72 to seal the pharmaceutical waste material within the container volume 58, and in particular prior to disposal of the waste receiver 330. With concurrent reference to FIG. 26, the waste receiver 330 may include one or more coupling features 84 for receiving complementary coupling features 334 of the cover 82 in a manner that renders the waste material irretrievable. The coupling features 84 may include teeth suitably positioned engage complementary teeth 334 disposed on an underside of the cover 332. The teeth 84, 334 are shaped to permit rotation of the cover 332 relative to the receiver body 56 in a single direction. As a result, once it is desired to seal the pharmaceutical waste material within the container volume 58 prior to disposal, the cover 332 is irreversibly coupled with the receiver body 56 with the coupling features 84, 334. After the sealing of the waste receiver 330 by a user with authorization to do so, the pharmaceutical waste material is irretrievable to those within the subsequent chain of custody of the waste receiver 330.

Figure 25:
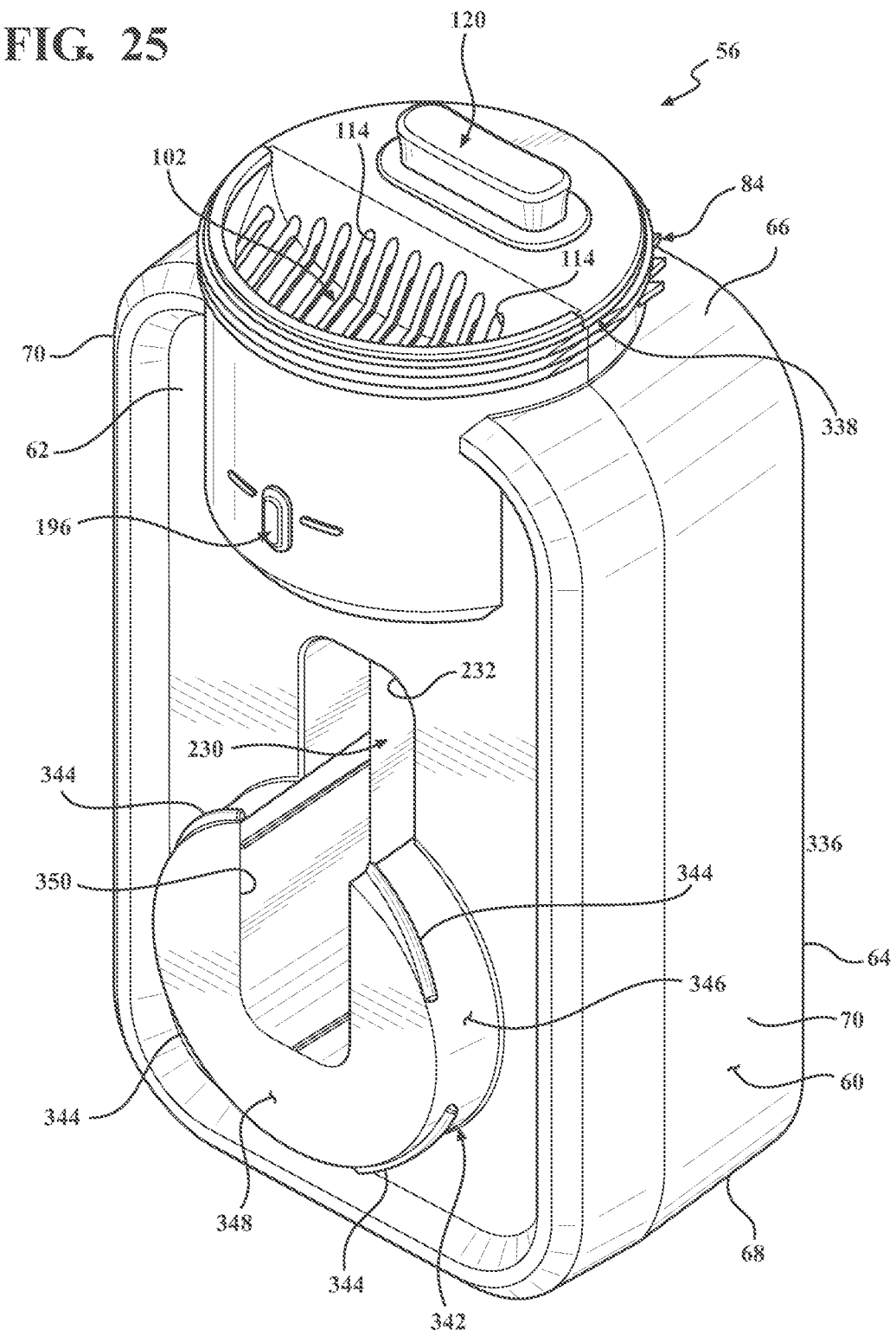
FIG. 25 is a front perspective view of a waster receiver of the waste receiver of FIG. 22.

The waste receiver 330 may include a first cover retention feature 336 and a second cover retention feature 338. The second cover retention feature 338 may be threads near the opening 72 that are configured to receive complementary threads 340 disposed on the underside of the cover 332. The second cover retention feature 338 may cooperate with complementary coupling features 340 to seal the pharmaceutical waste material within the container volume 58. With particular reference to FIG. 25, the first cover retention feature 336 may be coupled to the front wall 62 of the receiver body 56. The first cover retention feature 336 may include a boss 342 extending forward from the front wall 62, and threads 344 disposed on an outer surface 346 of the boss 342. FIG. 25 shows a plurality of threads 344 circumferentially spaced about the outer surface 346 of the boss 342. As a result, when the cover 332 threadably coupled to the first cover retention feature 336 prevents axial decoupling of the cover 332 from the receiver body 56. The boss 342 of FIG. 25 may be considered a generally U-shaped protrusion defined between the outer surface 346 and a front surface 348 of the boss 342. A slot 350 defined between opposing sides of the generally U-shaped protrusion is in communication with the lock passageway 230, or stated differently the lock passageway 230 extends through and is at least partially defined by the boss 232.

Figure 22:
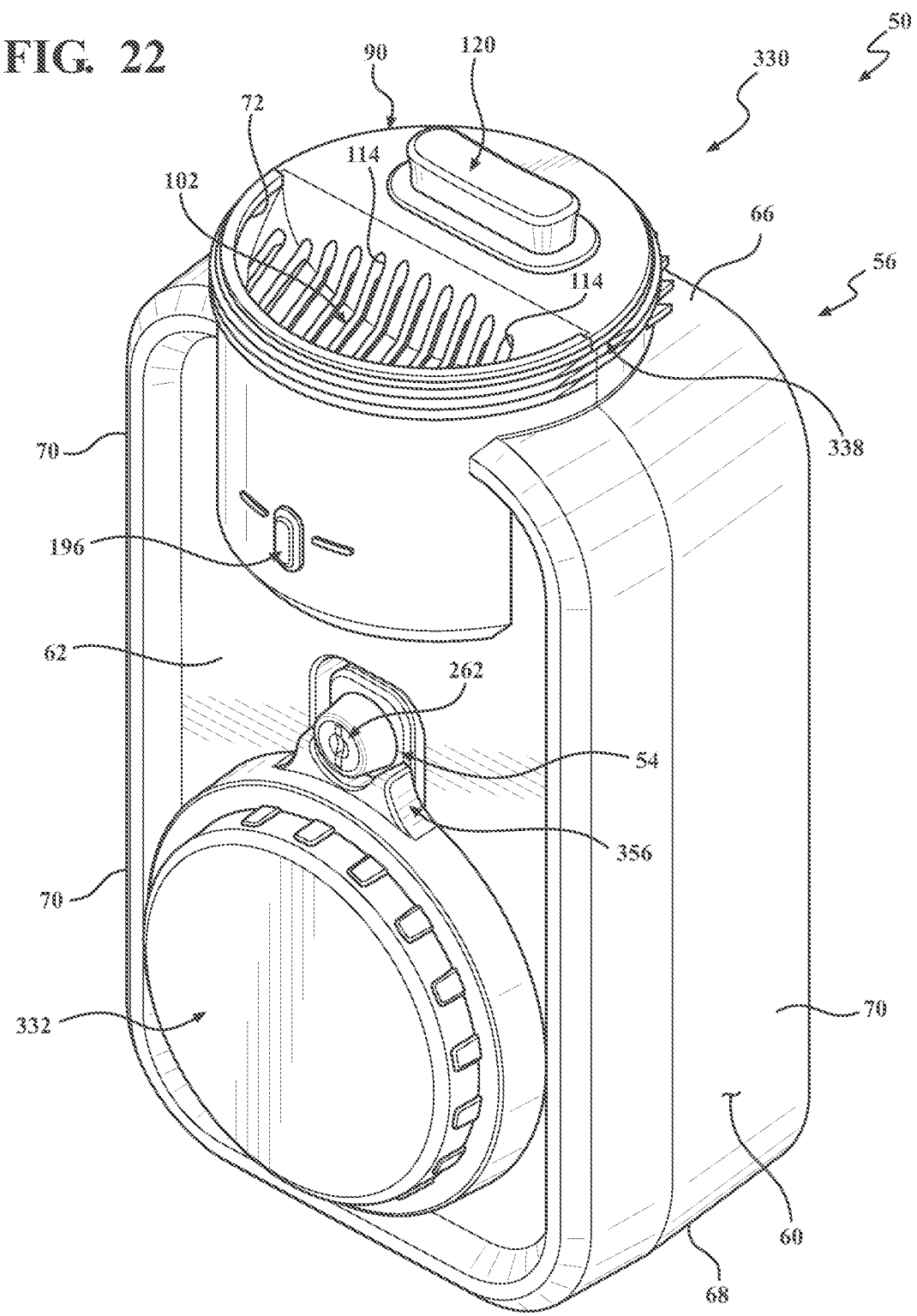
FIG. 22 is a perspective view of a waste disposal system including a waste receiver and a locking assembly.

The cover 332 may include a cover body 352, and a rim 354 defining an outer surface or periphery of the cover body 352. A locking feature 356 may be coupled to the rim 354 such that the locking feature 356 extends radially outwardly from the rim 354. The locking feature 356 may be a U-shaped flange configured to receive the lock cylinder 262 of the locking assembly 54 between upstanding ends of the U-shaped flange, as shown in FIG. 22. The engagement between the locking feature 356 and the lock cylinder 262 prevents rotational decoupling of the cover 332 from the locking assembly 54 when the waste receiver 330 is releasably secured to the locking assembly 54 in the locked configuration to be described. The cover body 352 may define a concave cavity with a depth at least equal to a length or thickness of the boss 342 extending from the front wall 62 of the receiver body 56. The arrangement permits the cover 332 to be nested in abutment with the front wall 62 of the receiver body 56 such that the locking feature 356 is positioned adjacent the lock passageway 230 when the cover 332 is coupled to the receiver body 56 (and thus permitting engagement of the lock cylinder 262).

Exemplary methods of disposing of the waste receiver 330 may include the waste system 50 initially in the locked configuration, as shown in FIG. 22, with the locking assembly 54 positioned at least partially within the lock passageway 230 of the waste receiver 330. In the locked configuration, the engagement feature 248 of the locking assembly 54 engages the keyway 250 to prevent the waste receiver 330 from being decoupled from the locking assembly 54. The biasing member 274 is in a stored energy state in the locked configuration. Furthermore, the lock cylinder 262 extends forward of the front (e.g., the front wall 62) of the receiver body 56 by a first distance in the locked configuration such that the lock cylinder 262 engages the locking feature 356 of the cover 332. As a result, the cover 332 may not be decoupled from the receiver body 56 in the locked configuration, as rotational decoupling is prevented by the engagement of the lock cylinder 262 and the locking feature 356, and axial decoupling is prevented by the engagement of the first cover retention feature 336 (e.g., the threads 344 on the outer surface 346 of the boss 342 and the complementary threads 340 of the cover 332).

The actuating of the locking assembly 54 may include the lock cylinder 262 receives the input from the user, for example, insertion and turning of a key. The engagement feature 246 is moved to disengage from the receiver body 56, more particularly moving out of engagement with the keyway 250. The locking assembly 54 may be considered to be in the unlocked configuration in which the engagement feature 246 has been moved to permit the waste receiver 330 to be decoupled from the locking assembly 54. Moreover, the receiver body 56 is moved away from the fixed surface to disengage the locking assembly 54 from the cover 332. In particular, the decoupling feature 268 moves the waste receiver 330 away from the fixed surface once the locking assembly 54 is moved to the unlocked configuration. The magnitude of the movement may be at least greater than an amount that the lock cylinder 262 extends from the front wall 244 of the lock housing 236. The first cover retention feature 336 may maintain the coupling between the cover 332 and the receiver body 56 subsequent to the receiver body 56 being moved away from the fixed surface.

Once moving the locking assembly 54 from the locked configuration to the unlocked configuration, the cover 332 may now be considered removably coupled with the first cover retention feature 336. Owing to the receiver body 56 being moved away from the fixed surface by a distance greater than the lock cylinder 262, the locking feature 356 of the cover 332 is likewise moved forward of the lock cylinder 262. An input may be provided to the cover 332 to decouple the cover 332 the first cover retention feature 336. In one example, the cover 332 is rotated relative to the receiver body 56 in which the threads 340 of the cover 332 are disengaged from the threads 344 of the first cover retention feature 336. The step of decoupling the cover 332 from the first cover retention feature 336 may be performed while the receiver body 56 is supported on the locking assembly 54 (i.e., the lock housing 236 remains at least partially positioned within the lock passageway 230).

The cover 332 may be coupled with the receiver body 56 over the opening 72 to seal the pharmaceutical waste material within the receiver body 56, and more particularly within the container volume 58. The cover 332 may be coupled to the second cover retention feature 338 positioned near the opening 72. For example, the threads near the opening 72 are threadably engaged with complementary threads 340 of the cover 332. Further, the coupling features 334 of the cover 332 engage the coupling features 84 to irreversibly couple the cover 332 with the receiver body 56. The step of coupling the cover 332 from the second cover retention feature 338 may be performed while the receiver body 56 is supported on the locking assembly 54 (i.e., the lock housing 236 remains at least partially positioned within the lock passageway 230). The waste receiver 330 may be removed from the locking assembly 54, and the waste receiver 330 may be disposed of in a suitable manner.

Exemplary methods may further include providing a second waste receiver, which may be the same or similar to the waste receiver 330 previously removed. As such, the second waste receiver includes a second cover and a second receiver body defining a second lock passageway. The lock housing 236 may be positioned within the second lock passageway to couple the second receiver body and the locking assembly 54 such that the engagement feature 246 engages the second receiver body. The second cover may be coupled to the second receiver body prior to and during the step of positioning the lock housing 236 within the second lock passageway. The locking assembly 54 may be actuated from the unlocked configuration to the locked configuration in manners previously described, which concurrently secures the second cover to the second receiver body. The second waste receiver is readied for operational duty.

As mentioned and relevant to each of the waste receivers 52, 290, 300, 330, the chemical composition 190 may be positioned within the liquid waste volume 88 in any number of arrangements. In one example, one or more levels of the fluid absorber 193 may be arranged vertically within the liquid waste volume 88 with the liquid phase pharmaceutical material being directed to the levels. The liquid phase pharmaceutical material may more rapidly be absorbed by the fluid absorber 193, which inhibits puddling or ponding of liquid phase pharmaceutical material within the liquid waste volume 88. Likewise, the positioning of the reaction agent 194 may be varied. For example, the reaction agent 194 may be positioned (i) as a reaction agent layer somewhat adjacent to the liquid receiver guide 102, e.g., the liquid phase pharmaceutical waste material will pass through a reaction agent layer after passing through the liquid receiver guide 102 and before the liquid phase pharmaceutical waste material comes into contact with the fluid absorber 193; (ii) as a reaction agent layer positioned near the bottom wall 68 of the receiver body 56 or at another suitable location such that the liquid phase pharmaceutical waste material may react with the reaction agent 194 prior to coming into contact with the fluid absorber 193; and/or (iii) as one or more reaction agent layers that are positioned spaced apart from one another within and/or somewhat adjacent to the fluid absorber 193 such that the liquid phase pharmaceutical waste material may react with the reaction agent 194 prior to being converted to a gelatenous or solid material and subsequently retained within the fluid absorber 193.

Other designs, configurations, arrangements, and the like, of the receiver body 56 of the waste receiver 52, 290, 300, 330 are contemplated. For example, the solid and liquid waste volumes 86, 88 may be arranged in a generally side-by-side configuration within the receiver body 56. In another example, the solid and liquid waste volumes 86, 88 may be arranged in a generally vertical configuration within the receiver body 56. A first compartment within the receiver body is positioned adjacent the bottom wall 68, and a second compartment is positioned adjacent the upper wall 66. The first and second compartments may be at least partially separated by a transition section having an aperture such that the second compartment is in communication with the opening 72 of the waste receiver 52, 290, 300, 330. The first compartment may define the solid waste volume 86, and the second compartment may define the liquid waste volume 88, or vice versa.

The waste receiver 52, 292, 300, 330 may include one or more electronic controls to facilitate advanced operations of the waste disposal system 50. The waste disposal system may include one or more of a controller and an input device and/or an output device in electronic communication with the controller. The input device may include a keypad or a touch-screen utilized by a user to input certain relevant information (e.g., drug classification) that may be communicated to the controller for further processing. The input device may receive, store and/or transmit, information regarding the type of waste that is being deposited into the waste receiver 52, 292, 300, 330. Additionally or alternatively, the input device may be used to identify and/or authenticate a user for access to the waste disposal system 50. The user may type a passcode or other authentication information into the input device. Other types of authentication protocols may be included, such as a badge scanner or barcode reader. The input device may also provide security measures by receiving authentication information such as a passcode, fingerprints, voice recognition, and the like. The design of the input device may be varied to suit the design requirements of the waste disposal system 50. The output device may display certain relevant information to the user. The output device is in electronic communication with the controller and adapted to display information such as current fill level(s) of the waste receivers, expiration dates of the waste receivers, time remaining prior to expiration, the types of waste that have previously been deposited into the waste receivers, user input information, drug classifications, remaining battery life, alert information, and any other relevant information that could possibly be utilized by a user of the waste disposal system 50. The output device may provide specific information regarding the status of the waste receiver 52, 292, 300, 330, including but not limited to a length of time of the operational lifecycle of the waste receiver 52, 292, 300, 330, an expiration date for the waste receiver 52, 292, 300, 330, and/or any other useful information depending upon the design requirements of the waste disposal system 50.

The waste disposal system 50 may also include a monitoring device (not shown), such as a video and/or audio recorder. The monitoring device may be utilized to monitor and/or record video and/or audio of the usage of the waste disposal system 50. A real-time and/or previously recorded video and/or audio feed may be stored in memory of the controller or remote from the waste disposal system 50. In one example, the monitoring device is disposed on the locking assembly 54, for example, on the front wall 244 of the lock housing 236.

The waste disposal system 50 may include an identification reader (not shown) in communication with the controller configured to read an identification tag associated with the waste receiver 52, 290, 300, 330. In one example, the identification reader is disposed on the locking assembly 54, for example, on the front wall 244 of the lock housing 236. Exemplary identification tags may include a radio frequency identification ("RFID") tag, a barcode label, a quick response (QR) code, a printed serial number, an integrated circuit, and the like. The RFID tag may include an active RFID tag, which may contain a battery and may transmit signals autonomously, a passive RFID tag, which may have no battery and may require an external source to provoke signal transmission, or a battery assisted passive (BAP) RFID tag, which may require an external source to wake up but have significantly higher forward link capability providing greater range, among others. Functionality based on the identification reader reading the identification tag may include transmitting a signal to the controller once the waste receiver 52, 290, 300, 330 is properly coupled with the locking assembly 54. For another example, read, write, and/or rewrite information from and/or to the identification tag on the waste receiver 52, 290, 300, 330, for example, so that a particular the waste receiver 52, 290, 300, 330 cannot be used more than once. The identification reader may read the information unique to a particular one of the waste receiver 52, 290, 300, 330, and should the same identification tag be later detected, the controller may activate one of the indicators to provide an alert to the user. Still another example includes the controller receiving information from the identification reader to track location, shipment and/or delivery of the waste receiver 52, 290, 300, 330 to one of a permanent disposal site, locations within a hospital, or other suitable locations.

Exemplary Clauses:

Clause 1: A diverter adapted to be coupled to a receiver body for receiving solid phase pharmaceutical waste material and liquid phase pharmaceutical waste material with the solid phase pharmaceutical material including a patch of material, the diverter including: a body portion; a solid receiver guide coupled to the body portion and adapted to direct the solid phase pharmaceutical waste material to a solid waste volume; a retainer cap adapted to seal the solid phase pharmaceutical waste material within the receiver body for disposal of the receiver body; and a cutting element coupled to the body portion and disposed at least partially within the solid receiver guide with the cutting element positioned to cut the patch upon insertion into the solid receiver guide.

Clause 2: The diverter of clause 1, wherein the solid receiver guide is elongate with the cutting element oriented substantially perpendicular to the elongate solid receiver guide.

Clause 3: The diverter of clause 1, further including a fluid distributor coupled to the body portion and in communication with the liquid receiver guide with the flow distributor including a plurality of apertures adapted to distribute the liquid waste pharmaceutical material from the liquid receiver guide to the liquid waste volume.

Clause 4: The diverter of clause 1, further including a bladder coupled to the solid receiver guide and adapted to receive the solid phase pharmaceutical waste material.

Clause 5: The diverter of clause 1, further including a barrier coupled to the body portion with the barrier movable from an open configuration to permit insertion of the solid phase pharmaceutical waste material within the solid receiver guide and a closed configuration to prevent the insertion of the solid phase pharmaceutical waste material within the solid receiver guide with the barrier biased to the closed configuration.

Clause 6: The diverter of clause 5, wherein the barrier is smaller than the solid receiver guide with the solid receiver guide defining a pill opening adjacent the barrier in the closed configuration.

Clause 7: The diverter of clause 1, further including a liquid receiver guide coupled to the body portion and adapted to direct the liquid phase pharmaceutical waste material to a liquid waste volume with the retainer cap adapted to seal the solid phase pharmaceutical waste material and the liquid phase pharmaceutical waste material within the receiver body for disposal of the receiver body.

Clause 8: A waste receiver for receiving solid phase pharmaceutical waste material and liquid phase pharmaceutical waste material, the waste receiver including: a receiver body defining a fixed volume; and a bladder disposed within the receiver body and adapted to receive the solid phase pharmaceutical waste material, wherein the receiver body is adapted to accommodate a liquid waste volume within the receiver body separate from the bladder with the liquid waste volume defined by a difference between the fixed volume of the receiver body and the bladder.

Clause 9: The waste receiver of clause 8, further including a retainer cap adapted to seal the solid phase pharmaceutical waste material and the liquid phase pharmaceutical waste material within the receiver body for disposal of the waste receiver.

Clause 10: The waste receiver of clause 8, further including a solid receiver guide disposed within the receiver body with the bladder coupled to the solid receiver guide.

Clause 11: The waste receiver of clause 10, further including a liquid receiver guide disposed within the receiver body external to the bladder.

Clause 12: The waste receiver of clause 8, further including a reaction agent disposed within the bladder and adapted to alter the solid phase pharmaceutical waste material received within the bladder.

Clause 13: The waste receiver of clause 8, further including a fluid absorber disposed within the receiver body external the bladder with the fluid absorber adapted to expand and absorb the liquid phase pharmaceutical waste material received within the liquid waste volume.

Clause 14: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element positioned within the solid receiver volume to cut the solid phase pharmaceutical waste material; and a pushing member movably disposed within the solid receiver guide and including a main body defining a handle, and a leg extending from the main body opposite the handle with the handle adapted to receive an input from a user to move the pushing member between a first position in which the main body is spaced from solid receiver guide to provide a window partially defined between the main body, the leg, and the solid receiver guide for receiving the solid phase pharmaceutical waste material, and a second position in which the main body is adjacent to the solid receiver guide to facilitate engagement of the solid phase pharmaceutical waste material with the cutting element.

Clause 15: The waste receiver of clause 14, wherein at least a portion of the leg of the pushing member is disposed within the solid waste volume when the pushing member is in the first and second positions.

Clause 16: The waste receiver of clauses 14 or 15, wherein the pushing member further includes a foot extending from the leg with the foot adapted to interfere with the solid receiver guide as the pushing member is in the first position to prevent the pushing member from decoupling from the waste receiver.

Clause 17: The waste receiver of any of clauses 14-16, wherein the pushing member further includes a gripping member coupled to the main body and adapted to engage a patch including the solid phase pharmaceutical waste material positioned within the window and the pushing member is moved from the first position to the second position.

Clause 18: The waste receiver of any of clauses 14-17, wherein the main body of the pushing member further defines a first portion and a second portion spaced apart from one another to define a slot therebetween with the slot sized to receive the cutting element.

Clause 19: The waste receiver of any of clauses 14-18, wherein the solid receiver guide defines an elongate opening with the cutting element oriented substantially perpendicular to the elongate opening.

Clause 20: The waste receiver of any of clauses 14-19, wherein the solid waste guide further includes a funnel member including a plurality of sections each including an inclined surface and spaced apart from one another to define a first gap positioned above the cutting element such that the funnel member is adapted to guide the solid waste material along the inclined surfaces towards the first gap to position the solid phase waste material directly above an edge of the cutting element.

Clause 21: The waste receiver of clause 20, wherein the plurality of sections are spaced apart from one another to define a second gap with the pushing member adapted to be slidably moved through the second gap as the pushing member moves from the first position to the second position, thereby facilitating the solid waste material moving through the first and second gaps and into engagement with the cutting element.

Clause 22: The waste receiver of any of clauses 14-21, further including a liquid receiver guide coupled to the receiver body and adapted to direct the liquid phase pharmaceutical waste material to a liquid waste volume within the container volume separate from the solid waste volume.

Clause 23: The waste receiver of clause 22, further including a cover adapted to be removably coupled with the receiver body to seal the solid phase pharmaceutical waste material and the liquid phase pharmaceutical waste material within the receiver body for disposal of the waste receiver.

Clause 24: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element coupled to the solid receiver guide and disposed within the solid waste volume, wherein the solid receiver guide includes a funnel member defining a first gap above the cutting element; and a pushing member movably disposed within the solid receiver guide and adapted to receive and input and move the solid phase pharmaceutical waste material through the solid receiver guide with the pushing member including a main body defining a handle to receive the input, and a gripping member coupled to the main body, wherein the gripping member is adapted to impale a patch including the solid phase pharmaceutical waste material and retain the patch as the main body moves the patch through the first gap and into engagement with the cutting element.

Clause 25: The waste receiver of clause 24, wherein the gripping member is a spike.

Clause 26: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume in fluid communication with the opening; a solid receiver guide coupled to the receiver body and adapted to direct the solid phase pharmaceutical waste material to a solid waste volume within the container volume; a cutting element coupled to the solid receiver guide and disposed within the solid waste volume; and a pushing member movably disposed within the solid receiver guide and adapted to facilitate moving the solid phase pharmaceutical waste material through the solid receiver guide, wherein the solid receiver guide includes a funnel member including a plurality of flexible sections spaced apart from one another to define a first gap above the cutting element, and a second gap smaller than a thickness of the main body of the pushing member adapted slidably move through the second gap with the flexible sections adapted to resiliently deflect away from the pushing member as the main body moves the solid phase pharmaceutical waste material through the first and second gaps and into engagement with the cutting element.

Clause 27: The waste receiver of clause 26, wherein each of the flexible sections includes an inclined surface with the inclined surfaces oriented towards one another to guide the solid waste material towards the first gap to position the solid phase waste material directly above an edge of the cutting element.

Clause 28: The waste receiver of clauses 26 or 27, wherein the second gap is perpendicular to the first gap.

Clause 29: The waste receiver of any of clauses 26-28, wherein the funnel member is symmetric about the first gap.

Clause 30: The waste receiver of any of clauses 26-29, wherein the funnel member is symmetric about the second gap.

Clause 31: The waste receiver of any of clauses 26-30, wherein the cutting element is oriented parallel with the first gap.

Clause 32: The waste receiver of any of clauses 26-31, wherein the first and second gaps are sized to be smaller than pills including the solid waste pharmaceutical material such that the pills descend under influence of gravity to be supported on the sections above first gap.

Clause 33: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume a diverter coupled to the receiver body and including: (i) a body portion having a rim positioned adjacent the opening of the receiver body; (ii) a solid receiver guide coupled to the body portion and disposed within the receiver body with the solid receiver guide adapted to direct the solid phase pharmaceutical waste material to a solid waste volume within the container volume; (iii) a liquid receiver guide coupled to the body portion and disposed within the receiver body and adapted to direct the liquid phase pharmaceutical waste material to a liquid waste volume within the container volume with each of the solid receiver guide and the liquid receiver guide being in communication with the opening of the waste receiver; (iv) a partition within the container volume that at least partially separates the liquid waste volume from the solid waste volume; and (iv) at least one orifice within the partition for providing fluid communication between the liquid waste volume and the solid waste volume.

Clause 34: The waste receiver of clause 33, wherein the diverter includes a plurality of walls with one of the walls including the partition within the walls disposed within container volume and defining the solid waste volume that is substantially enclosed and separate from the liquid waste volume other than the at least one inlet.

Clause 35: A waste receiver for receiving a pharmaceutical waste material including at least a solid phase pharmaceutical waste material and a liquid phase pharmaceutical waste material with the waste receiver adapted to be releasably secured to a fixed surface, the waste receiver including: a receiver body defining an opening and including an inner surface defining a container volume: a diverter coupled to the receiver body and including: (i) a body portion having a rim positioned adjacent the opening of the receiver body; (ii) a solid receiver guide coupled to the body portion and disposed within the receiver body with the solid receiver guide defining an inlet and adapted to direct the solid phase pharmaceutical waste material received through the inlet to a solid waste volume within the container volume; (iii) a liquid receiver guide coupled to the body portion and disposed within the receiver body and adapted to direct the liquid phase pharmaceutical waste material to a liquid waste volume within the container volume with each of the solid receiver guide and the liquid receiver guide being in communication with the opening of the waste receiver; and a cover adapted to be coupled with the receiver body over the opening to seal the pharmaceutical waste material within the container with the cover including an inner surface spaced apart from the inlet of the solid receiver guide when the cover is coupled with the receiver body such that at least partially inverting the receiver body directs liquid in the solid waste volume to move through the inlet and the liquid receiver guide and into the liquid waste volume.

Clause 36: A method for preparing for disposal of solid phase pharmaceutical waste material and liquid phase pharmaceutical waste material contained within a waste receiver including a liquid waste volume substantially separate from a solid waste volume containing a liquid and the solid phase pharmaceutical waste material, and an inlet or opening providing fluid communication between the liquid waste volume and the solid waste volume, the method including the step of: manipulating the receiver body such that the liquid within the solid waste volume moves through the inlet or the opening into the liquid waste volume.

Clause 37: The method of clause 36, further including coupling a cover to the receiver body to seal the liquid and the solid phase pharmaceutical waste material within the receiver body with prior to the step of manipulating the receiver body.

Clause 38: The method of clauses 36 or 37, wherein the step of manipulating the receiver body further including at least partially inverting the receiver body to direct the liquid away from a bottom surface of the receiver body and towards the opening.

Clause 39: The method of any of clauses 36-38, further including receiving information from indicia disposed on the waste receiver as to a direction to manipulate the receiver body.

Clause 40: The method of clause 39, wherein the indicia is disposed on one of the diverter and a cover adapted to be coupled to the receiver body prior to the step of manipulating the receiver body.

Clause 41: A waste receiver for receiving solid phase pharmaceutical waste material and liquid phase pharmaceutical waste material, the waste receiver including: a receiver body defining an opening and including an inner surface defining a container volume; a diverter coupled to the receiver body and including: (i) a body portion having a rim positioned adjacent the opening of the receiver body; (ii) a solid receiver guide coupled to the body portion and disposed within the receiver body with the solid receiver guide adapted to direct the solid phase pharmaceutical waste material to a solid waste volume within the container volume; (iii) a liquid receiver guide coupled to the body portion and disposed within the receiver body and adapted to direct the liquid phase pharmaceutical waste material to a liquid waste volume within the container volume and separate from the solid waste volume, wherein the solid receiver guide and the liquid receiver guide are in communication with the opening of the waste receiver; and a cover adapted to cover the opening to seal the solid phase pharmaceutical waste material and the liquid phase pharmaceutical waste material within the receiver body for disposal of the waste receiver.

Clause 42: The waste receiver of clause 41, further including a cutting element coupled to the solid receiver guide with the cutting element and disposed within the solid waste volume with the cutting element positioned to cut the solid phase pharmaceutical waste material being directed through the solid receiver guide.

Clause 43: The waste receiver of clause 42, a pushing member movably disposed within the solid receiver guide and adapted to facilitate moving of the solid phase pharmaceutical waste material through the solid receiver guide and engagement of the solid phase pharmaceutical waste material with the cutting element.

Clause 44: The waste receiver of clauses 42 or 43, wherein the solid waste guide further includes a funnel member including a plurality of inclined surfaces oriented towards one another and spaced apart from one another to define a first gap positioned above the cutting element such that the funnel member is adapted to guide the solid waste material along the inclined surfaces towards the first gap.

Clause 45: The waste receiver of any of clauses 41-44, further including a barrier coupled to the body portion with the barrier movable from an open configuration to permit insertion of the solid phase pharmaceutical waste material within the solid receiver guide and a closed configuration to prevent the insertion of the solid phase pharmaceutical waste material within the solid receiver guide.

Clause 46: The waste receiver of clause 45, further including a biasing element coupled to the body portion and the barrier and adapted to bias the barrier to the closed configuration.

Clause 47: A method of converting a waste receiver for receiving a single phase of pharmaceutical waste material into a waste receiver for receiving two phases of pharmaceutical waste material with the waste receiver including a receiver body defining an opening and including an inner surface defining a container volume in fluid communication with the opening, opposing upper and lower walls, and at least one sidewall extend between the upper and lower walls, the method including the step of: positioning a body portion of a diverter at least partially within the receiver body such that a rim of the body portion is positioned adjacent the opening of the receiver body, a solid receiver guide coupled to the body portion is disposed within the receiver body with the solid receiver guide adapted to direct one of the two phases of the pharmaceutical waste material to a solid waste volume within the container volume, and a liquid receiver guide coupled to the body portion is disposed within the receiver body with the liquid receiver guide adapted to direct the other one of the two phases of the pharmaceutical waste material to a liquid waste volume within the container volume and separate from the solid waste volume.

Clause 48: The method of clause 47, further including the step of securing the rim of the body portion to the receiver body.

Clause 49: A waste disposal system for receiving pharmaceutical waste material including at least one of a solid phase pharmaceutical waste material and a liquid phase pharmaceutical waste material, the waste receiver system including: a waste receiver including a receiver body defining an opening and including an inner surface defining a container volume in fluid communication with the opening, and an outer surface opposite the inner surface, the outer surface defining a lock passageway separate from the opening; the waste receiver further includes a cover adapted to be coupled with the receiver body over the opening to seal the pharmaceutical waste material within the container volume for disposal of the waste receiver; the waste receiver further includes a cover retention feature sized to removably receive the cover with the cover retention feature configured to cooperate with a locking assembly to prevent removal of the cover when the locking assembly secures the waste receiver to a fixed surface, the cover coupled to the cover retention feature.

Clause 50: A method of operating a waste disposal system for receiving a pharmaceutical waste and securing a waste receiver to a fixed surface and locking assembly, the method including: providing a waste receiver including a receiver body defining an opening and including an inner surface defining a container volume in fluid communication with the opening, and an outer surface opposite the inner surface, the outer surface defining a lock passageway separate from the opening; the waste receiver further includes a cover retention feature, and a cover; positioning the waste receiver such that the lock passageway at least partially surrounds the locking assembly; locking the locking assembly to secure the waste receiver to the fixed surface such that the cover retention feature and the and the locking assembly cooperate to prevent removal of the cover when the locking assembly is actuated.

Clause 51: The method of clause 50, further including inserting pharmaceutical waste into the container volume.

Clause 52: The method of clause 51, further including unlocking the locking assembly to allow removal of the cover from the cover retention feature.

Clause 53: The method of clause 52, further including removing the cover from the cover retention feature, and securing the cover to close the opening.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A waste receiver for receiving a pharmaceutical waste material including at least a solid phase pharmaceutical waste material and a liquid phase pharmaceutical waste material with said waste receiver adapted to be releasably secured to a fixed surface, said waste receiver comprising:
   a receiver body defining an opening and comprising an inner surface defining a container volume in fluid communication with said opening;
   a solid receiver guide coupled to said receiver body and adapted to direct the solid phase pharmaceutical waste material to a solid waste volume within said container volume;
   a cutting element positioned within said solid waste volume to cut the solid phase pharmaceutical waste material; and
   a pushing member movably disposed within said solid receiver guide and comprising a main body defining a handle, and a leg extending from said main body opposite said handle with said handle adapted to receive an input from a user to move said pushing member between a first position in which said main body is spaced from said solid receiver guide to provide a window partially defined between said main body, said leg, and said solid receiver guide for receiving the solid phase pharmaceutical waste material, and a second position in which said main body is adjacent to said solid receiver guide to facilitate engagement of the solid phase pharmaceutical waste material with said cutting element.

2. The waste receiver of claim 1, wherein at least a portion of said leg of said pushing member is disposed within said solid waste volume when said pushing member is in said first and second positions.

3. The waste receiver of claim 1, wherein said pushing member further comprises a foot extending from said leg with said foot adapted to interfere with said solid receiver guide as said pushing member is in said first position to prevent said pushing member from decoupling from said waste receiver.

4. The waste receiver of claim 1, wherein said pushing member further comprises a gripping member coupled to said main body and adapted to engage a patch comprising the solid phase pharmaceutical waste material positioned within said window and said pushing member is moved from said first position to said second position.

5. The waste receiver of claim 1, wherein said main body of said pushing member further defines a first portion and a second portion spaced apart from one another to define a slot therebetween with said slot sized to receive said cutting element.

6. The waste receiver of claim 1, wherein said solid receiver guide defines an elongate opening with said cutting element oriented substantially perpendicular to said elongate opening.

7. The waste receiver of claim 1, wherein said solid waste guide further comprises a funnel member comprising a plurality of sections each comprising an inclined surface and spaced apart from one another to define a first gap positioned above said cutting element such that said funnel member is adapted to guide the solid waste material along said inclined surfaces towards said first gap to position the solid phase waste material directly above an edge of said cutting element.

8. The waste receiver of claim 7, wherein said plurality of sections are spaced apart from one another to define a second gap with said pushing member adapted to be slidably moved through said second gap as said pushing member moves from said first position to said second position, thereby facilitating the solid waste material moving through said first and second gaps and into engagement with said cutting element.

9. The waste receiver of claim 1, further comprising a liquid receiver guide coupled to said receiver body and adapted to direct the liquid phase pharmaceutical waste material to a liquid waste volume within said container volume separate from said solid waste volume.

10. The waste receiver of claim 9, further comprising a cover adapted to be removably coupled with said receiver body to seal the solid phase pharmaceutical waste material and the liquid phase pharmaceutical waste material within the receiver body for disposal of said waste receiver.

11. A waste receiver for receiving a pharmaceutical waste material including at least a solid phase pharmaceutical waste material and a liquid phase pharmaceutical waste material with said waste receiver adapted to be releasably secured to a fixed surface, said waste receiver comprising:
   a receiver body defining an opening and comprising an inner surface defining a container volume in fluid communication with said opening;
   a solid receiver guide coupled to said receiver body and adapted to direct the solid phase pharmaceutical waste material to a solid waste volume within said container volume;
   a cutting element coupled to said solid receiver guide and disposed within said solid waste volume, wherein said solid receiver guide comprises a funnel member defining a first gap above said cutting element; and
a pushing member movably disposed within said solid receiver guide and adapted to receive and input and move the solid phase pharmaceutical waste material through said solid receiver guide with said pushing member comprising a main body defining a handle to receive the input, and a gripping member coupled to said main body, wherein said gripping member is adapted to impale a patch comprising the solid phase pharmaceutical waste material and retain the patch as said main body moves the patch through said first gap and into engagement with said cutting element.

12. The waste receiver of claim 11, wherein said gripping member is a spike.

13. The waste receiver of claim 11, wherein said first gap bilaterally bisects said funnel member.

14. A waste receiver for receiving a pharmaceutical waste material including at least a solid phase pharmaceutical waste material and a liquid phase pharmaceutical waste material with said waste receiver adapted to be releasably secured to a fixed surface, said waste receiver comprising:
a receiver body defining an opening and comprising an inner surface defining a container volume in fluid communication with said opening;
a solid receiver guide coupled to said receiver body and adapted to direct the solid phase pharmaceutical waste material to a solid waste volume within said container volume;
a cutting element coupled to said solid receiver guide and disposed within said solid waste volume; and
a pushing member having a main body and movably disposed within said solid receiver guide and adapted to facilitate moving the solid phase pharmaceutical waste material through said solid receiver guide,
wherein said solid receiver guide comprises:
a funnel member comprising a plurality of flexible sections spaced apart from one another to define a first gap above said cutting element, and
a second gap smaller than a thickness of said main body of said pushing member,
wherein said pushing member is adapted slidably move through said second gap with said flexible sections adapted to resiliently deflect away from said pushing member as said main body of said pushing member moves the solid phase pharmaceutical waste material through said first and second gaps and into engagement with said cutting element.

15. The waste receiver of claim 14, wherein each of said flexible sections comprises an inclined surface with said inclined surfaces oriented towards one another to guide the solid waste material towards said first gap to position the solid phase waste material directly above an edge of said cutting element.

16. The waste receiver of claim 14, wherein said second gap is perpendicular to said first gap.

17. The waste receiver of claim 14, wherein said plurality of sections is further defined as four symmetrical sections.

18. The waste receiver of claim 14, wherein said first gap bilaterally bisects said funnel member in a lateral direction and said second gap bilaterally bisects said funnel member in a longitudinal direction.

19. The waste receiver of claim 14, wherein said cutting element is oriented parallel with said first gap.

20. The waste receiver of claim 14, wherein said first and second gaps are sized to be smaller than pills comprising the solid waste pharmaceutical material such that the pills descend under influence of gravity to be supported on said sections above said first gap.

* * * * *